US012742017B2

(12) United States Patent
Chen et al.

(10) Patent No.: US 12,742,017 B2
(45) Date of Patent: Sep. 22, 2026

(54) ANTI-CD36 ANTIBODIES AND USES THEREOF

(71) Applicants: ELIXIRON IMMUNOTHERAPEUTICS (HONG KONG) LIMITED, Hong Kong (CN); Hung-Kai Chen, Los Altos, CA (US)

(72) Inventors: Hung-Kai Chen, Los Altos, CA (US); Huey-Wen Hsiao, Taipei City (TW); Pandelakis Andreas Koni, Larkspur, CA (US); Pei-Han Chung, Taipei City (TW)

(73) Assignee: Elixiron Immunotherapeutics (Hong Kong) Limited, Hong Kong (HK)

( * ) Notice: Subject to any disclaimer, the term of this patent is extended or adjusted under 35 U.S.C. 154(b) by 142 days.

(21) Appl. No.: 18/844,588

(22) PCT Filed: Mar. 6, 2023

(86) PCT No.: PCT/US2023/063766

§ 371 (c)(1),
(2) Date: Sep. 6, 2024

(87) PCT Pub. No.: WO2023/172863

PCT Pub. Date: Sep. 14, 2023

(65) Prior Publication Data

US 2025/0206837 A1 Jun. 26, 2025

Related U.S. Application Data

(60) Provisional application No. 63/317,160, filed on Mar. 7, 2022.

(51) Int. Cl.

| | |
|---|---|
| ***C07K 16/28*** | (2006.01) |
| ***A61P 35/00*** | (2006.01) |
| *A61K 39/00* | (2006.01) |

(52) U.S. Cl.

CPC .......... *C07K 16/2896* (2013.01); *A61P 35/00* (2018.01); *A61K 2039/505* (2013.01); *C07K 2317/622* (2013.01); *C07K 2317/73* (2013.01); *C07K 2317/76* (2013.01); *C07K 2317/92* (2013.01)

(58) Field of Classification Search

None

See application file for complete search history.

(56) References Cited

U.S. PATENT DOCUMENTS

| | | | |
|---|---|---|---|
| 2006/0147451 | A1 | 7/2006 | Kirchhofer |
| 2018/0371107 | A1 | 12/2018 | Lin |
| 2020/0157519 | A1 | 5/2020 | Chang |
| 2021/0341478 | A1 | 11/2021 | Shen |

OTHER PUBLICATIONS

International Search Report and Written Opinion for PCT/US2023/063766, Jul. 10, 2023.

*Primary Examiner* — Zachary S Skelding

(74) *Attorney, Agent, or Firm* — FisherBroyles, LLP; Adam K. Whiting

(57) ABSTRACT

The present disclosure provides antibodies which specifically bind to human CD36 protein (hCD36) and are capable of decreasing, inhibiting, and/or fully-blocking immune regulatory effects and/or ligand transport into cells mediated by CD36. Examples of CD36-mediated effects, among others, may include oxidized lipid transport into CD8 T cells potentially causing cell death and fatty acid transport in regulatory T cells increasing their survival and immune suppression in the tumor micro-environment (TME). The present disclosure also provides methods of using the antibodies (and compositions thereof) to treat various diseases and conditions responsive to decreasing, inhibiting and/or blocking CD36-dependent ligand transport into cells.

21 Claims, 20 Drawing Sheets

Specification includes a Sequence Listing.

FIG. 1C
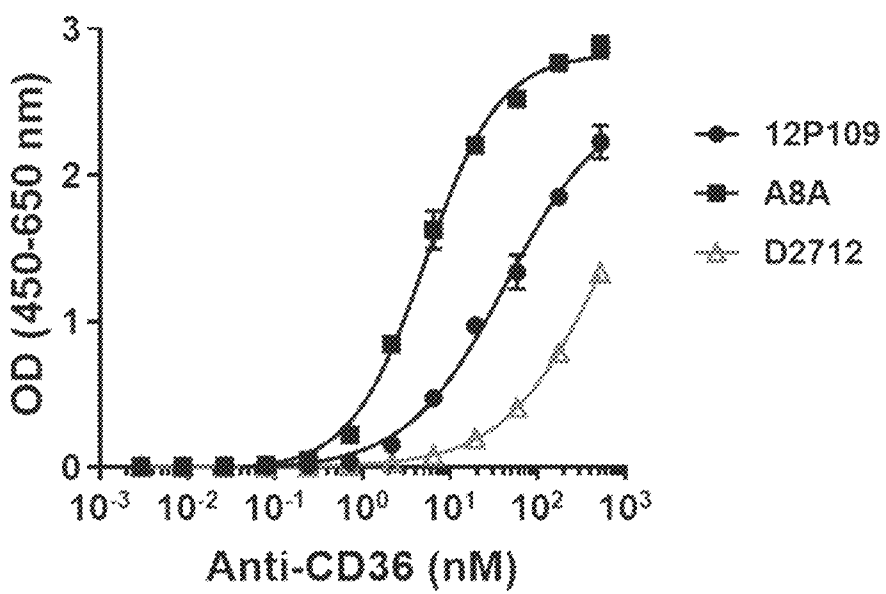
FIG. 1D
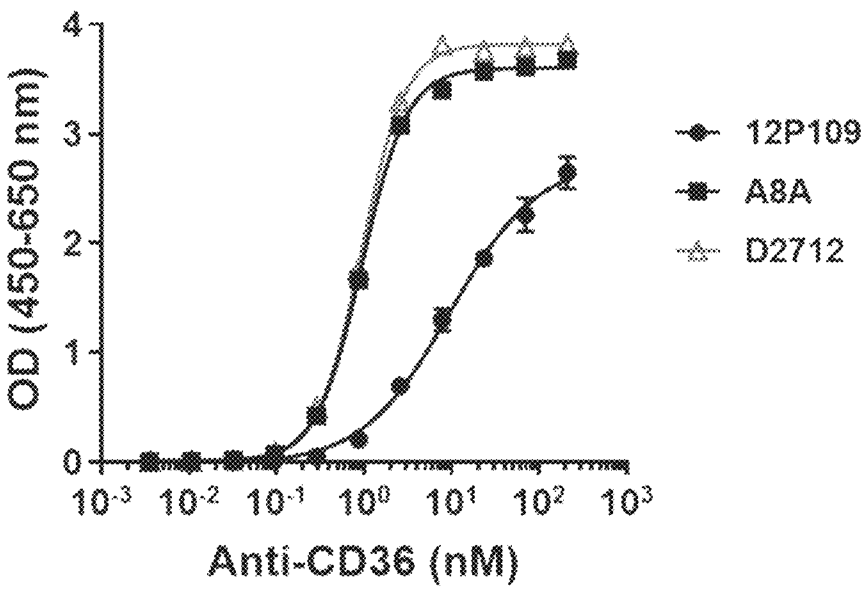

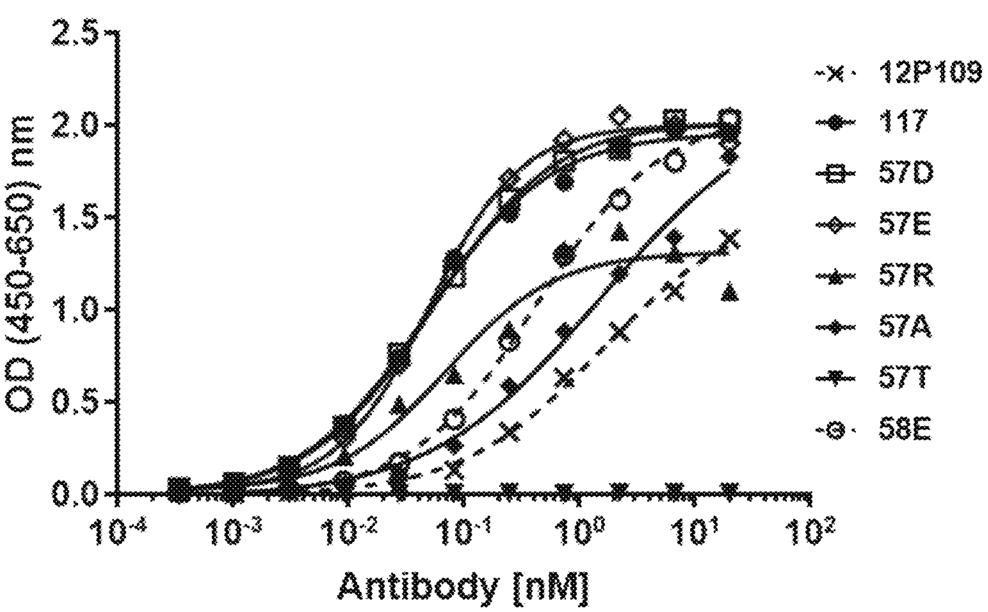
FIG. 2B
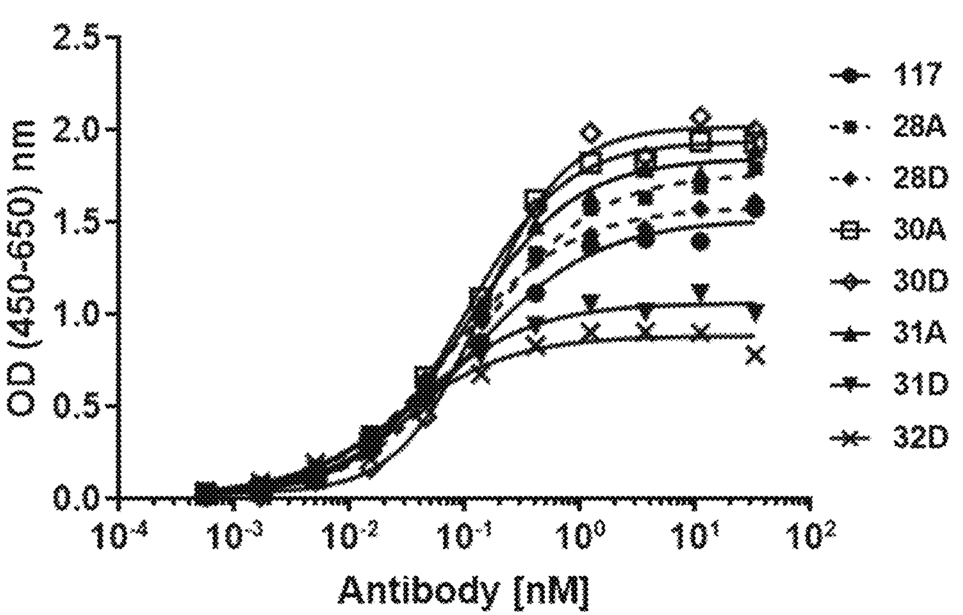

hCD36 ELISA

OD (450-650) nm
2.5
2.0
1.5
1.0
0.5
0.0
$10^{-4}$ $10^{-3}$ $10^{-2}$ $10^{-1}$ $10^{0}$ $10^{1}$ $10^{2}$
Antibody [nM]
117
30AA
30AT
30DA
30DT
30FA
30FT

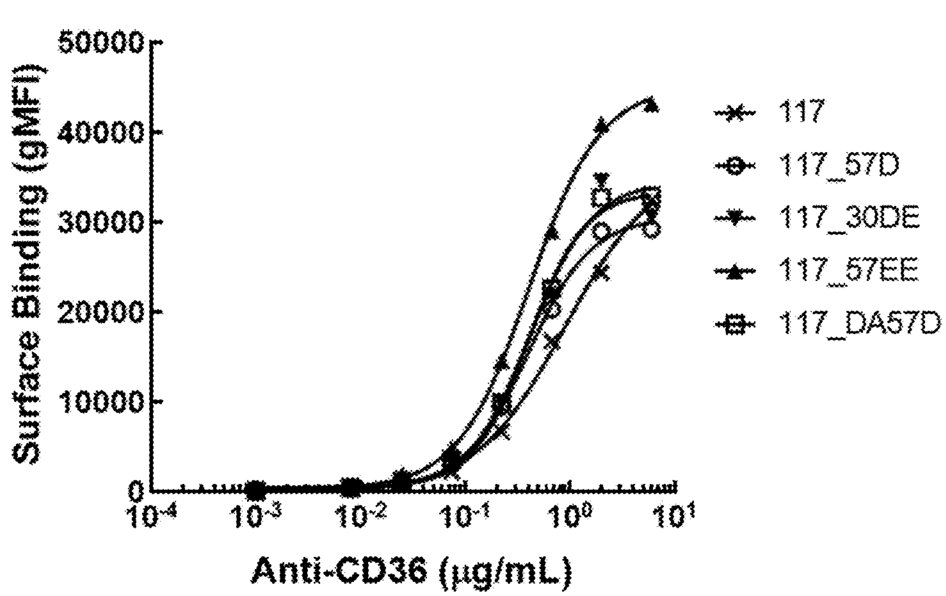
FIG. 4D
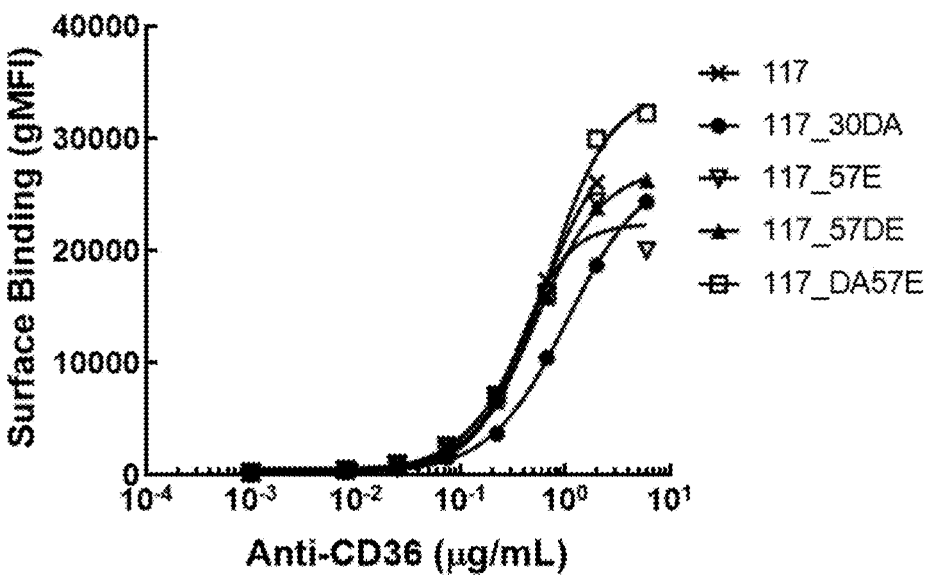

F293/mCD36

Surface Binding (gMFI)

30000
20000
10000
0

$10^{-4}$ $10^{-3}$ $10^{-2}$ $10^{-1}$ $10^{0}$ $10^{1}$

Anti-CD36 (μg/mL)

117
117_30DA
117_57E
117_57DE
117_DA57E

U937 cells (4°C)

oxLDL Binding (%)

40
30
20
10
0

**   ** no oxLDL
oxLDL
oxLDL+IgG
oxLDL+12P103
oxLDL+12P109
oxLDL+12P110
oxLDL+D2712

FIG. 10A
Tumor Growth
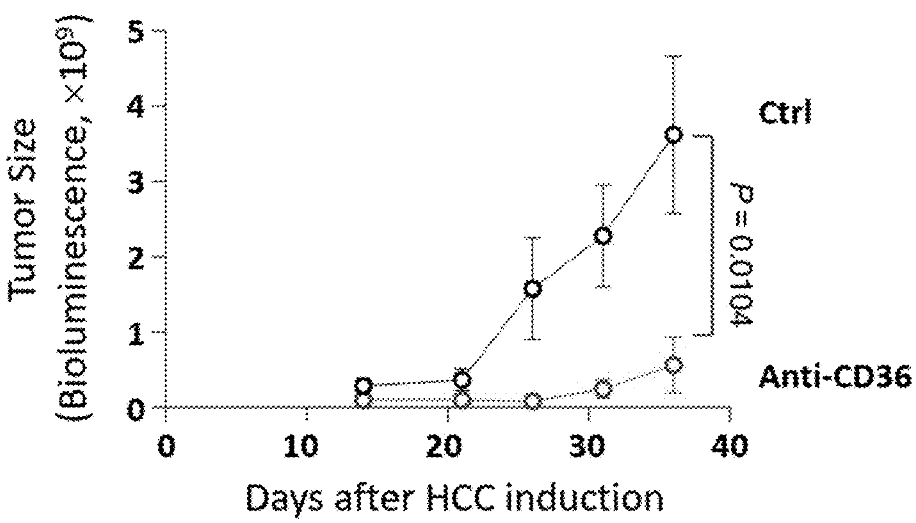
FIG. 10B
p= 0.0004
Liver Weight (g)
8
6
4
2
0
Ctrl
Anti-CD36
FIG. 10C
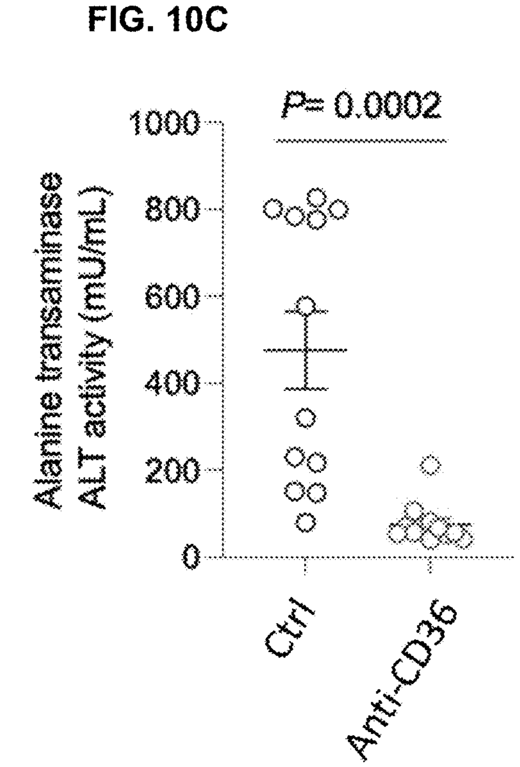

ANTI-CD36 ANTIBODIES AND USES THEREOF

CROSS REFERENCE TO RELATED APPLICATIONS

This application claims priority of U.S. Provisional Patent Application No. 63/317,160, filed Mar. 7, 2022, the entirety of which is hereby incorporated by reference herein.

FIELD

The present disclosure relates to antibodies which bind to CD36 and methods of using such antibodies.

REFERENCE TO SEQUENCE LISTING

The official copy of the Sequence Listing is submitted concurrently with the specification as a WIPO Standard ST.26 formatted XML file with file name of "09793-005WO1.xml", a creation date of Feb. 26, 2023, and a size of 75,330 bytes. The Sequence Listing filed via USPTO Patent Center is part of the specification and is incorporated in its entirety by reference herein.

BACKGROUND

Macrophages and other myeloid cells play a prominent role in creating as well as maintaining the immunosuppressive environment of tumors, and there are distinct microenvironments where tumor-associated macrophages (TAM) suppress immune response and promote other processes including angiogenesis, cancer cell motility and metastasis (Lewis & Pollard, 2006; Pollard, 2008; Wu et al., 2020). It was almost twenty years ago when, for example, vascular endothelial growth factor production by TAMs was proposed to play a role in lymphatic metastasis in several human cancers (e.g., Pepper et al., 2003), and 2006 when it was demonstrated that clodronate-liposome-mediated TAM depletion inhibits tumor growth in experimental models via mechanisms thought to include reduction of tumor angiogenesis (Zeisberger et al., 2006). What's more, macrophages not only promote tumor cell egress from a primary tumor but are also thought to facilitate seeding at distant metastatic sites (Joyce & Pollard, 2009; Psaila & Lyden, 2009).

While understanding of various pro-tumorigenic (often referred to as M2) and anti-tumorigenic M1 macrophages as well as other myeloid cells is still growing (e.g. see Wu et al., 2020), it has long been appreciated that high TAM number is linked to reduced patient survival (with a few notable exceptions) and is an independent prognostic factor in many cancers (Lewis & Pollard, 2006). Furthermore, myeloid cells referred to as myeloid-derived suppressor cells (MDSC) are found in peripheral blood and tumor tissues of cancer patients, and depletion or otherwise targeting of MDSC in mouse models results in improved immune responses and delayed tumor growth (Goedegebuure et al., 2011). MDSC are said to be somewhat heterogenous but are nonetheless described to fall into monocytic versus granulocytic subsets with distinct immunosuppressive mechanisms. Among other roles, tumor MDSC have been implicated in the recruitment and maintenance of immunosuppressive regulatory T cells, and to promote angiogenesis and metastasis (Goedegebuure et al., 2011; Oh et al., 2013). Like MDSC, as we now know at least, a CD45-positive but CD14-negative subset of human peripheral blood cells was described by Barrett et al. (2007) as expressing CD36 and the immunosuppressive cytokine, interleukin-10.

CD36 is a transmembrane cell-surface protein that, among other names, is also known as platelet glycoprotein 4, fatty acid translocase (FAT) and scavenger receptor class B member 3 (SCARB3). CD36 binds and transports fatty acids into cells but also binds a number of other ligands such as apoptotic cells, low-density lipoprotein, phospholipids and oxidized forms of the same (Pepino et al., 2014; Wang & Li, 2019). CD36 also bas a separate thrombospondin binding domain (Pepino et al., 2014; Wang & Li, 2019). Both of these two distinct functional events, thrombospondin versus fatty acid binding, can lead to various downstream signaling events that may differ depending on cell type and various other CD36 and/or ligand interacting partners (Pepino et al., 2014; Wang & Li, 2019). Fatty acid transport by CD36 is involved in metabolic 'wiring' of various cells if not required for cell differentiation state or survival. For example, fatty acid transport by CD36 has been shown to be required for M2 macrophage differentiation via a mechanism related to the level or state of endoplasmic reticulum stress (Oh et al., 2012).

CD36 has also been shown to be critical to M2 macrophage activation as measured by markers of immune-suppressive capacity such as PDL-2 expression (Huang et al., 2014). CD36-mediated lipid transport is also involved in the acquisition of immune-suppressive effectors during MDSC differentiation (Al-Khami et al., 2017). CD36-deficient mice have reduced numbers of tumor-resident MDSC in all (lung and colon) tumor models tested, when compared to tumor-bearing wild type mice, and this was reflected in tumors of wild type chimeric mice that were CD36-deficient in their bone marrow (Al-Khami et al., 2017). Most recently, TAMs were shown to be greatly reduced in melanoma and myeloma models in CD36-deficient mice, compared to such tumors of wild type mice, and that such TAM in wild type mice have elevated CD36 expression and lipid accumulation compared to normal macrophages (Su et al., 2020).

Given the importance of CD36-mediated fatty acid or other ligand uptake to M2 TAM and MDSC biology, it might be expected that blocking of CD36 ligand transport would reduce tumor growth, by resulting in reduced immunosuppressive capacity, angiogenesis and/or metastasis that would otherwise be promoted by M2 TAM and MDSC. Indeed, mouse tumor models showed that tumor growth (lung and colon) was greatly reduced in mice deficient in CD36, and that this was due to CD36 loss among bone marrow-derived cells (Al-Khami et al., 2017).

Besides myeloid cells, it has more recently been reported that CD36 is expressed on some tumor-resident regulatory T cells, and that blocking CD36 with an antibody that prevents CD36-mediated fatty acid transport results in reduced melanoma growth in experimental models (Wang et al., 2020). Furthermore, CD36-deficiency on mouse regulatory T cells alone was shown to be sufficient to cause reduced melanoma growth (Wang et al., 2020). Most recently, CD36 expression by tumor-resident CD8 T cells has been shown to impair their anti-tumor capacity, and to result in increased tumor CD8 T cell death by lipid peroxidation leading to ferroptosis (Ma et al., 2021). A previous report also described CD36 on tumor-infiltrated CD8 T cells and its adverse consequences on such CD8 T cells (Xu et al., 2020) and this report was later published in a peer-reviewed format (Xu et al., 2021).

There are also many reports of a role for ligand transport by CD36 expressed on tumor cells. For example, CD36 has been implicated in breast cancer tamoxifen resistance (Liang et al., 2018), melanoma chemotherapy resistance (Alioa et al., 2019) and lung cancer HER2-targeted therapy resistance (Feng et al., 2019). As long ago as 1993, CD36 was linked to adriamycin-resistance in a screen of an adriamycin-resistant subline of the human myelogenous leukemia line, K562, albeit over-expression of CD36 in the adriamycin-sensitive parental cell line did not alone confer adriamycin resistance (Sugimoto et al., 1993). CD36 is also involved in increased glioblastoma (Hale et al., 2014) and leukemic (Ye et al., 2016) stem cell self-renewal, survival and/or proliferation. That is, CD36 appears to be involved in chemotherapy-resistance by leukemic stem cells in adipose tissue niches (Ye et al., 2016). Glioblastoma formation using patient-derived glioblastoma stem cells in a xenograft mouse model was greatly reduced when CD36 was 'knocked-down' in the stem cells by RNA interference, and proliferation of glioblastoma stem cells was increased in a CD36-dependent manner by exposure to oxidized low-density lipoprotein (Hale et al., 2014). CD36 was also shown to be an informative biomarker of brain malignancy and negatively correlated with patient prognosis (Hale et al., 2014).

More recently, CD36 was shown to be important to prostate cancer progression and tumor growth in mouse models and reducing CD36 expression in prostate cancer cells by RNA interference or otherwise blocking CD36-mediated lipid transport with antibodies caused reduced cell migration capacity and tumor growth in mouse models (Watt et al., 2019).

CD36 has also been proposed as a prognostic metastasis biomarker in various cancers (reviewed by Enciu et al., 2018) and has been shown to facilitate metastasis of oral squamous cell carcinoma (OSCC) cells, breast cancer cells and melanoma cells in mouse models (PCT/EP20 16/073208; Pascual et al., 2017). OSCC metastasis was seen after cell injection into an orthotopic site (the tongue) and this was reduced by an antibody that blocks fatty acid transport by CD36. Melanoma and breast cancer cells were injected into the blood of mice so that they could potentially colonize metastatic niches, and this metastasis was reduced when using such cells in which CD36 was 'knocked down' by RNA interference (PCT/EP20 16/073208; Pascual et al., 2017). As mentioned above, CD36 is also anticipated to be involved in intravasation of tumor cells from a primary tumor site into lymphatic and/or blood circulation in the first place, via its roles on immune system myeloid cells. Fatty acid transport by CD36 on liver cancer cells was also shown to cause increased epithelial-mesenchymal transition, and chemical inhibition of CD36-mediated fatty acid transport reduced this phenotype as well as liver cancer cell migration (Nath et al., 2015).

All of the above paints a picture in which fatty acid or other ligand transport by CD36 into cells is involved in metabolic adaptation or differentiation of various cell types but it should also be highlighted that CD36 signaling leads to more direct immunosuppressive effects. Some of these were mentioned above but it should be highlighted that it has been proposed that apoptotic cell binding via CD36 normally facilitates homeostatic anti-inflammatory processes, and apoptotic cell binding via CD36 is at least in part responsible for IL-10 production by macrophages (among other immunosuppressive effects on macrophages) subsequent to apoptotic cell binding (Chung et al., 2007). CD36-mediated ligand transport may also lead to immunosuppressive metabolites. That is, increased arachidonic acid production as a result of CD36 ligand-induced intracellular signaling provides substrate for production of prostaglandins (e.g. Kuda et al., 2011), some of which are known to have wide-ranging immune-modulatory effects (e.g. see Wang & Dubois, 2006; Mizuno et al., 2019). Certainly, immune-suppressive prostaglandin E2 is produced in many cancers by tumor cells as well as immune system cells, including myeloid cells and others (Wang & Dubois, 2006; Mizuno et al., 2019) such as inducible regulatory T cells (Whiteside & Jackson, 2013). What's more, mouse macrophages at least have been shown to produce prostaglandin E2 in a CD36-dependent manner, albeit this was not in a cancer model (Almeida et al., 2014).

Besides the many roles of CD36 in cancer, CD36 ligand transport apparently plays a significant pathological role in foam cell formation in atherosclerosis (e.g., Zhao et al., 2018), non-alcoholic fatty liver disease (e.g., Rada et al., 2020) and other conditions. Thus, there are several potential applications for antibodies that prevent apoptotic cell or other ligand binding/transport by CD36.

SUMMARY

The present disclosure provides anti-CD36 antibodies that specifically bind human CD36 with high affinity. The antibodies are capable of decreasing, inhibiting, and/or fully-blocking immune regulatory effects mediated by CD36, including CD36-mediated fatty acid transport (e.g., cellular uptake of oxidized low-density lipoprotein, or 'oxLDL').

In at least one embodiment, the present disclosure provides an anti-CD36 antibody comprising (i) a first light chain complementary determining region (CDR-L1), a second light chain complementary determining region (CDR-L2), and a third light chain complementary determining region (CDR-L3), and/or (ii) a first heavy chain complementary determining region (CDR-H1), a second heavy chain complementary determining region (CDR-H2), and a third heavy chain complementary determining region (CDR-H3), wherein:

(a) CDR-H1 comprises the amino acid sequence of SEQ ID NO: 3, 21, 24, or 27;
(b) CDR-H2 comprises the amino acid sequence of SEQ ID NO: 4, 28, 31, 34, 37, 40, or 43;
(c) CDR-H3 comprises the amino acid sequence of SEQ ID NO: 5;
(d) CDR-L1 comprises an amino acid sequence selected from SEQ ID NO: 7;
(e) CDR-L2 comprises an amino acid sequence selected from SEQ ID NO: 8, 12, or 15; and
(f) CDR-L3 comprises an amino acid sequence selected from SEQ ID NO: 9, 13, or, 18.

In at least one embodiment of the anti-CD36 antibody of the present disclosure:

(a) CDR-H1 comprises the amino acid sequence of SEQ ID NO: 3, CDR-H2 comprises the amino acid sequence of SEQ ID NO: 4, CDR-H3 comprises the amino acid sequence of SEQ ID NO: 5, CDR-L1 comprises the amino acid sequence of SEQ ID NO: 7, CDR-L2 comprises the amino acid sequence of SEQ ID NO: 8, and CDR-L3 comprises the amino acid sequence of SEQ ID NO: 9;
(b) CDR-H1 comprises the amino acid sequence of SEQ ID NO: 3, CDR-H2 comprises the amino acid sequence of SEQ ID NO: 4, CDR-H3 comprises the amino acid sequence of SEQ ID NO: 5, CDR-L1 comprises the amino acid sequence of SEQ ID NO: 7, CDR-L2 comprises the amino acid sequence of SEQ ID NO: 12, and CDR-L3 comprises the amino acid sequence of SEQ ID NO: 13;

(c) CDR-H1 comprises the amino acid sequence of SEQ ID NO: 3, CDR-H2 comprises the amino acid sequence of SEQ ID NO: 4, CDR-H3 comprises the amino acid sequence of SEQ ID NO: 5, CDR-L1 comprises the amino acid sequence of SEQ ID NO: 7, CDR-L2 comprises the amino acid sequence of SEQ ID NO: 15, and CDR-L3 comprises the amino acid sequence of SEQ ID NO: 13;

(d) CDR-H1 comprises the amino acid sequence of SEQ ID NO: 3, CDR-H2 comprises the amino acid sequence of SEQ ID NO: 4, CDR-H3 comprises the amino acid sequence of SEQ ID NO: 5, CDR-L1 comprises the amino acid sequence of SEQ ID NO: 7, CDR-L2 comprises the amino acid sequence of SEQ ID NO: 15, and CDR-L3 comprises the amino acid sequence of SEQ ID NO: 18;

(e) CDR-H1 comprises the amino acid sequence of SEQ ID NO: 21, CDR-H2 comprises the amino acid sequence of SEQ ID NO: 4, CDR-H3 comprises the amino acid sequence of SEQ ID NO: 5, CDR-L1 comprises the amino acid sequence of SEQ ID NO: 7, CDR-L2 comprises the amino acid sequence of SEQ ID NO: 15, and CDR-L3 comprises the amino acid sequence of SEQ ID NO: 18;

(f) CDR-H1 comprises the amino acid sequence of SEQ ID NO: 24, CDR-H2 comprises the amino acid sequence of SEQ ID NO: 4, CDR-H3 comprises the amino acid sequence of SEQ ID NO: 5, CDR-L1 comprises the amino acid sequence of SEQ ID NO: 7, CDR-L2 comprises the amino acid sequence of SEQ ID NO: 15, and CDR-L3 comprises the amino acid sequence of SEQ ID NO: 18;

(g) CDR-H1 comprises the amino acid sequence of SEQ ID NO: 27, CDR-H2 comprises the amino acid sequence of SEQ ID NO: 28, CDR-H3 comprises the amino acid sequence of SEQ ID NO: 5, CDR-L1 comprises the amino acid sequence of SEQ ID NO: 7, CDR-L2 comprises the amino acid sequence of SEQ ID NO: 15, and CDR-L3 comprises the amino acid sequence of SEQ ID NO: 18;

(h) CDR-H1 comprises the amino acid sequence of SEQ ID NO: 3, CDR-H2 comprises the amino acid sequence of SEQ ID NO: 31, CDR-H3 comprises the amino acid sequence of SEQ ID NO: 5, CDR-L1 comprises the amino acid sequence of SEQ ID NO: 7, CDR-L2 comprises the amino acid sequence of SEQ ID NO: 15, and CDR-L3 comprises the amino acid sequence of SEQ ID NO: 18;

(i) CDR-H1 comprises the amino acid sequence of SEQ ID NO: 3, CDR-H2 comprises the amino acid sequence of SEQ ID NO: 34, CDR-H3 comprises the amino acid sequence of SEQ ID NO: 5, CDR-L1 comprises the amino acid sequence of SEQ ID NO: 7, CDR-L2 comprises the amino acid sequence of SEQ ID NO: 15, and CDR-L3 comprises the amino acid sequence of SEQ ID NO: 18;

(j) CDR-H1 comprises the amino acid sequence of SEQ ID NO: 3, CDR-H2 comprises the amino acid sequence of SEQ ID NO: 37, CDR-H3 comprises the amino acid sequence of SEQ ID NO: 5, CDR-L1 comprises the amino acid sequence of SEQ ID NO: 7, CDR-L2 comprises the amino acid sequence of SEQ ID NO: 15, and CDR-L3 comprises the amino acid sequence of SEQ ID NO: 18;

(k) CDR-H1 comprises the amino acid sequence of SEQ ID NO: 3, CDR-H2 comprises the amino acid sequence of SEQ ID NO: 40, CDR-H3 comprises the amino acid sequence of SEQ ID NO: 5, CDR-L1 comprises the amino acid sequence of SEQ ID NO: 7, CDR-L2 comprises the amino acid sequence of SEQ ID NO: 15, and CDR-L3 comprises the amino acid sequence of SEQ ID NO: 18; or (l) CDR-H1 comprises the amino acid sequence of SEQ ID NO: 24, CDR-H2 comprises the amino acid sequence of SEQ ID NO: 43, CDR-H3 comprises the amino acid sequence of SEQ ID NO: 5, CDR-L1 comprises the amino acid sequence of SEQ ID NO: 7, CDR-L2 comprises the amino acid sequence of SEQ ID NO: 15, and CDR-L3 comprises the amino acid sequence of SEQ ID NO: 18.

In at least one embodiment, the present disclosure provides an anti-CD36 antibody comprising: (i) a first heavy chain complementary determining region (CDR-H1), a second heavy chain complementary determining region (CDR-H2), and a third heavy chain complementary determining region (CDR-H3), wherein the CDR-H1, CDR-H2, and CDR-H3 sequences are from a VH region having an amino acid sequence selected from SEQ ID NO: 2, 20, 23, 26, 30, 33, 36, 39, and 42; and (ii) a first light chain complementary determining region (CDR-L1), a second light chain complementary determining region (CDR-L2), and a third light chain complementary determining region (CDR-L3), wherein the CDR-L1, CDR-L2, and CDR-L3 sequences are from a VL region having an amino acid sequence selected from SEQ ID NO: 6, 11, 14, and 17; wherein the CDR-L1, CDR-L2, CDR-L3, CDR-H1, CDR-H2 and CDR-H3 are according to Kabat numbering.

In at least one embodiment of the anti-CD36 antibody:

(a) the VH amino acid sequence is SEQ ID NO: 2 and the VL amino acid sequence is SEQ ID NO: 6;

(b) the VH amino acid sequence is SEQ ID NO: 2 and the VL amino acid sequence is SEQ ID NO: 11:

(c) the VH amino acid sequence is SEQ ID NO: 2 and the VL amino acid sequence is SEQ ID NO: 14;

(d) the VH amino acid sequence is SEQ ID NO: 2 and the VL amino acid sequence is SEQ ID NO: 17;

(e) the VH amino acid sequence is SEQ ID NO: 20 and the VL amino acid sequence is SEQ ID NO: 17;

(f) the VH amino acid sequence is SEQ ID NO: 23 and the VL amino acid sequence is SEQ ID NO: 17;

(g) the VH amino acid sequence is SEQ ID NO: 26 and the VL amino acid sequence is SEQ ID NO: 17;

(h) the VH amino acid sequence is SEQ ID NO: 30 and the VL amino acid sequence is SEQ ID NO: 17;

(i) the VH amino acid sequence is SEQ ID NO: 33 and the VL amino acid sequence is SEQ ID NO: 17;

(j) the VH amino acid sequence is SEQ ID NO: 36 and the VL amino acid sequence is SEQ ID NO: 17;

(k) the VH amino acid sequence is SEQ ID NO: 39 and the VL amino acid sequence is SEQ ID NO: 17; or (l) the VH amino acid sequence is SEQ ID NO: 42 and the VL amino acid sequence is SEQ ID NO: 17.

In at least one embodiment of the anti-CD36 antibody of the present disclosure, the antibody comprises a heavy chain variable domain (VH) amino acid sequence having at least 90% identity to a sequence selected from SEQ ID NO: 2, 20, 23, 26, 30, 33, 36, 39, or 42; and/or a light chain variable domain (VL) amino acid sequence having at least 90% identity to a sequence selected from SEQ ID NO: 6, 11, 14, or 17.

In at least one embodiment of the anti-CD36 antibody of the present disclosure:

(a) the antibody comprises a VH amino acid sequence having at least 90% identity to SEQ ID NO: 2 and a VL amino acid sequence having at least 90% identity to SEQ ID NO: 6;
(b) the antibody comprises a VH amino acid sequence having at least 90% identity to SEQ ID NO: 2 and a VL amino acid sequence having at least 90% identity to SEQ ID NO: 11:
(c) the antibody comprises a VH amino acid sequence having at least 90% identity to SEQ ID NO: 2 and a VL amino acid sequence having at least 90% identity to SEQ ID NO: 14;
(d) the antibody comprises a VH amino acid sequence having at least 90% identity to SEQ ID NO: 2 and a VL amino acid sequence having at least 90% identity to SEQ ID NO: 17;
(e) the antibody comprises a VH amino acid sequence having at least 90% identity to SEQ ID NO: 20 and a VL amino acid sequence having at least 90% identity to SEQ ID NO: 17;
(f) the antibody comprises a VH amino acid sequence having at least 90% identity to SEQ ID NO: 23 and a VL amino acid sequence having at least 90% identity to SEQ ID NO: 17;
(g) the antibody comprises a VH amino acid sequence having at least 90% identity to SEQ ID NO: 26 and a VL amino acid sequence having at least 90% identity to SEQ ID NO: 17;
(h) the antibody comprises a VH amino acid sequence having at least 90% identity to SEQ ID NO: 30 and a VL amino acid sequence having at least 90% identity to SEQ ID NO: 17;
(i) the antibody comprises a VH amino acid sequence having at least 90% identity to SEQ ID NO: 33 and a VL amino acid sequence having at least 90% identity to SEQ ID NO: 17;
(j) the antibody comprises a VH amino acid sequence having at least 90% identity to SEQ ID NO: 36 and a VL amino acid sequence having at least 90% identity to SEQ ID NO: 17;
(k) the antibody comprises a VH amino acid sequence having at least 90% identity to SEQ ID NO: 39 and a VL amino acid sequence having at least 90% identity to SEQ ID NO: 17; or
(l) the antibody comprises a VH amino acid sequence having at least 90% identity to SEQ ID NO: 42 and a VL amino acid sequence having at least 90% identity to SEQ ID NO: 17.

In at least one embodiment of the anti-CD36 antibody of the present disclosure, the antibody comprises a heavy chain (HC) amino acid sequence having at least 90% identity to a sequence selected from SEQ ID NO: 44, 48, 50, 51, 52, 53, 54, 55, 56, or 57, and/or a light chain (LC) amino acid sequence having at least 90% identity to a sequence selected from SEQ ID NO: 45, 46, 47, or 49.

In at least one embodiment of the anti-CD36 antibody of the present disclosure, the antibody comprises:
(a) an HC amino acid sequence having at least 90% identity to SEQ ID NO: 44 and an LC amino acid sequence having at least 90% identity to SEQ ID NO: 45;
(b) an HC amino acid sequence having at least 90% identity to SEQ ID NO: 44 and an LC amino acid sequence having at least 90% identity to SEQ ID NO: 46;
(c) an HC amino acid sequence having at least 90% identity to SEQ ID NO: 44 and an LC amino acid sequence having at least 90% identity to SEQ ID NO: 47;
(d) an HC amino acid sequence having at least 90% identity to SEQ ID NO: 44, and an LC amino acid sequence having at least 90% identity to SEQ ID NO: 49;
(e) an HC amino acid sequence having at least 90% identity to SEQ ID NO: 48, and an LC amino acid sequence having at least 90% identity to SEQ ID NO: 49;
(f) an HC amino acid sequence having at least 90% identity to SEQ ID NO: 50 and an LC amino acid sequence having at least 90% identity to SEQ ID NO: 49;
(g) an HC amino acid sequence having at least 90% identity to SEQ ID NO: 51 and an LC amino acid sequence having at least 90% identity to SEQ ID NO: 49;
(h) an HC amino acid sequence having at least 90% identity to SEQ ID NO: 52 and an LC amino acid sequence having at least 90% identity to SEQ ID NO: 49;
(i) an HC amino acid sequence having at least 90% identity to SEQ ID NO: 53 and an LC amino acid sequence having at least 90% identity to SEQ ID NO: 49;
(j) an HC amino acid sequence having at least 90% identity to SEQ ID NO: 54 and an LC amino acid sequence having at least 90% identity to SEQ ID NO: 49;
(k) an HC amino acid sequence having at least 90% identity to SEQ ID NO: 55 and an LC amino acid sequence having at least 90% identity to SEQ ID NO: 49;
(l) an HC amino acid sequence having at least 90% identity to SEQ ID NO: 56 and an LC amino acid sequence having at least 90% identity to SEQ ID NO: 49; or
(m) an HC amino acid sequence having at least 90% identity to SEQ ID NO: 57 and an LC amino acid sequence having at least 90% identity to SEQ ID NO: 49.

In at least one embodiment of the anti-CD36 antibody of the present disclosure:
(a) the antibody binds to human CD36 with a binding affinity of $1\times10^{-8}$ M or less, $1\times10^{-9}$ M or less, $1\times10^{-10}$ M or less; optionally, wherein the binding affinity is measured by equilibrium dissociation constant ($K_D$) to a hCD36 polypeptide of SEQ ID NO: 58 or 59;
(b) the antibody binds to mouse CD36 with a binding affinity of $1\times10^{-8}$ M or less, $1\times10^{-9}$ M or less, $1\times10^{-10}$ M or less; optionally, wherein the binding affinity is measured by equilibrium dissociation constant ($K_D$) to a mCD36 polypeptide of SEQ ID NO: 60 or 61;
(c) the antibody binds to rhesus CD36 with a binding affinity of $1\times10^{-8}$ M or less, $1\times10^{-9}$ M or less, $1\times10^{-10}$ M or less; optionally, wherein the binding affinity is measured by equilibrium dissociation constant ($K_D$) to a rhesus CD36 polypeptide of SEQ ID NO: 62 or 63;
(d) the antibody inhibits CD36-dependent oxidized LDL uptake in F293 cells that overexpress surface human CD36 by at least 65%, at least 75%, at least 85%, at least 95%, or at least 100%; optionally, wherein at an oxLDL concentration of 1-10 μg/mL the antibody has an $IC_{50}$ of 5 nM or less, 1 nM or less, 0.5 nM or less, or 0.1 nM or less;

(e) the antibody inhibits CD36-dependent oxidized LDL uptake in U937 cells by at least 65%, at least 75%, at least 85%, at least 95%, or at least 100%; optionally, wherein at an oxLDL concentration of 1-10 μg/mL the antibody has an $IC_{50}$ of 5 nM or less, 1 nM or less, 0.5 nM or less, or 0.1 nM or less; and/or (f) the antibody inhibits CD36-dependent oxidized LDL uptake in mouse CD45+ TILs by at least 65%, at least 75%, at least 85%, at least 95%, or at least 100%; optionally, wherein at an oxLDL concentration of 1-10 μg/mL the antibody has an $IC_{50}$ of 5 nM or less, 1 nM or less, 0.5 nM or less, or 0.1 nM or less.

The present disclosure also provides embodiments of the anti-CD36 antibodies disclosed herein, including embodiments wherein: (i) the antibody is a human, humanized, or chimeric antibody; (ii) the antibody comprises a fusion to a protein; optionally, a fusion to an immunostimulatory cytokine, such as IL-2, IL-7, IL-10, IL-12, IL-15, IL-21, or IFN-α; (iii) the antibody is a full length antibody of class IgG, optionally, wherein the class IgG antibody has an isotype selected from IgG1, IgG2, IgG3, and IgG4; (iv) the antibody comprises an Fc region variant, optionally an Fc region variant that alters effector function and/or a variant that alters antibody half-life; (v) the antibody is an antibody fragment, optionally selected from the group consisting of $F(ab')_2$, Fab', Fab, Fv, single domain antibody (VHH), and scFv; (vi) the antibody comprises an immunoconjugate, optionally, wherein the immunoconjugate comprises a therapeutic agent for treatment of a CD36-mediated disease or condition; or (vii) the antibody is a multi-specific antibody, optionally a bispecific antibody.

In at least one embodiment the present disclosure provides an isolated polynucleotide or a vector comprising a polynucleotide, wherein the polynucleotide sequence encodes an anti-CD36 antibody of the present disclosure or a polypeptide chain of an anti-CD36 antibody of the present disclosure. In at least one embodiment, the isolated polynucleotide or vector comprises a sequence that encodes a polypeptide of an anti-CD36 antibody of the present disclosure. In at least one embodiment of the isolated polynucleotide or vector, the encoded polypeptide chain having an amino acid sequence comprising:

(a) CDR-H1 comprises the amino acid sequence of SEQ ID NO: 3, 21, 24, or 27; CDR-H2 comprises the amino acid sequence of SEQ ID NO: 4, 28, 31, 34, 37, 40, or 43; and CDR-H3 comprises the amino acid sequence of SEQ ID NO: 5;

(b) CDR-L1 comprises an amino acid sequence selected from SEQ ID NO: 7; CDR-L2 comprises an amino acid sequence selected from SEQ ID NO: 8, 12, or 15; and CDR-L3 comprises an amino acid sequence selected from SEQ ID NO: 9, 13, or, 18;

(c) a heavy chain variable domain ($V_H$) amino acid sequence having at least 90% identity to a sequence selected from SEQ ID NO: 2, 20, 23, 26, 30, 33, 36, 39, or 42;

(d) a light chain variable domain ($V_L$) amino acid sequence having at least 90% identity to a sequence selected from SEQ ID NO: 6, 11, 14, or 17;

(e) a heavy chain (HC) amino acid sequence having at least 90% identity to a sequence selected from SEQ ID NO: 44, 48, 50, 51, 52, 53, 54, 55, 56, or 57; and/or (f) a light chain (LC) amino acid sequence having at least 90% identity to a sequence selected from SEQ ID NO: 45, 46, 47, or 49.

In at least one embodiment the present disclosure also provides an isolated host cell comprising a polynucleotide or vector encoding an anti-CD36 antibody, or a polypeptide chain of an anti-CD36 antibody of the present disclosure. In at least one embodiment, the present disclosure also provides a method of producing an anti-CD36 antibody of present disclosure comprising culturing a host cell comprising a polynucleotide or vector encoding an anti-CD36 antibody so that an antibody is produced.

In at least one embodiment, the present disclosure provides a pharmaceutical composition comprising an anti-CD36 antibody of the present disclosure and a pharmaceutically acceptable carrier; optionally, wherein the composition further comprises a chemotherapeutic agent, and/or an antibody comprising a specificity for an immune checkpoint molecule.

In at least one embodiment, the present disclosure provides a method of treating a CD36-mediated disease in a subject, the method comprising administering to the subject a therapeutically effective amount of an anti-CD36 antibody of the present disclosure, or administering to the subject a therapeutically effective amount of a pharmaceutical composition of the present disclosure; optionally, wherein the disease is cancer; optionally, wherein the cancer is selected from colon cancer, pancreatic cancer, ovarian cancer, HCC, renal cancer, breast cancer, lung cancer, gastric cancer, melanoma, head and neck cancer, and oral cancer.

In at least one embodiment, the present disclosure provides a method for treating cancer in a subject, comprising administering to the subject a CD36 antagonist and a chemotherapeutic agent, and/or an antibody comprising a specificity for an immune checkpoint molecule; optionally, wherein the CD36 antagonist comprises an anti-CD36 antibody, a shRNA, a siRNA, a miRNA, a small molecule inhibitor of CD36, or a combination thereof.

BRIEF DESCRIPTION OF THE DRAWINGS

A better understanding of the novel features and advantages of the present disclosure will be obtained by reference to the following detailed description that sets forth illustrative embodiments, in which the principles of the disclosure are utilized, and the accompanying drawings (also "Figure" and "FIG." herein), of which:

FIG. 1A, FIG. 1B, FIG. 1C, and FIG. 1D depict ELISA results for exemplary anti-CD36 antibodies of the present disclosure (12P109, A8A) in full-length human IgG1 format binding to either recombinant human CD36.ECD (FIG. 1A, FIG. 1C) or mouse CD36.ECD (FIG. 1B, FIG. 1D). The ELISA was carried out as described in Example 1.

FIG. 2A, FIG. 2B, FIG. 2C, FIG. 2D, FIG. 2E, and FIG. 2F depict ELISA results for exemplary anti-CD36 antibodies of the present disclosure (12P109, and 117 variants) binding to recombinant human CD36.ECD. The ELISA was carried out as described in Example 1.

FIG. 4A, FIG. 4B, FIG. 4C, FIG. 4D, FIG. 4E, and FIG. 4F depict plots showing results from cell surface binding analysis by flow cytometry of exemplary anti-CD36 antibodies of the present disclosure (117 variants) to stable F293 cells overexpressing human CD36 ("hCD36") (FIG. 4A and FIG. 4B), rhesus CD36 (FIG. 4C and FIG. 4D), or murine CD36 ("mCD36") (FIG. 4E and FIG. 4F) as described in Example 2.

FIG. 10A, FIG. 10B, and FIG. 10C depict results measured in $\beta$-$catenin^{OE}/MYC^{OE}$ HCC model mice following treatment with the anti-CD36 antibody 117_DA57E as described in Example 6. FIG. 10A shows the tumor growth curve results measured by bioluminescence. FIG. 10B shows a plot of endpoint liver weight results. FIG. 10C shows a plot of plasma ALT (alanine transaminase) activity analysis results.

DETAILED DESCRIPTION

Figure 1A:
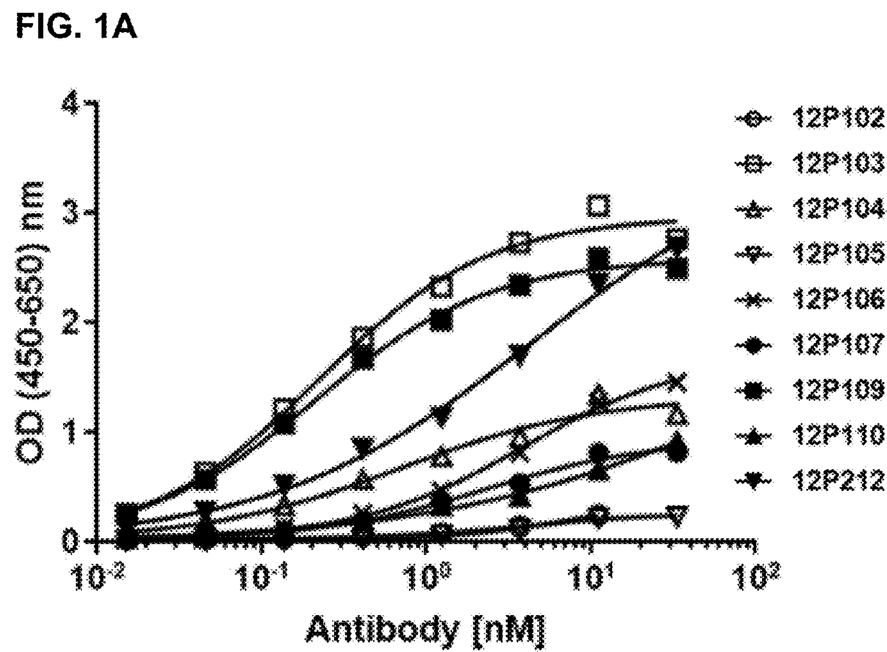

The present disclosure provides antibodies, including humanized antibodies, that specifically bind CD36 with high affinity and thereby inhibit, decrease, and/or fully block the function of CD36 as a cell surface protein involved in immune regulation, particularly the function of CD36-mediated fatty-acid and/or oxidized lipid transport (e.g., oxLDL uptake) in various roles of CD36 such as those detailed in the Background section, including but not limited to the roles of CD36 in regulating the functions of and maintenance or survival (or death, as the case may be) of tumor cells, tumor-associated macrophages (TAMs), MDSCs, regulatory T cells and CD8 T cells.

Accordingly, it is contemplated that any of the compositions or formulations comprising an anti-CD36 antibody of the present disclosure can be used as therapeutics for treatment of diseases mediated by the function of CD36 in fatty acid transport, such as cancer. Further, it is contemplated that the anti-CD36 antibody of the present disclosure can be used as a therapeutic in combination with other therapeutics such as cellular therapies, cytokines and other biologics or drugs that modify the tumor micro-environment and/or increase immune response, antibody-drug conjugates, antibodies that modulate immune cells, and/or antibodies that target immune checkpoint molecules including, but not limited to, PD1, PD-L1, LAG3, CTLA-4, A2AR, TIM-3, BTLA, CD276, CD328, VTCN1, IDO, KIR, NOX2, VISTA, OX40, CD27, CD28, CD40, CD122, CD137, GITR, ICOS.

Overview of Terminology and Techniques

For the descriptions herein and the appended claims, the singular forms "a", and "an" include plural referents unless the context clearly indicates otherwise. Thus, for example, reference to "a protein" includes more than one protein, and reference to "a compound" refers to more than one compound. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. The use of "comprise," "comprises," "comprising" "include," "includes," and "including" are interchangeable and not intended to be limiting. It is to be further understood that where descriptions of various embodiments use the term "comprising," those skilled in the art would understand that in some specific instances, an embodiment can be alternatively described using language "consisting essentially of" or "consisting of."

Where a range of values is provided, unless the context clearly dictates otherwise, it is understood that each intervening integer of the value, and each tenth of each intervening integer of the value, unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding (i) either or (ii) both of those included limits are also included in the invention. For example, "1 to 50," includes "2 to 25," "5 to 20," "25 to 50," "1 to 10," etc.

Generally, the nomenclature used herein and the techniques and procedures described herein include those that are well understood and commonly employed by those of ordinary skill in the art, such as the common techniques and methodologies described in Sambrook et al., *Molecular Cloning—A Laboratory Manual* (2nd Ed.), Vols. 1-3, Cold Spring Harbor Laboratory, Cold Spring Harbor, N.Y., 1989 (hereinafter "Sambrook"); *Current Protocols in Molecular Biology*, F. M. Ausubel et al., eds., Current Protocols, a joint venture between Greene Publishing Associates, Inc. and John Wiley & Sons, Inc. (supplemented through 2011) (hereinafter "Ausubel"); *Antibody Engineering*, Vols. 1 and 2, R. Kontermann and S. Dubel, eds., Springer-Verlag, Berlin and Heidelberg (2010); *Monoclonal Antibodies: Methods and Protocols*, V. Ossipow and N. Fischer, eds., 2nd Ed., Humana Press (2014); *Therapeutic Antibodies: From Bench to Clinic*, Z. An, ed., J. Wiley & Sons, Hoboken, N.J. (2009); and *Phage Display*, Tim Clackson and Henry B. Lowman, eds., Oxford University Press, United Kingdom (2004).

All publications, patents, patent applications, and other documents referenced in this disclosure are hereby incorporated by reference in their entireties for all purposes to the same extent as if each individual publication, patent, patent application or other document were individually indicated to be incorporated by reference herein for all purposes.

Unless defined otherwise, all technical and scientific terms used herein have the same meaning as commonly understood by one of ordinary skill in the art to which the present invention pertains. It is to be understood that the terminology used herein is for the purpose of describing particular embodiments only and is not intended to be limiting. For purposes of interpreting this disclosure, the following description of terms will apply and, where appropriate, a term used in the singular form will also include the plural form and vice versa.

“CD36,” as used herein, refers to the CD36 protein, and as used herein encompasses the CD36 proteins of human, cynomolgus monkey, mouse, and any isoforms of these proteins. Amino acid sequences of various exemplary CD36 proteins are known in the art and are provided in Table 1 below and the attached Sequence Listing.

“CD36 mediated condition” or “CD36 mediated disease,” as used herein, encompasses any medical condition associated with the specific binding of ligands to the cell surface protein CD36. For example, specific binding by CD36 of lipids and/or fatty acids acts to regulate or increase the immuno-suppressive capacity of TAMs and regulatory T cells in the tumor microenvironment. Accordingly, CD36 mediated diseases can include, but are not limited to, any disease or condition mediated by and/or responsive to antagonists or inhibitors of CD36, including but not limited to cancers.

“Antibody,” as used herein, refers to a molecule comprising one or more polypeptide chains that specifically binds to, or is immunologically reactive with, a particular antigen. Exemplary antibodies of the present disclosure include monoclonal antibodies, polyclonal antibodies, chimeric antibodies, humanized antibodies, human antibodies, antibody fusions (e.g., fusion proteins), multispecific antibodies (e.g., bispecific antibodies), monovalent antibodies (e.g., single-arm antibodies), multivalent antibodies, antigen-binding fragments (e.g., Fab', $F(ab')_2$, Fab, Fv, rIgG, and scFv fragments), and synthetic antibodies (or antibody mimetics).

“Anti-CD36 antibody” or “antibody that binds CD36” refers to an antibody that binds CD36 with sufficient affinity such that the antibody is useful as a therapeutic and/or diagnostic agent for targeting CD36. In some embodiments, the extent of binding of an anti-CD36 specific antibody to an unrelated, non-CD36 antigen is less than about 20%, less than about 15%, less than about 10%, or less than about 5% of the binding of the antibody to CD36 as measured by, e.g., radioimmunoassay (RIA) or surface plasmon resonance (SPR). In some embodiments, an anti-CD36 antibody of the present disclosure has a dissociation constant ($K_D$) of <1 μM, <100 nM, <10 nM, <1 nM, <0.1 nM, <0.01 nM, or <1 pM (e.g., $10^{-8}$ M or less, e.g., from $10^{-8}$ M to $10^{-13}$ M, e.g., from $10^{-9}$ M to $10^{-13}$ M). Amino acid sequences of exemplary CD36 proteins of the present disclosure are provided in Table 2 below and the attached Sequence Listing.

“Full-length antibody,” “intact antibody,” or “whole antibody” are used herein interchangeably to refer to an antibody having a structure substantially similar to a native antibody structure or having heavy chains that contain an Fc region as defined herein.

“Antibody fusion” refers to an antibody that is covalently conjugated (or fused) to a polypeptide or protein, typically via a linker to a terminus of the antibody’s light chain (LC) or heavy chain (HC). Exemplary antibody fusions contemplated by the present disclosure can include an anti-CD36 antibody fused via a linker to a protein that is a T-cell activating or immunostimulatory cytokine, such as IL-2, IL-7, IL-10, IL-12, IL-15, IL-21, or IFN-α.

“Antibody fragment” refers to a portion of a full-length antibody which is capable of binding the same antigen as the full-length antibody. Examples of antibody fragments include, but are not limited to, Fv, Fab, Fab', Fab'-SH, $F(ab')_2$; diabodies; linear antibodies; monovalent, or single-armed antibodies; single-chain antibody molecules (e.g., scFv); and multispecific antibodies formed from antibody fragments.

“Class” of an antibody refers to the type of constant domain or constant region possessed by its heavy chain. There are five major classes of antibodies: IgA, IgD, IgE, IgG, and IgM, and several of these are further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively.

“Variable region” or “variable domain” refers to the domain of an antibody heavy or light chain that is involved in binding the antibody to antigen. The variable domains of the heavy chain and light chain ($V_H$ and $V_L$, respectively) of a native antibody generally have similar structures, with each domain comprising four conserved framework regions (FRs) and three hypervariable regions (HVRs) (see, e.g., Kindt et al., Kuby Immunology, $6^{th}$ ed., W.H. Freeman and Co., page 91). A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively (see, e.g., Portolano et al., J. Immunol. 150: 880-887 (1993); Clarkson et al., Nature 352:624-628 (1991)).

“Hypervariable region” or “HVR,” as used herein, refers to each of the regions of an antibody variable domain which are hypervariable in sequence and/or form structurally defined loops (“hypervariable loops”). Generally, native antibodies comprise four chains with six HVRs; three in the heavy chain variable domain, $V_H$ (HVR-H1, HVR-H2, HVR-H3), and three in the light chain variable domain, $V_L$ (HVR-L1, HVR-L2, HVR-L3). The HVRs generally comprise amino acid residues from the hypervariable loops and/or from the “complementarity determining regions” (CDRs). A number of hypervariable region delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk J. Mol. Biol. 196:901-917 (1987)). The AbM hypervariable regions represent a compromise between the Kabat CDRs and Chothia structural loops, and are used by Oxford Molecular’s AbM antibody modeling software. “Contact” hypervariable regions are based on an analysis of the available complex crystal structures. Residue ranges for hypervariable regions defined under these systems are noted in the table below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B[1] | H26-H35B[1] | H26-H32[1] | H30-H35B[1] |
| | H31-H35[2] | H26-H35[2] | H26-H32[2] | H30-H35[2] |
| H2 | H50-H65 | H50-H58 | H53-H55 | H47-H58 |
| H3 | H95-H102 | H95-H102 | H96-H101 | H93-H101 |

[1]Kabat numbering

[2]Chothia numbering

In addition to the systems described above, HVRs and CDRs can be identified using the international ImMunoGeneTics information system, referred to as IMGT/V-Quest, described in Brochet, X. et al., Nucl. Acids Res. 36, W503-508 (2008). PMID: 18503082; and available for use online at www.imgt.org/IMGT_vquest/input. IMGT/V-Quest analyzes alignments to closest germline V gene variable region nucleotide sequences using IMGT unique numbering to identify HVRs and CDRs.

Hypervariable regions (HVRs), as used herein, may include extended or alternative hypervariable regions as follows: 27-32, 27-36, 24-34, or 24-38 (HVR-L1); 50-52, 54-56, 50-56 or 54-60 (HVR-L2); 89-97 or 93-101 (HVR-L3); 26-33, 26-35, or 31-35 (HVR-H1); 51-58, 50-61, or 50-66 (H2); and 97-110, 97-112, 99-110, or 99-112 (H3) in the $V_H$ domain. The variable domain residues are numbered according to Kabat et al., supra, for each of these definitions.

"Complementarity determining region," or "CDR," as used herein, refers to the regions within the HVRs of the variable domain which have the highest sequence variability and/or are involved in antigen recognition. Generally, native antibodies comprise four chains with six CDRs; three in the heavy chain variable domains, $V_H$ (CDR-H1, CDR-H2, CDR-H3), and three in the light chain variable domains, $V_L$ (CDR-L1, CDR-L2, CDR-L3). Exemplary CDRs occur at variable domain amino acid residue positions: 24-34, 27-32, 27-36, 24-38 (CDR-L1); 50-56, 50-52, 54-56, or 54-60 (CDR-L2); 89-97, or 93-101 (CDR-L3); 31-35, or 26-33 (CDR-H1), 50-66, or 51-58 (CDR-H2); and 99-112, 99-110, 97-112, or 97-110 (CDR-H3).

"Framework" or "FR" refers to variable domain residues other than the HVR residues. The FRs of a variable domain generally consist of four domains: FR1, FR2, FR3, and FR4. Accordingly, the HVR and FR sequences generally appear in the following sequence in $V_H$ (or $V_L$): FR1-H1(L1)-FR2-H2(L2)-FR3-H3(L3)-FR4.

Unless otherwise indicated, the positions of residues in the HVRs, CDRs, FRs, and other residues in the variable domain are numbered herein according to Kabat et al., supra.

"Native antibody" refers to a naturally occurring immunoglobulin molecule. For example, native IgG antibodies are heterotetrameric glycoproteins of about 150,000 Daltons, composed of two identical light chains and two identical heavy chains that are disulfide-bonded. From N- to C-terminus, each heavy chain has a variable region ($V_H$), also called a variable heavy domain or a heavy chain variable domain, followed by three constant domains (CH1, CH2, and CH3). Similarly, from N- to C-terminus, each light chain has a variable region ($V_L$), also called a variable light domain or a light chain variable domain, followed by a constant light (CL) domain. The light chain of an antibody may be assigned to one of two types, called kappa (κ) and lambda (λ), based on the amino acid sequence of its constant domain.

"Monoclonal antibody" as used herein refers to an antibody obtained from a substantially homogeneous population of antibodies, i.e., the individual antibodies comprising the population are identical and/or bind the same epitope, except for possible variant antibodies (e.g., variant antibodies contain mutations that occur naturally or arise during production of a monoclonal antibody, and generally are present in minor amounts). In contrast to polyclonal antibody preparations, which typically include different antibodies directed against different determinants (epitopes), each monoclonal antibody of a monoclonal antibody preparation is directed against a single determinant on an antigen. Thus, the term "monoclonal" indicates the character of the antibody as being obtained from a substantially homogeneous population of antibodies and is not to be construed as requiring production of the antibody by any particular method. For example, the monoclonal antibodies to be used may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

"Chimeric antibody" refers to an antibody in which a portion of the heavy and/or light chain is derived from a particular source or species, while the remainder of the heavy and/or light chain is derived from a different source or species.

"Humanized antibody" refers to a chimeric antibody comprising amino acid sequences from non-human CDRs and amino acid sequences from human FRs. In certain embodiments, a humanized antibody will comprise substantially all of at least one, and typically two, variable domains, in which all or substantially all of the CDRs correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

"Human antibody" refers to an antibody which possesses an amino acid sequence corresponding to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

"Human consensus framework" is a framework which represents the most commonly occurring amino acid residues in a selection of human immunoglobulin $V_L$ or $V_H$ framework sequences. Generally, the selection of human immunoglobulin $V_L$ or $V_H$ sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda MD (1991), vols. 1-3. In one embodiment, for the $V_L$, the subgroup is subgroup kappa I as in Kabat et al., supra. In one embodiment, for the $V_H$, the subgroup is subgroup III as in Kabat et al., supra.

"Acceptor human framework" as used herein is a framework comprising the amino acid sequence of a light chain variable domain ($V_L$) framework or a heavy chain variable domain ($V_H$) framework derived from a human immunoglobulin framework or a human consensus framework. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the $V_L$ acceptor human framework is identical in sequence to the $V_L$ human immunoglobulin framework sequence or human consensus framework sequence.

"Fc region," refers to a dimer complex comprising the C-terminal polypeptide sequences of an immunoglobulin heavy chain, wherein a C-terminal polypeptide sequence is that which is obtainable by papain digestion of an intact antibody. The Fc region may comprise native or variant Fc sequences. Although the boundaries of the Fc sequence of an immunoglobulin heavy chain may vary, the human IgG heavy chain Fc sequence is usually defined to stretch from an amino acid residue at about position Cys226, or from about position Pro230, to the carboxyl-terminus of the Fc sequence. However, the C-terminal lysine (Lys447) of the Fc sequence may or may not be present. The Fc sequence of an immunoglobulin generally comprises two constant domains, a CH2 domain and a CH3 domain, and optionally comprises a CH4 domain.

"Fc receptor" or "FcR," refers to a receptor that binds to the Fc region of an antibody. In some embodiments, an FcR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain, (see, e.g., Daeron, Annu. Rev. Immunol. 15:203-234 (1997)). FcR, as used herein, also includes the neonatal receptor, FcRn, which is responsible for the transfer of maternal IgGs to the fetus (Guyer et al, J. Immunol. 1 17:587 (1976) and Kim et al, J. Immunol. 24:249 (1994)) and regulation of homeostasis of immunoglobulins. FcRs are reviewed, for example, in Ravetch and Kinet, Annu. Rev. Immunol 9:457-92 (1991); Capel et al, Immunomethods 4:25-34 (1994); and de Haas et al, J. Lab. Clin. Med. 126:330-41 (1995).

"Multispecific antibody" is an antibody having at least two different binding sites, each site with a different binding specificity. A multispecific antibody can be a full-length antibody or an antibody fragment, and the different binding sites may bind each to a different antigen or the different binding sites may bind to two different epitopes of the same antigen.

"Fv fragment" refers to an antibody fragment which contains a complete antigen recognition and binding site. This region consists of a dimer of one heavy and one light chain variable domain in tight association, which can be covalent in nature, for example in scFv. It is in this configuration that the three CDRs of each variable domain interact to define an antigen binding site on the surface of the $V_H$-$V_L$ dimer. Collectively, the six CDRs or a subset thereof confer antigen binding specificity to the antibody. However, even a single variable domain (or half of an Fv comprising only three CDRs specific for an antigen) has the ability to recognize and bind antigen, although usually at a lower affinity than the entire binding site.

"Fab fragment' refers to an antibody fragment that contains a variable and constant domain of the light chain and a variable domain and the first constant domain (CH1) of the heavy chain. "F(ab')$_2$ fragments" comprise a pair of Fab fragments which are generally covalently linked near their carboxy termini by hinge cysteines between them. Other chemical couplings of antibody fragments also are known in the art.

"Antigen binding arm," as used herein, refers to a component of an antibody that has an ability to specifically bind a target molecule of interest. Typically, the antigen binding arm is a complex of immunoglobulin polypeptide sequences, e.g., CDR and/or variable domain sequences of an immunoglobulin light and heavy chain.

"Single-chain Fv" or "scFv" refer to antibody fragments comprising the $V_H$ and $V_L$ domains of an antibody, wherein these domains are present in a single polypeptide chain. Generally, an Fv polypeptide further comprises a polypeptide linker between the $V_H$ and $V_L$ domains which enables the scFv to form the desired antigen binding structure.

"Affinity" refers to the strength of the sum total of noncovalent interactions between a single binding site of a molecule (e.g., an antibody) and its binding partner (e.g., an antigen). "Binding affinity" refers to intrinsic binding affinity which reflects a 1:1 interaction between members of a binding pair (e.g., antibody and antigen). The affinity of a molecule X for its partner Y can generally be represented by the equilibrium dissociation constant ($K_D$). Affinity can be measured by common methods known in the art, including those described herein. Specific illustrative and exemplary embodiments for measuring binding affinity are described in the following.

"Binds specifically" or "specific binding" refers to binding of an antibody to an antigen with an affinity value of no more than about $1\times10^{-7}$ M. In some embodiments, an antibody may have a secondary affinity for an antigen other than the antigen to which it binds specifically, where "secondary affinity" will generally refer to binding of an antibody to a secondary antigen with an affinity value of more than about 10 nM as described elsewhere herein. Where an antibody may have a secondary affinity for a secondary antigen, such an antibody will nevertheless bind specifically to the primary antigen.

"Isolated antibody" refers to an antibody which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic methods (e.g., ion exchange or reverse phase HPLC). For review of methods for assessment of antibody purity, see, e.g., Flatman et al., J. Chromatogr. B 848:79-87.

"Effector function" refer to a biological activity attributed to the Fc region of an antibody, which varies with the antibody isotype. Examples of antibody effector functions include: Clq binding and complement dependent cytotoxicity (CDC); Fc receptor binding; antibody-dependent cell-mediated cytotoxicity (ADCC); phagocytosis; down regulation of cell surface receptors (e.g., B cell receptor); and B cell activation.

"Immunoconjugate" refers to an antibody conjugated to one or more heterologous molecule(s), including but not limited to a cytotoxic agent.

"Treatment," "treat" or "treating" refers to clinical intervention in an attempt to alter the natural course of a disorder in the individual being treated, and can be performed either for prophylaxis or during the course of clinical pathology. Desired results of treatment can include, but are not limited to, preventing occurrence or recurrence of the disorder, alleviation of symptoms, diminishment of any direct or indirect pathological consequences of the disorder, preventing metastasis, decreasing the rate of progression, amelioration or palliation of a disease state, and remission or improved prognosis. For example, treatment can include administration of a therapeutically effective amount of pharmaceutical formulation comprising an anti-CD36 antibody to a subject to delay development or slow progression of a disease or condition mediated by CD36 and/or its binding to ligands, or a disease or condition in which CD36 may play a role in the pathogenesis and/or progression.

"Pharmaceutical formulation" refers to a preparation in a form that allows the biological activity of the active ingredient(s) to be effective, and which contain no additional components which are toxic to the subjects to which the formulation is administered. A pharmaceutical formulation may include one or more active agents. For example, a pharmaceutical formulation may include an anti-CD36 antibody as the sole active agent of the formulation or may include an anti-CD36 antibody and one or more additional active agents, such as an inhibitor of an immune checkpoint molecule.

"Sole active agent," as used herein, refers an active agent in a pharmaceutical formulation that is the only active agent present in that formulation that provides, or would be expected to provide, the relevant pharmacological effect to treat the subject for the condition being treated. A pharmaceutical formulation comprising a sole active agent does not exclude the presence of one or more non-active agents, such as e.g., a pharmaceutically acceptable carrier, in the formulation. A "non-active agent" is an agent that would not be expected to provide, or otherwise significantly contribute to, the relevant pharmacological effect intended to treat the subject for the condition.

"Pharmaceutically acceptable carrier" refers to an ingredient in a pharmaceutical formulation, other than an active ingredient, which is nontoxic to the subject to whom it is administered. A pharmaceutically acceptable carrier includes, but is not limited to, a buffer, excipient, stabilizer, or preservative.

"Immune checkpoint molecule," as used herein, refers to a molecule that functions to regulate an immune system pathway and thereby prevent it from attacking cells unnecessarily. Many immune checkpoint molecules, both inhibitory and co-stimulatory, are targets for immunotherapy (e.g., with blocking antibodies to block immune inhibition or with agonists to promote immune stimulation) in the treatment of cancer and viral infections. Exemplary immune checkpoint molecules targeted for cancer immunotherapy include, but are not limited to, PD1, PD-L1, LAG3, CTLA-4, A2AR, TIM-3, BTLA, CD276, CD328, VTCN1, IDO, KIR, NOX2, VISTA, OX40, CD27, CD28, CD40, CD122, CD137, GITR, ICOS.

"Therapeutically effective amount" refers to the amount of an active ingredient or agent (e.g., a pharmaceutical formulation) to achieve a desired therapeutic or prophylactic result, e.g., to treat or prevent a disease, disorder, or condition in a subject. In the case of a CD36 mediated disease or condition, the therapeutically effective amount of the therapeutic agent is an amount that reduces, prevents, inhibits, and/or relieves to some extent one or more of the symptoms associated with the disease, disorder, or condition. For cancer therapy, efficacy in vivo can, for example, be measured by assessing the growth of a primary tumor, occurrence and/or growth of secondary tumor(s), occurrence and/or number of metastases, duration, severity, and/or recurrence of symptoms, the response rate (RR), duration of response, and/or quality of life.

"Concurrently," as used herein, refers to administration of two or more therapeutic agents, where at least part of the administration overlaps in time. Accordingly, concurrent administration includes a dosing regimen when the administration of one or more agent(s) continues after discontinuing the administration of one or more other agent(s).

"Individual" or "subject" refers to a mammal, including but not limited to, domesticated animals (e.g., cows, sheep, cats, dogs, and horses), primates (e.g., humans and non-human primates such as monkeys), rabbits, and rodents (e.g., mice and rats).

Detailed Description of Various Embodiments

I. CD36

CD36 is a multifunctional transmembrane glycoprotein that acts as a cell surface receptor for a broad range of ligands. Generally, CD36 has two distinct binding domains for binding of thrombospondin versus other ligands of a lipidic nature, such as oxidized low-density lipoprotein (oxLDL), anionic phospholipids, long-chain fatty acids and bacterial diacylated lipopeptides. The cellular responses mediated by CD36 binding of these ligands are believed to include fatty acid metabolism, dietary fat processing, angiogenesis, and inflammatory response. CD36 acts as a coreceptor for the TLR4:TLR6 heterodimer, and thereby promotes inflammation in monocytes/macrophages. It is believed that CD36, upon binding a ligand, such as oxidized LDL ("oxLDL"), interacts with the TLR4:TLR6 heterodimer, and the complex is internalized thereby triggering an inflammatory response that leads to NF-kappa-B-dependent production of CXCL1, CXCL2 and CCL9 cytokines, via MyD88 signaling pathway, and CCL5 cytokine, via TICAM1 signaling pathway, as well as IL1B secretion, through the priming and activation of the NLRP3 inflammasome. Other CD36-interacting co-receptors have also been described.

The sequence and annotation of human CD36 (also referred to herein as "hCD36") can be found at UniProt entry P16671, and the full-length 472 amino acid sequence of Isoform 1 is set forth herein as SEQ ID NO: 58. The sequence and annotation of murine CD36 (also referred to herein as "mCD36") can be found at UniProt entry Q08857, and the full-length 472 amino acid sequence is set forth herein as SEQ ID NO:60. Table 1 below provides a summary description of the sequences of the human and mouse CD36 polypeptides used in the present disclosure, and their sequence identifiers. The sequences also are included in the accompanying Sequence Listing.

TABLE 1

Human and mouse CD36 polypeptides

| Name | Sequence | SEQ ID NO: |
|---|---|---|
| hCD36 (isoform 1) UniProt P16671 | MGCDRNCGLIAGAVIGAVLAVFGGILMPVGDLLIQKTIKKQVVLEEGTIAF KNWVKTGTEVYRQFWIFDVQNPQEVMMNSSNIQVKQRGPYTYRVRFLAKEN VTQDAEDNTVSFLQPNGAIFEPSLSVGTEADNFTVLNLAVAAASHIYQNQF VQMILNSLINKSKSSMFQVRTLRELLWGYRDPFLSLVPYPVTTTVGLFYPY NNTADGVYKVENGKDNISKVAIIDTYKGKRNLSYWESHCDMINGTDAASFP | 58 |

TABLE 1-continued

| Human and mouse CD36 polypeptides | | |
|---|---|---|
| Name | Sequence | SEQ ID NO: |
| | PFVEKSQVLQFFSSDICRSIYAVFESDVNLKGIPVYRFVLPSKAFASPVEN<br>PDNYCFCTEKIISKNCTSYGVLDISKCKEGRPVYISLPHFLYASPDVSEPI<br>DGLNPNEEEHRTYLDIEPITGFTLQFAKRLQVNLLVKPSEKIQVLKNLKRN<br>YIVPILWLNETGTIGDEKANMFRSQVTGKINLLGLIEMILLSVGVVMFVAF<br>MISYCACRSKTIK | |
| hCD36.ECD | GDLLIQKTIKKQVVLEEGTIAFKNWVKTGTEVYRQFWIFDVQNPQEVMMNS<br>SNIQVKQRGPYTYRVRFLAKENVTQDAEDNTVSFLQPNGAIFEPSLSVGTE<br>ADNFTVLNLAVAAASHIYQNQFVQMILNSLINKSKSSMFQVRTLRELLWGY<br>RDPFLSLVPYPVTTTVGLFYPYNNTADGVYKVENGKDNISKVAIIDTYKGK<br>RNLSYWESHCDMINGTDAASFPPFVEKSQVLQFFSSDICRSIYAVFESDVN<br>LKGIPVYRFVLPSKAFASPVENPDNYCFCTEKIISKNCTSYGVLDISKCKE<br>GRPVYISLPHFLYASPDVSEPIDGLNPNEEEHRTYLDIEPITGFTLQFAKR<br>LQVNLLVKPSEKIQVLKNLKRNYIVPILWLNETGTIGDEKANMFRSQVTGK<br>IN | 59 |
| mCD36<br>UniProt<br>Q08857 | MGCDRNCGLIAGAVIGAVLAVFGGILMPVGDMLIEKTIKREVVLEEGTTAF<br>KNWVKTGTTVYRQFWIFDVQNPDDVAKNSSKIKVKQRGPYTYRVRYLAKEN<br>ITQDPEDHTVSFVQPNGAIFEPSLSVGTEDDNFTVLNLAVAAAPHIYQNSF<br>VQVVLNSLIKKSKSSMFQTRSLKELLWGYKDPFLSLVPYPISTTVGVFYPY<br>NDTVDGVYKVENGKDNISKVAIIESYKGKRNLSYWPSYCDMINGTDAASFP<br>PFVEKSRTLRFFSSDICRSIYAVFGSEIDLKGIPVYRFVLPANAFASPLQN<br>PDNHCFCTEKVISNNCTSYGVLDIGKCKEGKPVYISLPHFLHASPDVSEPI<br>EGLHPNEDEHRTYLDVEPITGFTLQFAKRLQVNILVKPARKIEALKNLKRP<br>YIVPILWLNETGTIGDEKAEMFKTQVTGKIKLLGMVEMALLGIGVVMFVAF<br>MISYCACKSKNGK | 60 |
| mCD36.ECD | GDMLIEKTIKREVVLEEGTTAFKNWVKTGTTVYRQFWIFDVQNPDDVAKNS<br>SKIKVKQRGPYTYRVRYLAKENITQDPEDHTVSFVQPNGAIFEPSLSVGTE<br>DDNFTVLNLAVAAAPHIYQNSFVQVVLNSLIKKSKSSMFQTRSLKELLWGY<br>KDPFLSLVPYPISTTVGVFYPYNDTVDGVYKVENGKDNISKVAIIESYKGK<br>RNLSYWPSYCDMINGTDAASFPPFVEKSRTLRFFSSDICRSIYAVFGSEID<br>LKGIPVYRFVLPANAFASPLQNPDNHCFCTEKVISNNCTSYGVLDIGKCKE<br>GKPVYISLPHFLHASPDVSEPIEGLHPNEDEHRTYLDVEPITGFTLQFAKR<br>LQVNILVKPARKIEALKNLKRPYIVPILWLNETGTIGDEKAEM<br>FKTQVTGKIK | 61 |
| Rhesus CD36<br>NP_<br>001028085.1 | MGCDRNCGLITGAVIGAVLAVFGGILMPVGDMLIQKTIKKEVVLEEGTIAF<br>KNWVKTGTEIYRQFWIFDVQNPQEVMMNSSNIQVKQRGPYTYRVRFLAKEN<br>ITQDPKDNTVSFLQPNGAIFEPSLSVGTEADNFTVLNLAVAAASHIYPNPF<br>VQVVLNSLINKSKSSMFQVRTLRELLWGYTDPFLSLVPYPVSTRVGMFYPY<br>NNTADGVYKVFNGKDSISKVAIIDTYKGKRNLSYWESYCDMINGTDAASFP<br>PFVEKSQVLQFFSSDICRSIYAVFESDVNLKGIPVYRFVLPSKAFASPVQN<br>PDNHCFCTEKIISKNCTSYGVLDISKCKEGKPVYISLPHFLYASPDVSETI<br>DGLNPNEEEHRTYLDIEPITGFTLQFAKRLQVNLLVKPSNKIQVLKRLKRN<br>YIVPILWLNETGTIGDEKAKMFRSQVTGKINLLGLIEMILLSVGVVMFVAF<br>MISYCACRSKTIK | 62 |
| Rhesus<br>CD36.ECD | GDMLIQKTIKKEVVLEEGTIAFKNWVKTGTEIYRQFWIFDVQNPQEVMMNS<br>SNIQVKQRGPYTYRVRFLAKENITQDPKDNTVSFLQPNGAIFEPSLSVGTE<br>ADNFTVLNLAVAAASHIYPNPFVQVVLNSLINKSKSSMFQVRTLRELLWGY<br>TDPFLSLVPYPVSTRVGMFYPYNNTADGVYKVENGKDSISKVAIIDTYKGK<br>RNLSYWESYCDMINGTDAASFPPFVEKSQVLQFFSSDICRSIYAVFESDVN<br>LKGIPVYRFVLPSKAFASPVQNPDNHCFCTEKIISKNCTSYGVLDISKCKE<br>GKPVYISLPHFLYASPDVSETIDGLNPNEEEHRTYLDIEPITGFTLQFAKR<br>LQVNLLVKPSNKIQVLKRLKRNYIVPILWLNETGTIGDEKAKMFRSQVTGK<br>IN | 63 |

II. Anti-CD36 Antibodies

In some embodiments, the present disclosure provides structures of anti-CD36 antibodies in terms of the amino acid and encoding nucleotide sequences of the various well-known immunoglobulin features (e.g., CDRs, FRs, $V_H$, $V_L$ domains, and full-length heavy and light chains). Table 2 below provides a summary description of the anti-CD36 antibodies of the presented disclosure as generated and functionally characterized as described in the Examples. The relevant sequences and sequence identifiers for each of the antibodies are provided in Table 2 and also included in the accompanying Sequence Listing.

TABLE 2

| Anti-CD36 antibody sequences | | |
|---|---|---|
| Description | Sequence | SEQ ID NO: |
| 12P109-scFv<br>(DNA) | ATGGCCGATATTCAAATGACCCAGAGCCCGAGCAGCCTGAGCG<br>CGAGCGTGGGAGATCGCGTGACCATTACCTGCCGTGCGAGCCA<br>GGATGTTAGCAACTGGGTCGCATGGTATCAGCAGAAACCAGGC<br>AAAGCGCCGAAACTTCTGATATCTACCTCCACTAGCCTGTATA<br>GCGGCGTGCCGTCGCGTTTTTCGGGCAGTGGCAGCGGCACGGA<br>CTTTACCCTGACGATATCTTCCTTACAACCGGAGGATTTTGCG<br>ACCTACTACTGTCAACAGTACTACACCTTGCCGTTCACCTTCG<br>GTCAAGGCACCAAAGTGGAAATCAAACGCGGTGGTTCCTCTAG<br>ATCTTCCACCTCTGGTGGCGGTGGCTCGGGCGGTGGTGGGGAA<br>GTGCAGCTGGTGGAATCGGGAGGCGGTCTGGTGCAACCTGGCG<br>GCAGCCTTCGTCTGAGCTGTGCGGCGAGCGGGTTCACCATTAG<br>CAGCTTTGGGATTCATTGGGTGCGTCAAGCTCCCGGCAAGGGG<br>CTGGAGTGGGTCGCGTGGATTGCTCCCTACGGTGGTTACACAT<br>ACTATGCCGACAGCGTGAAAGGTCGCTTTACGATTAGTGCGGA<br>CACCAGCAAAAATACCGCGTACCTGCAGATGAATAGCCTGCGT<br>GCGGAAGACACAGCGGTGTATTATTGCGCGCGTTCGTTTTTCG<br>GGTACTTCGATTATTGGGGGCAGGGCACCCTTGTTACCGTGAG<br>CTCGGCGTCAGCGGCCGCA | 1 |
| 12P109-$V_H$<br>A8A-$V_H$<br>A8A-N52T-$V_H$<br>117-$V_H$ | EVQLVESGGGLVQPGGSLRLSCAASGFTISSFGIHWVRQAPGK<br>GLEWVAWIAPYGGYTYYADSVKGRFTISADTSKNTAYLQMNSL<br>RAEDTAVYYCARSFFGYFDYWGQGTLVTVSS | 2 |
| 12P109-CDR-H1<br>A8A-CDR-H1<br>A8A-N52T-CDR-H1<br>117-CDR-H1<br>117_57D-CDR-H1<br>117_57E-CDR-H1<br>117_57DE-CDR-H1<br>117_57EE-CDR-H1 | AASGFTISSFGIH | 3 |
| 12P109-CDR-H2<br>A8A-CDR-H2<br>A8A-N52T-CDR-H2<br>117-CDR-H2<br>117_30AA-CDR-H2<br>117_30DA-CDR-H2 | WIAPYGGYTY | 4 |
| 12P109-CDR-H3<br>A8A-CDR-H3<br>A8A-N52T-CDR-H3<br>117-CDR-H3<br>117_30AA-CDR-H3<br>117_30DA-CDR-H3<br>117_30DE-CDR-H3<br>117_57D-CDR-H3<br>117_57E-CDR-H3<br>117_57DE-CDR-H3<br>117_57EE-CDR-H3<br>117_DA57E-CDR-H3 | ARSFFGYFDY | 5 |
| 12P109-VL | DIQMTQSPSSLSASVGDRVTITCRASQDVSNWVAWYQQKPGKA<br>PKLLISTSTSLYSGVPSRFSGSGSGTDFTLTISSLQPEDFATY<br>YCQQYYTLPFTFGQGTKVEIKR | 6 |
| 12P109-CDR-L1<br>A8A-CDR-L1<br>A8A-N52T-CDR-L1<br>117-CDR-L1<br>117_30AA-CDR-L1<br>117_30DA-CDR-L1<br>117_30DE-CDR-L1<br>117_57D-CDR-L1<br>117_57E-CDR-L1<br>117_57DE-CDR-L1<br>117_57EE-CDR-L1<br>117_DA57E-CDR-L1 | RASQDVSNWVA | 7 |
| 12P109-CDR-L2 | STSTSLYS | 8 |
| 12P109-CDR-L3 | YYTLPFTF | 9 |

TABLE 2-continued

| Anti-CD36 antibody sequences | | |
|---|---|---|
| Description | Sequence | SEQ ID NO: |
| A8A-scFv (DNA) | ATGGCCGATATTCAAATGACCCAGAGCCCGAGCAGCCTGAGCG<br>CGAGCGTGGGAGATCGCGTGACCATTACCTGCCGTGCGAGCCA<br>GGATGTTAGTAATTGGGTCGCATGGTATCAGCAGAAACCAGGC<br>AAAGCGCCGAAACTTCTGATATCCTATGCCAACAGCCTGTATA<br>GCGGCGTGCCGTCGCGTTTTTCGGGCAGTGGCAGCGGCACGGA<br>CTTTACCCTGACGATATCTTCCTTACAACCGGAGGATTTTGCG<br>ACCTACTACTGTCAACAGCACTCTAACCTTCCGCTGACCTTCG<br>GTCAAGGCACCAAAGTGGAAATCAAACGTGGTGGTTCCTCTAG<br>ATCTTCCTCCTCTGGTGGCGGTGGCTCGGGCGGTGGTGGGGAA<br>GTGCAGCTGGTGGAATCGGGAGGCGGTCTGGTGCAACCTGGCG<br>GCAGCCTTCGTCTGAGCTGTGCGGCGAGCGGGTTCACCATTAG<br>CAGCTTTGGGATTCATTGGGTGCGTCAAGCTCCCGGCAAGGGG<br>CTGGAGTGGGTCGCGTGGATTGCTCCCTACGGTGGTTACACAT<br>ACTATGCCGACAGCGTGAAAGGTCGCTTTACGATTAGTGCGGA<br>CACCAGCAAAAATACCGCGTACCTGCAGATGAATAGCCTGCGT<br>GCGGAAGACACAGCGGTGTATTATTGCGCGCGTTCGTTTTTCG<br>GGTACTTCGATTATTGGGGGCAGGGCACCCTTGTTACCGTGAG<br>CTCGGCGTCAGCGGCCGCA | 10 |
| A8A-$V_L$ | DIQMTQSPSSLSASVGDRVTITCRASQDVSNWVAWYQQKPGKA<br>PKLLISYANSLYSGVPSRFSGSGSGTDFTLTISSLQPEDFATY<br>YCQQHSNLPLTFGQGTKVEIKR | 11 |
| A8A-CDR-L2 | SYANSLYS | 12 |
| A8A-CDR-L3<br>A8A-N52T-CDR-L3 | HSNLPLTF | 13 |
| A8A-N52T-$V_L$ | DIQMTQSPSSLSASVGDRVTITCRASQDVSNWVAWYQQKPGKA<br>PKLLISYA**T**SLYSGVPSRFSGSGSGTDFTLTISSLQPEDFATY<br>YCQQHSNLPLTFGQGTKVEIKR | 14 |
| A8A-N52T-CDR-L2<br>117-CDR-L2<br>117_30AA-CDR-L2<br>117_30DA-CDR-L2<br>117_30DE-CDR-L2<br>117_57D-CDR-L2<br>117_57E-CDR-L2<br>117_57DE-CDR-L2<br>117_57EE-CDR-L2<br>117_DA57E-CDR-L2 | SYA**T**SLYS | 15 |
| 117-scFv (DNA) | ATGGCCGATATTCAAATGACCCAGAGCCCGAGCAGCCTGAGCG<br>CGAGCGTGGGAGATCGCGTGACCATTACCTGCCGTGCGAGCCA<br>GGATGTTAGTAATTGGGTCGCATGGTATCAGCAGAAACCAGGC<br>AAAGCGCCGAAACTTCTGATATCCTATGCTACTAGCCTGTATA<br>GCGGCGTGCCGTCGCGTTTTTCGGGCAGTGGCAGCGGCACGGA<br>CTTTACCCTGACGATATCTTCCTTACAACCGGAGGATTTTGCG<br>ACCTACTACTGTCAACAGCACTCTAACGCGCCGCTGACCTTCG<br>GTCAAGGCACCAAAGTGGAAATCAAACGCGGTGGTTCCTCTAG<br>ATCTTCCTCCTCTGGTGGCGGTGGCTCGGGCGGTGGTGGGGAA<br>GTGCAGCTGGTGGAATCGGGAGGCGGTCTGGTGCAACCTGGCG<br>GCAGCCTTCGTCTGAGCTGTGCGGCGAGCGGGTTCACCATTAG<br>CAGCTTTGGGATTCATTGGGTGCGTCAAGCTCCCGGCAAGGGG<br>CTGGAGTGGGTCGCGTGGATTGCTCCCTACGGTGGTTACACAT<br>ACTATGCCGACAGCGTGAAAGGTCGCTTTACGATTAGTGCGGA<br>CACCAGCAAAAATACCGCGTACCTGCAGATGAATAGCCTGCGT<br>GCGGAAGACACAGCGGTGTATTATTGCGCGCGTTCGTTTTTCG<br>GGTACTTCGATTATTGGGGGCAGGGCACCCTTGTTACCGTGAG<br>CTCGGCGTCAGCGGCCGCA | 16 |
| 117-$V_L$<br>117_30AA-$V_L$<br>117_30DA-$V_L$<br>117_30DE-$V_L$<br>117_57D-$V_L$<br>117_57E-$V_L$<br>117_57DE-$V_L$<br>117_57EE-$V_L$<br>117_DA57E-$V_L$ | DIQMTQSPSSLSASVGDRVTITCRASQDVSNWVAWYQQKPGKA<br>PKLLISYATSLYSGVPSRFSGSGSGTDFTLTISSLQPEDFATY<br>YCQQHSNAPLTFGQGTKVEIKR | 17 |

TABLE 2-continued

Anti-CD36 antibody sequences

| Description | Sequence | SEQ ID NO: |
|---|---|---|
| 117-CDR-L3<br>117_30AA-CDR-L3<br>117_30DA-CDR-L3<br>117_30DE-CDR-L3<br>117_57D-CDR-L3<br>117_57E-CDR-L3<br>117_57DE-CDR-L3<br>117_57EE-CDR-L3<br>117_DA57E-CDR-L3 | HSNAPLTF | 18 |
| 117_30AA<br>(HC-DNA) | ATGGCCGATATTCAAATGACCCAGAGCCCGAGCAGCCTGAGCG<br>CGAGCGTGGGAGATCGCGTGACCATTACCTGCCGTGCGAGCCA<br>GGATGTTAGTAATTGGGTCGCATGGTATCAGCAGAAACCAGGC<br>AAAGCGCCGAAACTTCTGATATCCTATGCTACTAGCCTGTATA<br>GCGGCGTGCCGTCGCGTTTTTCGGGCAGTGGCAGCGGCACGGA<br>CTTTACCCTGACGATATCTTCCTTACAACCGGAGGATTTTGCG<br>ACCTACTACTGTCAACAGCACTCTAACGCGCCGCTGACCTTCG<br>GTCAAGGCACCAAAGTGGAAATCAAACGCGGTGGTTCCTCTAG<br>ATCTTCCTCCTCTGGTGGCGGTGGCTCGGGCGGTGGTGGGGAA<br>GTGCAGCTGGTGGAATCGGGAGGCGGTCTGGTGCAACCTGGCG<br>GCAGCCTTCGTCTGAGCTGTGCGGCGAGCGGGTTCACCATTGC<br>CGCCTTTGGGATTCATTGGGTGCGTCAAGCTCCCGGCAAGGGG<br>CTGGAGTGGGTCGCGTGGATTGCTCCCTACGGTGGTTACACAT<br>ACTATGCCGACAGCGTGAAAGGTCGCTTTACGATTAGTGCGGA<br>CACCAGCAAAAATACCGCGTACCTGCAGATGAATAGCCTGCGT<br>GCGGAAGACACAGCGGTGTATTATTGCGCGCGTTCGTTTTTCG<br>GGTACTTCGATTATTGGGGGCAGGGCACCCTTGTTACCGTGAG<br>CTCGGCGTCAGCGGCCGCA | 19 |
| 117_30AA-$V_H$ | EVQLVESGGGLVQPGGSLRLSCAASGFTIAAFGIHWVRQAPGK<br>GLEWVAWIAPYGGYTYYADSVKGRFTISADTSKNTAYLQMNSL<br>RAEDTAVYYCARSFFGYFDYWGQGTLVTVSS | 20 |
| 117_30AA-CDR-H1 | AASGFTIAAFGIH | 21 |
| 117_30DA-scFv<br>(DNA) | ATGGCCGATATTCAAATGACCCAGAGCCCGAGCAGCCTGAGCG<br>CGAGCGTGGGAGATCGCGTGACCATTACCTGCCGTGCGAGCCA<br>GGATGTTAGTAATTGGGTCGCATGGTATCAGCAGAAACCAGGC<br>AAAGCGCCGAAACTTCTGATATCCTATGCTACTAGCCTGTATA<br>GCGGCGTGCCGTCGCGTTTTTCGGGCAGTGGCAGCGGCACGGA<br>CTTTACCCTGACGATATCTTCCTTACAACCGGAGGATTTTGCG<br>ACCTACTACTGTCAACAGCACTCTAACGCGCCGCTGACCTTCG<br>GTCAAGGCACCAAAGTGGAAATCAAACGCGGTGGTTCCTCTAG<br>ATCTTCCTCCTCTGGTGGCGGTGGCTCGGGCGGTGGTGGGGAA<br>GTGCAGCTGGTGGAATCGGGAGGCGGTCTGGTGCAACCTGGCG<br>GCAGCCTTCGTCTGAGCTGTGCGGCGAGCGGGTTCACCATTGA<br>CGCCTTTGGGATTCATTGGGTGCGTCAAGCTCCCGGCAAGGGG<br>CTGGAGTGGGTCGCGTGGATTGCTCCCTACGGTGGTTACACAT<br>ACTATGCCGACAGCGTGAAAGGTCGCTTTACGATTAGTGCGGA<br>CACCAGCAAAAATACCGCGTACCTGCAGATGAATAGCCTGCGT<br>GCGGAAGACACAGCGGTGTATTATTGCGCGCGTTCGTTTTTCG<br>GGTACTTCGATTATTGGGGGCAGGGCACCCTTGTTACCGTGAG<br>CTCGGCGTCAGCGGCCGCA | 22 |
| 117_30DA-$V_H$ | EVQLVESGGGLVQPGGSLRLSCAASGFTIDAFGIHWVRQAPGK<br>GLEWVAWIAPYGGYTYYADSVKGRFTISADTSKNTAYLQMNSL<br>RAEDTAVYYCARSFFGYFDYWGQGTLVTVSS | 23 |
| 117_30DA-CDR-H1<br>117_DA57E-CDR-H1 | AASGFTIDAFGIH | 24 |
| 117_30DE-$V_H$<br>(DNA) | GAAGTGCAGCTGGTGGAATCGGGAGGCGGTCTGGTGCAACCTG<br>GCGGCAGCCTTCGTCTGAGCTGTGCGGCGAGCGGGTTCACCAT<br>TGACAGCTTTGGGATTCATTGGGTGCGTCAAGCTCCCGGCAAG<br>GGGCTGGAGTGGGTCGCGTGGATTGCTCCCTACGGTGGTGAAA<br>CATACTATGCCGACAGCGTGAAAGGTCGCTTTACGATTAGTGC<br>GGACACCAGCAAAAATACCGCGTACCTGCAGATGAATAGCCTG<br>CGTGCGGAAGACACAGCGGTGTATTATTGCGCGCGTTCGTTTT<br>TCGGGTACTTCGATTATTGGGGGCAGGGCACCCTTGTTACCGT<br>GAGCTCG | 25 |

TABLE 2-continued

| Anti-CD36 antibody sequences | | |
|---|---|---|
| Description | Sequence | SEQ ID NO: |
| 117_30DE-$V_H$ | EVQLVESGGGLVQPGGSLRLSCAASGFTIDSFGIHWVRQAPGK<br>GLEWVAWIAPYGGETYYADSVKGRFTISADTSKNTAYLQMNSL<br>RAEDTAVYYCARSFFGYFDYWGQGTLVTVSS | 26 |
| 117_30DE-CDR-H1 | AASGFTIDSFGIH | 27 |
| 117_30DE-CDR-H2 | WIAPYGGETY | 28 |
| 117_57D-scFv (DNA) | ATGGCCGATATTCAAATGACCCAGAGCCCGAGCAGCCTGAGCG<br>CGAGCGTGGGAGATCGCGTGACCATTACCTGCCGTGCGAGCCA<br>GGATGTTAGTAATTGGGTCGCATGGTATCAGCAGAAACCAGGC<br>AAAGCGCCGAAACTTCTGATATCCTATGCTACTAGCCTGTATA<br>GCGGCGTGCCGTCGCGTTTTTCGGGCAGTGGCAGCGGCACGGA<br>CTTTACCCTGACGATATCTTCCTTACAACCGGAGGATTTTGCG<br>ACCTACTACTGTCAACAGCACTCTAACGCGCCGCTGACCTTCG<br>GTCAAGGCACCAAAGTGGAAATCAAACGCGGTGGTTCCTCTAG<br>ATCTTCCTCCTCTGGTGGCGGTGGCTCGGGCGGTGGTGGGGAA<br>GTGCAGCTGGTGGAATCGGGAGGCGGTCTGGTGCAACCTGGCG<br>GCAGCCTTCGTCTGAGCTGTGCGGCGAGCGGGTTCACCATTAG<br>CAGCTTTGGGATTCATTGGGTGCGTCAAGCTCCCGGCAAGGGG<br>CTGGAGTGGGTCGCGTGGATTGCTCCCTACGGTGGTGACACAT<br>ACTATGCCGACAGCGTGAAAGGTCGCTTTACGATTAGTGCGGA<br>CACCAGCAAAAATACCGCGTACCTGCAGATGAATAGCCTGCGT<br>GCGGAAGACACAGCGGTGTATTATTGCGCGCGTTCGTTTTTCG<br>GGTACTTCGATTATTGGGGGCAGGGCACCCTTGTTACCGTGAG<br>CTCGGCGTCAGCGGCCGCA | 29 |
| 117_57D-$V_H$ | EVQLVESGGGLVQPGGSLRLSCAASGFTISSFGIHWVRQAPGK<br>GLEWVAWIAPYGGDTYYADSVKGRFTISADTSKNTAYLQMNSL<br>RAEDTAVYYCARSFFGYFDYWGQGTLVTVSS | 30 |
| 117_57D-CDR-H2 | WIAPYGGDTY | 31 |
| 117_57E-scFv (DNA) | ATGGCCGATATTCAAATGACCCAGAGCCCGAGCAGCCTGAGCG<br>CGAGCGTGGGAGATCGCGTGACCATTACCTGCCGTGCGAGCCA<br>GGATGTTAGTAATTGGGTCGCATGGTATCAGCAGAAACCAGGC<br>AAAGCGCCGAAACTTCTGATATCCTATGCTACTAGCCTGTATA<br>GCGGCGTGCCGTCGCGTTTTTCGGGCAGTGGCAGCGGCACGGA<br>CTTTACCCTGACGATATCTTCCTTACAACCGGAGGATTTTGCG<br>ACCTACTACTGTCAACAGCACTCTAACGCGCCGCTGACCTTCG<br>GTCAAGGCACCAAAGTGGAAATCAAACGCGGTGGTTCCTCTAG<br>ATCTTCCTCCTCTGGTGGCGGTGGCTCGGGCGGTGGTGGGGAA<br>GTGCAGCTGGTGGAATCGGGAGGCGGTCTGGTGCAACCTGGCG<br>GCAGCCTTCGTCTGAGCTGTGCGGCGAGCGGGTTCACCATTAG<br>CAGCTTTGGGATTCATTGGGTGCGTCAAGCTCCCGGCAAGGGG<br>CTGGAGTGGGTCGCGTGGATTGCTCCCTACGGTGGTGAAACAT<br>ACTATGCCGACAGCGTGAAAGGTCGCTTTACGATTAGTGCGGA<br>CACCAGCAAAAATACCGCGTACCTGCAGATGAATAGCCTGCGT<br>GCGGAAGACACAGCGGTGTATTATTGCGCGCGTTCGTTTTTCG<br>GGTACTTCGATTATTGGGGGCAGGGCACCCTTGTTACCGTGAG<br>CTCGGCGTCAGCGGCCGCA | 32 |
| 117_57E-$V_H$ | EVQLVESGGGLVQPGGSLRLSCAASGFTISSFGIHWVRQAPGK<br>GLEWVAWIAPYGGETYYADSVKGRFTISADTSKNTAYLQMNSL<br>RAEDTAVYYCARSFFGYFDYWGQGTLVTVSS | 33 |
| 117_57E-CDR-H2 | WIAPYGGETY | 34 |
| 117_57DE-$V_H$ (DNA) | GAAGTGCAGCTGGTGGAATCGGGAGGCGGTCTGGTGCAACCTG<br>GCGGCAGCCTTCGTCTGAGCTGTGCGGCGAGCGGGTTCACCAT<br>TAGCAGCTTTGGGATTCATTGGGTGCGTCAAGCTCCCGGCAAG<br>GGGCTGGAGTGGGTCGCGTGGATTGCTCCCTACGGTGGTGACG<br>AATACTATGCCGACAGCGTGAAAGGTCGCTTTACGATTAGTGC<br>GGACACCAGCAAAAATACCGCGTACCTGCAGATGAATAGCCTG<br>CGTGCGGAAGACACAGCGGTGTATTATTGCGCGCGTTCGTTTT<br>TCGGGTACTTCGATTATTGGGGGCAGGGCACCCTTGTTACCGT<br>GAGCTCG | 35 |
| 117_57DE-$V_H$ | EVQLVESGGGLVQPGGSLRLSCAASGFTISSFGIHWVRQAPGK<br>GLEWVAWIAPYGGDEYYADSVKGRFTISADTSKNTAYLQMNSL<br>RAEDTAVYYCARSFFGYFDYWGQGTLVTVSS | 36 |

TABLE 2-continued

Anti-CD36 antibody sequences

| Description | Sequence | SEQ ID NO: |
| --- | --- | --- |
| 117_57DE-CDR-H2 | WIAPYGGDEY | 37 |
| 117_57EE-$V_H$ (DNA) | GAAGTGCAGCTGGTGGAATCGGGAGGCGGTCTGGTGCAACCTG<br>GCGGCAGCCTTCGTCTGAGCTGTGCGGCGAGCGGGTTCACCAT<br>TAGCAGCTTTGGGATTCATTGGGTGCGTCAAGCTCCCGGCAAG<br>GGGCTGGAGTGGGTCGCGTGGATTGCTCCCTACGGTGGTGAAG<br>AATACTATGCCGACAGCGTGAAAGGTCGCTTTACGATTAGTGC<br>GGACACCAGCAAAAATACCGCGTACCTGCAGATGAATAGCCTG<br>CGTGCGGAAGACACAGCGGTGTATTATTGCGCGCGTTCGTTTT<br>TCGGGTACTTCGATTATTGGGGGCAGGGCACCCTTGTTACCGT<br>GAGCTCG | 38 |
| 117_57EE-$V_H$ | EVQLVESGGGLVQPGGSLRLSCAASGFTISSFGIHWVRQAPGK<br>GLEWVAWIAPYGGEEYYADSVKGRFTISADTSKNTAYLQMNSL<br>RAEDTAVYYCARSFFGYFDYWGQGTLVTVSS | 39 |
| 117_57EE-CDR-H2 | WIAPYGGEEY | 40 |
| 117_DA57E-scFv (DNA) | ATGGCCGATATTCAAATGACCCAGAGCCCGAGCAGCCTGAGCG<br>CGAGCGTGGGAGATCGCGTGACCATTACCTGCCGTGCGAGCCA<br>GGATGTTAGTAATTGGGTCGCATGGTATCAGCAGAAACCAGGC<br>AAAGCGCCGAAACTTCTGATATCCTATGCTACTAGCCTGTATA<br>GCGGCGTGCCGTCGCGTTTTTCGGGCAGTGGCAGCGGCACGGA<br>CTTTACCCTGACGATATCTTCCTTACAACCGGAGGATTTTGCG<br>ACCTACTACTGTCAACAGCACTCTAACGCGCCGCTGACCTTCG<br>GTCAAGGCACCAAAGTGGAAATCAAACGCGGTGGTTCCTCTAG<br>ATCTTCCTCCTCTGGTGGCGGTGGCTCGGGCGGTGGTGGGGAA<br>GTGCAGCTGGTGGAATCGGGAGGCGGTCTGGTGCAACCTGGCG<br>GCAGCCTTCGTCTGAGCTGTGCGGCGAGCGGGTTCACCATTAG<br>CAGCTTTGGGATTCATTGGGTGCGTCAAGCTCCCGGCAAGGGG<br>CTGGAGTGGGTCGCGTGGATTGCTCCCTACGGTGGTGAAACAT<br>ACTATGCCGACAGCGTGAAAGGTCGCTTTACGATTAGTGCGGA<br>CACCAGCAAAAATACCGCGTACCTGCAGATGAATAGCCTGCGT<br>GCGGAAGACACAGCGGTGTATTATTGCGCGCGTTCGTTTTTCG<br>GGTACTTCGATTATTGGGGGCAGGGCACCCTTGTTACCGTGAG<br>CTCGGCGTCAGCGGCCGCA | 41 |
| 117_DA57E-$V_H$ | EVQLVESGGGLVQPGGSLRLSCAASGFTIDAFGIHWVRQAPGK<br>GLEWVAWIAPYGGETYYADSVKGRFTISADTSKNTAYLQMNSL<br>RAEDTAVYYCARSFFGYFDYWGQGTLVTVSS | 42 |
| 117_DA57E-CDR-H2 | WIAPYGGETY | 43 |
| 12P109-HC<br>A8A-HC<br>A8A-N52T-HC<br>117-HC (IgG1-N297A) | EVQLVESGGGLVQPGGSLRLSCAASGFTISSFGIHWVRQAPGK<br>GLEWVAWIAPYGGYTYYADSVKGRFTISADTSKNTAYLQMNSL<br>RAEDTAVYYCARSFFGYFDYWGQGTLVTVSSastkgpsvfpla<br>psskstsggtaalgclvkdyfpepvtvswnsgaltsgvhtfpa<br>vlqssglyslssvvtvpssslgtqtyicnvnhkpsntkvdkkv<br>epkscdkthtcppcpapellggpsvflfppkpkdtlmisrtpe<br>vtcvvvdvshedpevkfnwyvdgvevhnaktkpreeqyastyr<br>vvsvltvlhqdwlngkeykckvsnkalpapiektiskakgqpr<br>epqvytlppsreemtknqvsltclvkgfypsdiavewesngqp<br>ennykttppvldsdgsfflyskltvdksrwqqgnvfscsvmhe<br>alhnhytqkslslspg | 44 |
| 12P109-LC | DIQMTQSPSSLSASVGDRVTITCRASQDVSNWVAWYQQKPGKA<br>PKLLISTSTSLYSGVPSRFSGSGSGTDFTLTISSLQPEDFATY<br>YCQQYYTLPFTFGQGTKVEIKRtvaapsvfifppsdeqlksgt<br>asvvclInnfypreakvqwkvdnalqsgnsqesvteqdskdst<br>yslsstltlskadyekhkvyacevthqglsspvtksfnrgec | 45 |
| A8A-LC | DIQMTQSPSSLSASVGDRVTITCRASQDVSNWVAWYQQKPGKA<br>PKLLISYANSLYSGVPSRFSGSGSGTDFTLTISSLQPEDFATY<br>YCQQHSNLPLTFGQGTKVEIKRtvaapsvfifppsdeqlksgt<br>asvvclInnfypreakvqwkvdnalqsgnsqesvteqdskdst<br>yslsstltlskadyekhkvyacevthqglsspvtksfnrgec | 46 |
| A8A-N52T-LC | DIQMTQSPSSLSASVGDRVTITCRASQDVSNWVAWYQQKPGKA<br>PKLLISYA**T**SLYSGVPSRFSGSGSGTDFTLTISSLQPEDFATY<br>YCQQHSNLPLTFGQGTKVEIKRtvaapsvfifppsdeqlksgt<br>asvvclInnfypreakvqwkvdnalqsgnsqesvteqdskdst<br>yslsstltlskadyekhkvyacevthqglsspvtksfnrgec | 47 |

TABLE 2-continued

| Anti-CD36 antibody sequences | | |
|---|---|---|
| Description | Sequence | SEQ ID NO: |
| 117-HC (IgG4-S228P-FALA) | EVQLVESGGGLVQPGGSLRLSCAASGFTISSFGIHWVRQAPGK GLEWVAWIAPYGGYTYYADSVKGRFTISADTSKNTAYLQMNSL RAEDTAVYYCARSFFGYFDYWGQGTLVTVSSastkgpsvfpla pcsrstsestaalgclvkdyfpepvtvswnsgaltsgvhtfpa vlqssglyslssvvtvpssslgtktytcnvdhkpsntkvdkrv eskygppcppcpapeaaggpsvflfppkpkdtlmisrtpevtc vvvdvsqedpevqfnwyvdgvevhnaktkpreeqfnstyrvvs vltvlhqdwlngkeykckvsnkglpssiektiskakgqprepq vytlppsqeemtknqvsltclvkgfypsdiavewesngqpenn ykttppvldsdgsfflysrltvdksrwqegnvfscsvmhealh nhytqkslslslg | 48 |
| 117-LC 117_30AA-LC 117_30DA-LC 117_30DE-LC 117_57D-LC 117_57E-LC 117_57DE-LC 117_57EE-LC 117_DA57E-LC | DIQMTQSPSSLSASVGDRVTITCRASQDVSNWVAWYQQKPGKA PKLLISYATSLYSGVPSRFSGSGSGTDFTLTISSLQPEDFATY YCQQHSNAPLTFGQGTKVEIKRtvaapsvfifppsdeqlksgt asvvclInnfypreakvqwkvdnalqsgnsqesvteqdskdst yslsstltlskadyekhkvyacevthqglsspvtksfnrgec | 49 |
| 117_30AA-HC (IgG4-S228P-FALA) | EVQLVESGGGLVQPGGSLRLSCAASGFTIAAFGIHWVRQAPGK GLEWVAWIAPYGGYTYYADSVKGRFTISADTSKNTAYLQMNSL RAEDTAVYYCARSFFGYFDYWGQGTLVTVSSastkgpsvfpla pcsrstsestaalgclvkdyfpepvtvswnsgaltsgvhtfpa vlqssglyslssvvtvpssslgtktytcnvdhkpsntkvdkrv eskygppcppcpapeaaggpsvflfppkpkdtlmisrtpevtc vvvdvsqedpevqfnwyvdgvevhnaktkpreeqfnstyrvvs vltvlhqdwlngkeykckvsnkglpssiektiskakgqprepq vytlppsqeemtknqvsltclvkgfypsdiavewesngqpenn ykttppvldsdgsfflysrltvdksrwqegnvfscsvmhealh nhytqkslslslg | 50 |
| 117_30DA-HC (IgG4-S228P-FALA) | EVQLVESGGGLVQPGGSLRLSCAASGFTIDAFGIHWVRQAPGK GLEWVAWIAPYGGYTYYADSVKGRFTISADTSKNTAYLQMNSL RAEDTAVYYCARSFFGYFDYWGQGTLVTVSSastkgpsvfpla pcsrstsestaalgclvkdyfpepvtvswnsgaltsgvhtfpa vlqssglyslssvvtvpssslgtktytcnvdhkpsntkvdkrv eskygppcppcpapeaaggpsvflfppkpkdtlmisrtpevtc vvvdvsqedpevqfnwyvdgvevhnaktkpreeqfnstyrvvs vltvlhqdwlngkeykckvsnkglpssiektiskakgqprepq vytlppsqeemtknqvsltclvkgfypsdiavewesngqpenn ykttppvldsdgsfflysrltvdksrwqegnvfscsvmhealh nhytqkslslslg | 51 |
| 117_30DE-HC (IgG4-S228P-FALA) | EVQLVESGGGLVQPGGSLRLSCAASGFTIDSFGIHWVRQAPGK GLEWVAWIAPYGGETYYADSVKGRFTISADTSKNTAYLQMNSL RAEDTAVYYCARSFFGYFDYWGQGTLVTVSSastkgpsvfpla pcsrstsestaalgclvkdyfpepvtvswnsgaltsgvhtfpa vlqssglyslssvvtvpssslgtktytcnvdhkpsntkvdkrv eskygppcppcpapeaaggpsvflfppkpkdtlmisrtpevtc vvvdvsqedpevqfnwyvdgvevhnaktkpreeqfnstyrvvs vltvlhqdwlngkeykckvsnkglpssiektiskakgqprepq vytlppsqeemtknqvsltclvkgfypsdiavewesngqpenn ykttppvldsdgsfflysrltvdksrwqegnvfscsvmhealh nhytqkslslslg | 52 |
| 117_57D-HC (IgG4-S228P-FALA) | EVQLVESGGGLVQPGGSLRLSCAASGFTISSFGIHWVRQAPGK GLEWVAWIAPYGGDTYYADSVKGRFTISADTSKNTAYLQMNSL RAEDTAVYYCARSFFGYFDYWGQGTLVTVSSastkgpsvfpla pcsrstsestaalgclvkdyfpepvtvswnsgaltsgvhtfpa vlqssglyslssvvtvpssslgtktytcnvdhkpsntkvdkrv eskygppcppcpapeaaggpsvflfppkpkdtlmisrtpevtc vvvdvsqedpevqfnwyvdgvevhnaktkpreeqfnstyrvvs vltvlhqdwlngkeykckvsnkglpssiektiskakgqprepq vytlppsqeemtknqvsltclvkgfypsdiavewesngqpenn ykttppvldsdgsfflysrltvdksrwqegnvfscsvmhealh nhytqkslslslg | 53 |
| 117_57E-HC (IgG4-S228P-FALA) | EVQLVESGGGLVQPGGSLRLSCAASGFTISSFGIHWVRQAPGK GLEWVAWIAPYGGETYYADSVKGRFTISADTSKNTAYLQMNSL RAEDTAVYYCARSFFGYFDYWGQGTLVTVSSastkgpsvfpla pcsrstsestaalgclvkdyfpepvtvswnsgaltsgvhtfpa | 54 |

TABLE 2-continued

Anti-CD36 antibody sequences

| Description | Sequence | SEQ ID NO: |
|---|---|---|
| | vlqssglyslssvvtvpssslgtktytcnvdhkpsntkvdkrv eskygppcppcpapeaaggpsvflfppkpkdtlmisrtpevtc vvvdvsqedpevqfnwyvdgvevhnaktkpreeqfnstyrvvs vltvlhqdwlngkeykckvsnkglpssiektiskakgqprepq vytlppsqeemtknqvsltclvkgfypsdiavewesngqpenn ykttppvldsdgsfflysrltvdksrwqegnvfscsvmhealh nhytqkslslslg | |
| 117_57DE-HC (IgG4-S228P-FALA) | EVQLVESGGGLVQPGGSLRLSCAASGFTISSFGIHWVRQAPGK GLEWVAWIAPYGGDEYYADSVKGRFTISADTSKNTAYLQMNSL RAEDTAVYYCARSFFGYFDYWGQGTLVTVSSastkgpsvfpla pcsrstsestaalgclvkdyfpepvtvswnsgaltsgvhtfpa vlqssglyslssvvtvpssslgtktytcnvdhkpsntkvdkrv eskygppcppcpapeaaggpsvflfppkpkdtlmisrtpevtc vvvdvsqedpevqfnwyvdgvevhnaktkpreeqfnstyrvvs vltvlhqdwlngkeykckvsnkglpssiektiskakgqprepq vytlppsqeemtknqvsltclvkgfypsdiavewesngqpenn ykttppvldsdgsfflysrltvdksrwqegnvfscsvmhealh nhytqkslslslg | 55 |
| 117_57EE-HC (IgG4-S228P-FALA) | EVQLVESGGGLVQPGGSLRLSCAASGFTISSFGIHWVRQAPGK GLEWVAWIAPYGGEEYYADSVKGRFTISADTSKNTAYLQMNSL RAEDTAVYYCARSFFGYFDYWGQGTLVTVSSastkgpsvfpla pcsrstsestaalgclvkdyfpepvtvswnsgaltsgvhtfpa vlqssglyslssvvtvpssslgtktytcnvdhkpsntkvdkrv eskygppcppcpapeaaggpsvflfppkpkdtlmisrtpevtc vvvdvsqedpevqfnwyvdgvevhnaktkpreeqfnstyrvvs vltvlhqdwlngkeykckvsnkglpssiektiskakgqprepq vytlppsqeemtknqvsltclvkgfypsdiavewesngqpenn ykttppvldsdgsfflysrltvdksrwqegnvfscsvmhealh nhytqkslslslg | 56 |
| 117_DA57E-HC (IgG4-S228P-FALA) | EVQLVESGGGLVQPGGSLRLSCAASGFTIDAFGIHWVRQAPGK GLEWVAWIAPYGGETYYADSVKGRFTISADTSKNTAYLQMNSL RAEDTAVYYCARSFFGYFDYWGQGTLVTVSSastkgpsvfpla pcsrstsestaalgclvkdyfpepvtvswnsgaltsgvhtfpa vlqssglyslssvvtvpssslgtktytcnvdhkpsntkvdkrv eskygppcppcpapeaaggpsvflfppkpkdtlmisrtpevtc vvvdvsqedpevqfnwyvdgvevhnaktkpreeqfnstyrvvs vltvlhqdwlngkeykckvsnkglpssiektiskakgqprepq vytlppsqeemtknqvsltclvkgfypsdiavewesngqpenn ykttppvldsdgsfflysrltvdksrwqegnvfscsvmhealh nhytqkslslslg | 57 |

1. Anti-CD36 Antibody Binding Affinity and Functional Characteristics

In some embodiments, the anti-CD36 antibodies provided herein have an equilibrium dissociation constant ($K_D$) for binding to CD36 of <100 nM, <10 nM, <1 nM, <0.1 nM, <0.01 nM, or <0.001 nM (e.g., $10^{-8}$ M or less, from $10^{-8}$ M to $10^{-13}$ M, e.g., from $10^{-9}$ M to $10^{-13}$ M).

It is contemplated that the various anti-CD36 antibodies generated as disclosed herein include antibodies capable of high-affinity binding to hCD36, mCD36, rhesus CD36, both hCD36 and mCD36, and/or hCD36, mCD36, and rhesus CD36. More specifically, in some embodiments, the anti-CD36 antibodies of the present disclosure bind to hCD36 with a binding affinity of $1\times10^{-8}$ M or less, $1\times10^{-9}$ M or less, $1\times10^{-10}$ M or less, or $1\times10^{-11}$ M or less. In some embodiments, the binding affinity is measured as the equilibrium dissociation constant ($K_D$) for binding to the hCD36 polypeptide of SEQ ID NO: 58 or SEQ ID NO: 59. In some embodiments, the anti-CD36 antibodies of the present disclosure bind to mCD36 with a binding affinity of $1\times10^{-8}$ M or less, $1\times10^{-9}$ M or less, $1\times10^{-10}$ M or less, or $1\times10^{-11}$ M or less. In some embodiments, the binding affinity is measured as the equilibrium dissociation constant ($K_D$) for binding to the mCD36 polypeptide of SEQ ID NO: 60 or SEQ ID NO: 61. In some embodiments, the anti-CD36 antibodies of the present disclosure bind to rhesus CD36 with a binding affinity of $1\times10^{-8}$ M or less, $1\times10^{-9}$ M or less, $1\times10^{-10}$ M or less, or $1\times10^{-11}$ M or less. In some embodiments, the binding affinity is measured as the equilibrium dissociation constant ($K_D$) for binding to the rhesus CD36 polypeptide of SEQ ID NO: 62 or SEQ ID NO: 63. In some embodiments, the anti-CD36 antibodies of the present disclosure bind to both hCD36 and mCD36 with a binding affinity of $1\times10^{-8}$ M or less, $1\times10^{-9}$ M or less, $1\times10^{-10}$ M or less, or $1\times10^{-11}$ M or less. In some embodiments, the anti-CD36 antibodies of the present disclosure bind to both hCD36 and rhesus CD36 with a binding affinity of $1\times10^{-8}$ M or less, $1\times10^{-9}$ M or less, $1\times10^{-10}$ M or less, or $1\times10^{-11}$ M or less.

Generally, binding affinity of a ligand to its receptor can be determined using any of a variety of assays and expressed in terms of a variety of quantitative values. Specific CD36 binding assays useful in determining affinity of the antibodies are disclosed in the Examples herein. Additionally, antigen binding assays are known in the art and can be used herein including without limitation any direct or competitive binding assays using techniques such as western blots, radioimmunoassays, enzyme-linked immunoabsorbent assay (ELISA), "sandwich" immunoassays, surface plasmon resonance based assay (such as the BIAcore assay as described in WO2005/012359), immunoprecipitation assays, fluorescent immunoassays, protein A immunoassays, flow cytometric and fluorescence activated cell sorting (FACS) assays, and the like.

Accordingly, in some embodiments, the binding affinity is expressed as $K_D$ values and reflects intrinsic binding affinity (e.g., with minimized avidity effects). The anti-CD36 antibodies of the present disclosure exhibit strong binding affinities for the hCD36 polypeptide of SEQ ID NO: 58, for example, exhibiting $K_D$ values of between 10 nM and 1 pM. Accordingly, anti-CD36 antibodies of the present disclosure may compete with antibodies having lower affinity for the same or overlapping epitopes of CD36.

In some embodiments, the anti-CD36 antibodies provided herein decrease, inhibit, and/or fully-block ligand binding to CD36, and immune regulation and/or immune signaling mediated by ligand binding to CD36, including the maintenance of TAMs in the tumor microenvironment. The ability of the antibodies to inhibit these immune regulatory and immune signaling pathways mediated by ligand binding to CD36 can be assayed in vitro using known cell-based assays including those assays described in the Examples of the present disclosure.

Accordingly, in some embodiments, the CD36 antibodies of the present disclosure are characterized by one or more of following functional properties based on the ability to decrease, inhibit, and/or fully-block intracellular signaling by CD36-mediated pathways.

In at least one embodiment, the anti-CD36 antibody binds to human CD36 with a binding affinity of $1\times10^{-8}$ M or less, $1\times10^{-9}$ M or less, $1\times10^{-10}$ M or less; optionally, wherein the binding affinity is measured by equilibrium dissociation constant ($K_D$) to a hCD36 polypeptide of SEQ ID NO: 58 or 59.

In at least one embodiment of the anti-CD36 antibody, the antibody binds to mouse CD36 with a binding affinity of $1\times10^{-8}$ M or less, $1\times10^{-9}$ M or less, $1\times10^{-10}$ M or less; optionally, wherein the binding affinity is measured by equilibrium dissociation constant ($K_D$) to a mCD36 polypeptide of SEQ ID NO: 60 or 61.

In at least one embodiment of the anti-CD36 antibody, the antibody binds to rhesus CD36 with a binding affinity of $1\times10^{-8}$ M or less, $1\times10^{-9}$ M or less, $1\times10^{-10}$ M or less; optionally, wherein the binding affinity is measured by equilibrium dissociation constant ($K_D$) to a rhesus CD36 polypeptide of SEQ ID NO: 62 or 62.

In at least one embodiment of the anti-CD36 antibody, the antibody inhibits CD36-dependent oxidized LDL uptake in F293 cells that overexpress surface human CD36 by at least 65%, at least 75%, at least 85%, at least 95%, or at least 100%; optionally, wherein at an oxLDL concentration of 1-10 μg/mL the antibody has an $IC_{50}$ of 5 nM or less, 1 nM or less, 0.5 nM or less, or 0.1 nM or less.

In at least one embodiment of the anti-CD36 antibody, the antibody inhibits CD36-dependent oxidized LDL uptake in U937 cells by at least 65%, at least 75%, at least 85%, at least 95%, or at least 100%; optionally, wherein at an oxLDL concentration of 1-10 μg/mL the antibody has an $IC_{50}$ of 5 nM or less, 1 nM or less, 0.5 nM or less, or 0.1 nM or less.

In at least one embodiment of the anti-CD36 antibody, the antibody inhibits CD36-dependent oxidized LDL uptake in mouse CD45+ TILs by at least 65%, at least 75%, at least 85%, at least 95%, or at least 100%; optionally, wherein at an oxLDL concentration of 1-10 μg/mL the antibody has an $IC_{50}$ of 5 nM or less, 1 nM or less, 0.5 nM or less, or 0.1 nM or less.

2. Anti-CD36 Antibody Fragments

In some embodiments, the anti-CD36 antibody of the present disclosure can be an antibody fragment. Antibody fragments useful with the binding determinants the present disclosure include, but are not limited to, Fab, Fab', Fab'-SH, $F(ab')_2$, Fv, scFv fragments, monovalent, single domain antibody, one-armed or single-arm antibody, and other fragments described herein and known in the art. Accordingly, in some embodiments of the anti-CD36 antibodies of the present disclosure, the antibody is an antibody fragment selected from the group consisting of $F(ab')_2$, Fab', Fab, Fv, single domain antibody (VHH), single-arm antibody, and scFv.

For a review of various antibody fragments, see e.g., Hudson et al. Nat. Med. 9:129-134 (2003). For a review of scFv fragments, see, e.g., Pluckthun, in The Pharmacology of Monoclonal Antibodies, vol. 113, Rosenburg and Moore eds., (Springer-Verlag, New York), pp. 269-315 (1994); sce also WO93/16185; and U.S. Pat. Nos. 5,571,894 and 5,587,458. For a description of Fab and $F(ab')_2$ fragments comprising salvage receptor binding epitope residues and having increased in vivo half-life, see U.S. Pat. No. 5,869,046. Other monovalent antibody forms are described in, e.g., WO2007/048037,WO2008/145137, WO2008/145138, and WO2007/059782. Monovalent, single-armed antibodies are described, e.g., in WO2005/063816. Diabodies are antibody fragments with two antigen-binding sites that may be bivalent or bispecific (see e.g., EP0404097; WO93/01161; Hudson et al., Nat. Med. 9:129-134 (2003); and Hollinger et al., Proc. Natl. Acad. Sci. USA 90: 6444-6448 (1993)).

In some embodiments, the antibody fragments are single-domain antibodies which comprise all or a portion of the heavy chain variable domain or all or a portion of the light chain variable domain of an antibody. In some embodiments, a single-domain antibody is a human single-domain antibody (Domantis, Inc., Waltham, MA; see, e.g., U.S. Pat. No. 6,248,516).

Antibody fragments can be made by various techniques, including but not limited to proteolytic digestion of an intact antibody as well as production by recombinant host cells (e.g., *E. coli* or phage), as described herein.

3. Chimeric, Humanized, and Human Anti-CD36 Antibodies

In some embodiments, the anti-CD36 antibody of the present disclosure can be a chimeric antibody. (See e.g., chimeric antibodies as described in U.S. Pat. No. 4,816,567; and Morrison et al., Proc. Natl. Acad. Sci. USA 81: 6851-6855 (1984)). In one embodiment, a chimeric antibody comprises a non-human variable region (e.g., a variable region derived from a mouse, rat, hamster, rabbit, or non-human primate, such as a monkey) and a human constant region. In some embodiments, a chimeric antibody is a "class switched: antibody in which the class or subclass has been changed from that of the parent antibody. It is contemplated that chimeric antibodies can include antigen-binding fragments thereof.

In some embodiments, the anti-CD36 antibody of the present disclosure is a humanized antibody. Typically, a non-human antibody is humanized to reduce immunogenicity to humans, while retaining the specificity and affinity of the parental non-human antibody. Generally, a humanized antibody comprises one or more variable domains in which HVRs, CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the CDR residues are derived) to restore or improve antibody specificity or affinity.

Humanized antibodies and methods of making them are reviewed in, e.g., Almagro and Fransson, Front. Biosci. 13: 1619-1633 (2008), and are further described in, e.g., Riechmann et al., Nature 332:323-329 (1988); Queen et al., Proc. Natl. Acad. Sci. USA 86: 10029-10033 (1989); U.S. Pat. Nos. 5,821,337, 7,527,791, 6,982,321, and 7,087,409; Kashmiri et al, Methods 36: 25-34 (2005) (describing SDR (a-HVR) grafting); Padlan, Mol. Immunol. 28: 489-498 (1991) (describing "resurfacing"); Dall'Acqua et al., Methods 36: 43-60 (2005) (describing "FR shuffling"); and Osbourn et al., Methods 36: 61-68 (2005) and Klimka et al., Br. J. Cancer, 83: 252-260 (2000) (describing the "guided selection" approach to FR shuffling).

Human framework regions that may be used for humanization include but are not limited to: framework regions selected using the "best-fit" method (see, e.g., Sims et al. J. Immunol. 151: 2296 (1993)); framework regions derived from the consensus sequence of human antibodies of a particular subgroup of light or heavy chain variable regions (see, e.g., Carter et al., Proc. Natl. Acad. Sci. USA 89: 4285 (1992); and Presta et al., J. Immunol. 151: 2623 (1993)); human mature (somatically mutated) framework regions or human germline framework regions (see, e.g., Almagro and Fransson, Front. Biosci. 13: 1619-1633 (2008)); and framework regions derived from screening FR libraries (see, e.g., Baca et al., J. Biol. Chem. 272: 10678-10684 (1997) and Rosok et al., J. Biol. Chem. 271: 22611-22618 (1996)).

In some embodiments, the anti-CD36 antibody of the present disclosure can be a human antibody. Human antibodies can be produced using various techniques known in the art. Human antibodies are described generally in van Dijk and van de Winkel, Curr. Opin. Pharmacol. 5: 368-74 (2001) and Lonberg, Curr. Opin. Immunol. 20: 450-459 (2008). Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23: 1117-1125 (2005). See also, e.g., XENOMOUSE™ technology in U.S. Pat. Nos. 6,075,181 and 6,150,584; HUMAB® technology in U.S. Pat. No. 5,770,429; K-M MOUSE® technology in U.S. Pat. No. 7,041,870; and VELOCIMOUSE® technology in U.S. Pat. Appl. Pub. No. US 2007/0061900). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. See, e.g., Kozbor J. Immunol, 133: 3001 (1984); Brodeur et al., Monoclonal Antibody Production Techniques and Applications, pp. 51-63 (Marcel Dekker, Inc., New York, 1987); and Boerner et al., J. Immunol. 147: 86 (1991). Human antibodies generated via human B-cell hybridoma technology are also described in Li et al., Proc. Natl. Acad. Sci. USA 103: 3557-3562 (2006). Additional methods include those described, for example, in U.S. Pat. No. 7,189,826 (describing production of monoclonal human IgM antibodies from hybridoma cell lines). Human hybridoma technology (Trioma technology) is also described in Vollmers and Brandlein, Histology and Histopathology, 20(3): 927-937 (2005) and Vollmers and Brandlein, Methods and Findings in Experimental and Clinical Pharmacology 27(3): 185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

4. Library-Derived Variants of Anti-CD36 Antibodies

In at least one embodiment, improved variants of anti-CD36 antibodies may be isolated by screening combinatorial libraries for antibodies with the desired improved functional characteristic, such as binding affinity or cross-reactivity. For example, a variety of methods are known in the art for generating phage display libraries and screening such libraries for variant antibodies possessing the improved binding characteristics. Other methods for producing such library-derived antibodies can be found in e.g., Hoogenboom et al., Methods in Molecular Biology 178: 1-37 (O'Brien et al., ed., Human Press, Totowa, NJ, 2001); McCafferty et al., Nature 348: 552-554 (1990); Clackson et al., Nature 352: 624-628 (1991); Marks et al., J. Mol. Biol. 222: 581-597 (1992); Marks and Bradbury, m Methods in Molecular Biology 248: 161-175 (Lo, ed., Human Press, Totowa, NJ, 2003); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132(2004).

5. Multispecific Antibodies and Antibody Fusions

In at least one embodiment, it is contemplated that an anti-CD36 antibody of the present disclosure can be a multispecific antibody, e.g., a bispecific antibody. In some embodiments, the multispecific antibody has at least two different binding sites, each with a binding specificity for a different antigen, at least one of which specifically binds CD36. In at least one embodiment, it is contemplated that the multispecific antibody is a bispecific antibody comprising a specificity for CD36 and a specificity for another antigen that mediates immune regulation, immune signaling, and/or is expressed on a cancer or tumor cell. For example, the other specificity could be for an immune checkpoint molecule, such as PD1, LAG3, CTLA-4, A2AR, TIM-3, BTLA, CD276, CD328, VTCN1, IDO, KIR, NOX2, VISTA, OX40, CD27, CD28, CD40, CD122, CD137, GITR, or ICOS.

Techniques for making multispecific antibodies include, but are not limited to, recombinant co-expression of two immunoglobulin heavy chain-light chain pairs having different specificities (see e.g., Milstein and Cuello, Nature 305: 537 (1983), WO 93/08829, and Traunecker et al., EMBO J. 10: 3655 (1991)). “Knob-in-hole” engineering can also be used to generate bispecific antibodies useful with the anti-CD36 antibodies of the present disclosure. Techniques for knob-in-hole engineering are known in the art and described in e.g., U.S. Pat. No. 5,731,168.

Multispecific antibodies can also be made by engineering “electrostatic steering” effects that favor formation of Fe-heterodimeric antibody molecules rather than homodimers (WO 2009/089004A1); cross-linking two or more antibodies or fragments (see, e.g., U.S. Pat. No. 4,676,980, and Brennan et al., Science 229: 81 (1985)); using leucine zippers to produce bispecific antibodies (see, e.g., Kostelny et al., J. Immunol. 148(5): 1547-1553 (1992)); using “diabody” technology for making bispecific antibody fragments (see, e.g., Hollinger et al., Proc. Natl. Acad. Sci. USA 90: 6444-6448 (1993)); using single-chain Fv (scFv) dimers (see, e.g. Gruber et al., J. Immunol. 152: 5368 (1994); or tri-specific antibodies (see e.g., Tutt et al., J. Immunol. 147: 60 (1991).

In at least one embodiment, the anti-CD36 antibodies provided herein can comprise an antibody fusion with a protein. Methods for preparation and use of antibody fusions or fusion proteins are well known in the art. Typically, the antibody is covalently conjugated (or fused) to the protein, typically via a linker polypeptide. The conjugation can occur via the terminus of the antibody's light chain (LC) or heavy chain (HC). Antibody fusions can also be prepared with antibody fragments. In one exemplary embodiment of an antibody fusion contemplated by the present disclosure, the fusion includes a full length anti-CD36 antibody fused via a linker at a light or heavy chain terminus to a T-cell activating or immunostimulatory cytokine. The cytokine can include, but is not limited to, IL-2, IL-7, IL-10, IL-12, IL-15, IL-21, or IFN-α. Such an anti-CD36 antibody fusion can block activity mediated by CD36 signaling and provide an immunostimulatory cytokine effect. The ability of such anti-CD36 antibody fusions to provide immunostimulatory cytokine effects can be assayed in vitro using known cell-based assays associated with the cytokine.

6. Variants of Anti-CD36 Antibodies

In some embodiments, variants of the anti-CD36 antibodies of the present disclosure are contemplated having improved characteristics such as binding affinity and/or other biological properties of the antibody. Variants can be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristic of CD36 antigen binding.

A. Substitution, Insertion, and Deletion Variants

In some embodiments, anti-CD36 antibody variants having one or more amino acid substitutions in addition to those described herein are provided. Sites for mutagenesis can include the CDRs, HVRs and FRs. Typical “conservative” amino acid substitutions and/or substitutions based on common side-chain class or properties are well-known in the art and can be used in the embodiments of the present disclosure. The present disclosure also contemplates variants based on non-conservative amino acid substitutions in which a member of one of amino acid side chain class is exchanged for an amino acid from another class. Amino acid side chains are typically grouped according to the following classes or common properties: (1) hydrophobic: Met, Ala, Val, Leu, Ile, Norleucine; (2) neutral hydrophilic: Cys, Ser, Thr, Asn, Gln; (3) acidic: Asp, Glu; (4) basic: His, Lys, Arg; (5) chain orientation influencing: Gly, Pro; and (6) aromatic: Trp, Tyr, Phe. Techniques are well-known in the art for amino acid substitution into an antibody and subsequent screening for desired function, e.g., retained/improved antigen binding, decreased immunogenicity, or improved ADCC or CDC.

Amino acid substitution variants can also include variants having one or more substitutions in hypervariable regions of a parent antibody. Generally, the resulting variant(s) selected for further study will have modifications of certain biological properties (e.g., increased affinity, reduced immunogenicity) relative to the parent antibody and/or will retain certain biological properties of the parent antibody. An exemplary substitutional variant is an affinity matured antibody, which may be conveniently generated, using phage display-based affinity maturation techniques. Briefly, one or more HVR residues are mutated and the variant antibodies displayed on phage and screened for a particular biological activity (e.g., binding affinity).

One useful method for identifying residues or regions of an antibody that may be targeted for mutagenesis is “alanine scanning mutagenesis” (see e.g., Cunningham and Wells, Science 244: 1081-1085 (1989)). In this method, a residue or group of target residues (e.g., charged residues such as Arg, Asp, His, Lys, and Glu) are identified and replaced by a neutral or negatively charged amino acid (e.g., Ala or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen can be determined. Such contact residues and neighboring residues may be targeted or eliminated as candidates for substitution. Variants may be screened to determine whether they contain the desired properties.

Amino acid sequence insertions which can be prepared include amino-and/or carboxyl-terminal fusions ranging in length from one residue to polypeptides containing a hundred or more residues, as well as intra-sequence insertions of single or multiple amino acid residues. Examples of terminal insertions include an antibody with an N-terminal methionyl residue. Other insertional variants of the antibody molecule can include a fusion of the N- or C-terminus of the antibody to an enzyme or a polypeptide which increases antibody serum half-life.

Other residue substitutions can be made in HVRs to improve antibody affinity. Such alterations may be made in “hotspots,” i.e., residues encoded by codons that undergo mutation at high frequency during the somatic maturation process (see, e.g., Chowdhury, Methods Mol. Biol. 207: 179-196 (2008)) with the resulting variant $V_H$ or $V_L$ being tested for binding affinity. In one embodiment, affinity maturation can be carried out by constructing and reselecting from secondary libraries (see e.g., in Hoogenboom et al., Methods in Molecular Biology 178: 1-37 (O'Brien et al., ed., Human Press, Totowa, NJ, (2001).) Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. HVR-H3 and HVR-L3 in particular are often targeted. Generally, substitutions, insertions, or deletions can be made within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots."

In some embodiments, it is contemplated that the anti-CD36 antibody described herein can be substituted at specific non-HVR positions with cysteine residues so as to create reactive thiol groups. Such engineered "thioMAbs" can be used to conjugate the antibody to e.g., drug moieties or linker-drug moicties and thereby create immunoconjugates, as described elsewhere herein. Cysteine engineered antibodies can be generated as described in e.g., U.S. Pat. No. 7,521,541. In some embodiments, any one or more of the following antibody residues can be substituted with cysteine: V205 (Kabat numbering) of the light chain; A118 (EU numbering) of the heavy chain; and S400 (EU numbering) of the heavy chain Fc region.

B. Glycosylation Variants

In some embodiments, the anti-CD36 antibody of the present disclosure is altered to increase or decrease the extent to which the antibody is glycosylated. Addition or deletion of glycosylation sites to an antibody can be carried out by altering the amino acid sequence such that one or more glycosylation sites is created or removed. In embodiments where the antibody comprises an Fc region, the carbohydrate attached to the Pc region can be altered. Typically, native antibodies produced by mammalian cells comprise a branched, biantennary oligosaccharide attached by an N-linkage to the asparagine at about position 297 ("N297") of the CH2 domain of the Fc region (see, e.g., Wright et al. TIBTECH 15:26-32 (1997)). The oligosaccharide may include various carbohydrates, such as mannose, N-acetyl glucosamine (GlcNAc), galactose, and sialic acid, as well as, a fucose attached to a GlcNAc in the "stem" of the bi-antennary oligosaccharide structure. In some embodiments, the modifications of the oligosaccharide of an Fe region of an antibody can create a variant with certain improved properties.

In some embodiments, the anti-CD36 antibody of the present disclosure can be a variant comprising a carbohydrate structure that lacks fucose attached (directly or indirectly) to an Fe region. For example, the amount of fucose in such antibody may be from about 1% to about 80%, from about 1% to about 65%, from about 5% to about 65%, or from about 20% to about 40%. The amount of fucose can be determined by calculating the average amount of fucose within the sugar chain attached to residue N297, relative to the sum of all glyco-structures attached at N297 (e.g., complex, hybrid and high mannose structures) as measured by MALDI-TOF mass spectrometry (see e.g., WO 2008/077546).

In some embodiments, the fucosylation variants can provide improved ADCC function of the variant antibody. See, e.g., US Patent Publication Nos. US 2003/0157108, or US 2004/0093621. Examples of "defucosylated" or "fucose-deficient" antibodies and associated methods for preparing them are disclosed in e.g., US2003/0157108; US2003/0115614; US2002/0164328; US2004/0093621; US2004/0132140; US2004/0110704; US2004/0110282; US2004/0109865; WO2000/61739; WO2001/29246; WO2003/085119; WO2003/084570; WO2005/035586; WO2005/035778; WO2005/053742; WO2002/031140; Okazaki et al., J. Mol. Biol. 336: 1239-1249 (2004); Yamane-Ohnuki et al., Biotech. Bioeng. 87: 614 (2004). Cell lines useful for producing defucosylated antibodies include Led 3 CHO cells deficient in protein fucosylation (see e.g., Ripka et al., Arch. Biochem. Biophys. 249: 533-545 (1986); US2003/0157108, and WO2004/056312), and knockout cell lines, such as alpha-1,6-fucosyltransferase gene, FUT8, knockout CHO cells (see, e.g., Yamane-Ohnuki et al. Biotech. Bioeng. 87: 614 (2004); Kanda, Y. et al., Biotechnol. Bioeng. 94(4): 680-688 (2006); and WO2003/085107).

C. Fc Region Variants

In some embodiments, an anti-CD36 antibody of the present disclosure can comprise one or more amino acid modifications in the Fe region (i.e., an Fe region variant). The Fc region variant may comprise a human Fe region sequence (e.g., a human IgG1, IgG2, IgG3, or IgG4 Fc region) comprising an amino acid substitution at one or more amino acid residue positions. A wide range of Fe region variants known in the art that are useful with the anti-CD36 antibodies of the present disclosure are described below.

In some embodiments, the anti-CD36 antibody is an Fe region variant which has altered effector function. In some embodiments, the antibody with altered effector function possesses some (but not all of) the effector functions, decreased effector function, or none of the effector functions (e.g., effectorless) of the parent antibody. Effectorless Fe region variants are more desirable for certain applications where effector function (such as ADCC) is unnecessary or deleterious, and/or in vivo half-life of the antibody is important. Fe region variant antibodies having reduced effector or effectorless function can result from amino acid substitution at one or more of the following Fc region positions: 238, 265, 269, 270, 297, 327 and 329. (see, e.g., U.S. Pat. No. 6,737,056). Such Fc region variants can include amino acid substitutions at two or more of positions 265, 269, 270, 297 and 327. Such Fe region variants can also include substitutions of both residues 265 and 297 to alanine (see e.g., U.S. Pat. No. 7,332,581).

Some Fc region variants are capable of providing improved or diminished binding to FeRs (see e.g., U.S. Pat. No. 6,737,056; WO 2004/056312; and Shields et al., J. Biol. Chem. 9(2): 6591-6604 (2001)). Some Fc region variants capable of providing improved ADCC comprise one or more amino acid substitutions at e.g., positions 298, 333, and/or 334 of the Fc region (based on EU numbering). Fc region variants having altered (i.e., either improved or diminished) Clq binding and/or Complement Dependent Cytotoxicity (CDC), as described in e.g., U.S. Pat. No. 6,194,551, WO99/51642, and Idusogie et al., J. Inmunol. 164: 4178-4184 (2000).

Some Fc region variants are capable of providing increased half-lives and improved binding to the neonatal Fe receptor (FcRn) are disclosed in e.g., US2005/0014934A1 (Hinton et al.). Such Fc region variants comprise amino acid substitutions at one or more of positions: 238, 256, 265, 272, 286, 303, 305, 307, 311, 312, 317, 340, 356, 360, 362, 376, 378, 380, 382, 413, 424, and 434. Other Fc region variants with increased half-lives include the set of YTE mutations at positions 252, 254, and 256 (i.e., M252Y/S254T/T256E)

described in e.g., U.S. Pat. No. 7,658,921B2 (Dall'Acqua et al.). Additional examples of Fc region variants can be found in e.g., U.S. Pat. Nos. 5,648,260 and 5,624,821; and WO94/29351.

Generally, in vitro and/or in vivo cytotoxicity assays can be carried out to confirm the reduction/depletion of CDC and/or ADCC activities in an Fe region variant. For example, Fe receptor (FcR) binding assays can be conducted to ensure that the antibody lacks FcγR binding (hence likely lacking ADCC activity) but retains FeRn binding ability. The primary cells for mediating ADCC, NK cells express FcγRIII only, whereas monocytes express FcγRI, FcγRII, and FcγRIII. Non-limiting examples of in vitro assays to assess ADCC activity of a molecule of interest is described in U.S. Pat. No. 5,500,362 (see, e.g. Hellstrom, et al., Proc. Natl. Acad. Sci. USA 83: 7059-7063 (1986)) and Hellstrom, et al., Proc. Natl. Acad. Sci. USA 82: 1499-1502 (1985); U.S. Pat. No. 5,821,337 (see Bruggemann, M. et al., J. Exp. Med. 166: 1351-1361 (1987)). Alternatively, non-radioactive assay methods may be employed (see, for example, ACTI™ nonradioactive cytotoxicity assay for flow cytometry (CellTechnology, Inc. Mountain View, CA; and CytoTox96® non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. Proc. Natl. Acad. Sci. USA 95: 652-656 (1998). Clq binding assays may also be carried out to confirm that the antibody is unable to bind Clq and hence lacks CDC activity. See, e.g., Clq and C3c binding ELISA in WO2006/029879 and WO2005/100402. To assess complement activation, a CDC assay may be performed (see, e.g., Gazzano-Santoro et al., J. Immunol. Methods 202: 163 (1996); Cragg, M. S. et al., Blood 101: 1045-1052 (2003); and Cragg, M. S. and M. J. Glennie, Blood 103: 2738-2743 (2004)). FeRn binding and in vivo clearance/half-life determinations can be performed using methods known in the art (see, e.g., Petkova et al., Intl. Immunol. 18(12): 1759-1769 (2006)).

D. Non-Protein Antibody Derivatives—Immunoconjugates

In some embodiments, the anti-CD36 antibody of the present disclosure may be further modified (i.e., derivatized) with non-proteinaceous moieties. Non-proteinaceous mojeties suitable for derivatization of the antibody include, but are not limited to, water soluble polymers, such as: polyethylene glycol (PEG), copolymers of ethylene glycol and propylene glycol, carboxy-methylcellulose, dextran, polyvinyl alcohol, polyvinyl pyrrolidone, poly-1,3-dioxolane, poly-1,3,6-trioxane, ethylene/maleic anhydride copolymer, poly-amino acid homo-polymers or random co-polymers, and dextran or poly(n-vinyl pyrrolidone) polyethylene glycol, propylene glycol homo-polymers, polypropylene oxide/ethylene oxide co-polymers, polyoxy-ethylated polyols (e.g., glycerol), polyvinyl alcohol, and mixtures thereof. In some embodiments, modification of the antibody can be carried out using methoxy-polyethylene glycol propionaldehyde. The polymers may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody, e.g., whether the antibody derivative will be used in a therapy under defined conditions.

In some embodiments, the anti-CD36 antibody of the present disclosure can also be an immunoconjugate, wherein the immunoconjugate comprises an anti-CD36 antibody conjugated to one or more cytotoxic agents. Suitable cytotoxic agents contemplated by the present disclosure include chemotherapeutic agents, drugs, growth inhibitory agents, toxins (e.g., protein toxins, enzymatically active toxins of bacterial, fungal, plant, or animal origin, or fragments thereof), or radioactive isotopes. In some embodiments, the immunoconjugate is an antibody-drug conjugate (ADC) in which an anti-CD36 antibody, as described herein, is conjugated to one or more drugs. In some embodiments, an immunoconjugate of the present disclosure comprises an anti-CD36 antibody as described herein conjugated to a drug or therapeutic agent for the treatment of a CD36-mediated disease or condition.

In some embodiments, an anti-CD36 antibody as described herein can be conjugated to an enzymatically active toxin or a fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins, *Momordica charantia* inhibitor, curcin, crotin, *Sapaonaria officinalis* inhibitor, gelonin, mitogellin, restrictocin, phenomycin, enomycin, and the tricothecenes.

In some embodiments, an immunoconjugate of the present disclosure comprises an anti-CD36antibody as described herein conjugated to a radioactive isotope (i.e., a radioconjugate). A variety of radioactive isotopes are available for the production of such radioconjugates. Examples include $^{211}$At, $^{131}$I, $^{125}$I, $^{90}$Y, $^{186}$Re, $^{188}$Re, $^{153}$Sm, $^{212}$Bi, $^{32}$P, $^{212}$Pb, and radioactive isotopes of Lu. In some embodiments, the immunoconjugate may comprise a radioisotope for scintigraphic detection, or a spin label for NMR detection or MRI. Suitable radioisotopes or spin labels can include, as $^{123}$I, $^{131}$I, $^{111}$In, $^{13}$C, $^{19}$F, $^{15}$N, $^{17}$O, various isotopes of Gd, Mn, and Fe.

Immunoconjugates of an anti-CD36 antibody and a cytotoxic agent, can be made using a variety of well-known bifunctional reagents and chemistries suitable for conjugating to proteins. Such reagents include but are not limited to: N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (e.g., dimethyl adipimidate HQ), active esters (e.g., disuccinimidyl suberate), aldehydes (e.g., glutaraldehyde), bis-azido compounds (e.g., bis-(p-azidobenzoyl)-hexanediamine), bis-diazonium derivatives (e.g., bis-(p-diazoniumbenzoyl)-ethylenediamine), diisocyanates (e.g., toluene-2,6-diisocyanate), and bis-active fluorine compounds (e.g., 1,5-difluoro-2,4-dinitrobenzene). Reagents for preparing immunoconjugates of the present disclosure can also include commercially available "cross-linking" reagents such as: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) (see e.g., Pierce Biotechnology, Inc., Rockford, IL., U.S.A).

III. Recombinant Methods and Compositions

The anti-CD36 antibody of the present disclosure can be produced using recombinant methods and materials well-known in the art of antibody production. In some embodiments, the present disclosure provides an isolated polynucleotide encoding an anti-CD36 antibody of the present disclosure, or a fragment, or a domain of an anti-CD36 antibody. For example, the isolated polynucleotide can encode an amino acid sequence comprising CDR or HVRs disclosed herein, an amino acid sequence comprising the $V_L$ domain and/or the $V_H$ domain of the antibody, or an amino acid sequence comprising a complete light chain and/or heavy chain of an anti-CD36 antibody. In at least one embodiment, an isolated polynucleotide can encode an amino acid sequence comprising CDR-H1, CDR-H2, and CDR-H3sequences, or an amino acid sequence comprising CDR-L1, CDR-L2, and CDR-L3 sequences of any of the anti-CD36 antibodies disclosure herein. Similarly, it is contemplated that an isolated polynucleotide can encode an amino acid sequence comprising a $V_L$ domain or the $V_H$ domain, or a complete heavy chain (HC) or light chain (LC) of an anti-CD36 antibody of the present disclosure.

In some embodiments, the present disclosure also provides vectors (e.g., expression vectors) comprising a polynucleotide sequence (as described above) that encodes an anti-CD36 antibody of the present disclosure or a fragment, or a domain of an anti-CD36 antibody. Such vector constructs comprising polynucleotides for the recombinant production of antibodies are well-known in the art. Further, in some embodiments, a host cell comprising a polynucleotide or vector with a sequence encoding an anti-CD36 antibody, or a fragment, or a domain of an anti-CD36 antibody of the present disclosure are provided. In at least one embodiment, the host cell is a cell that has been transformed with a vector comprising a polynucleotide sequence that encodes an amino acid sequence comprising the $V_L$ domain of the antibody and/or an amino acid sequence comprising the $V_H$ domain of an anti-CD36 antibody of the present disclosure. In another embodiment, the host cell has been transformed with a first vector comprising a polynucleotide sequence that encodes an amino acid sequence comprising the $V_L$ of the antibody and a second vector comprising a nucleic acid that encodes an amino acid sequence comprising the $V_H$ of the antibody.

In some embodiments of the recombinant methods, the host cell used is a eukaryotic cell, such as a Chinese Hamster Ovary (CHO) cell, or a lymphoid cell (e.g., Y0, NS0, Sp20). In one embodiment, a method of making an anti-CD36 antibody is provided, wherein the method comprises culturing a host cell comprising a nucleic acid encoding the antibody, as provided above, under conditions suitable for expression of the antibody, and optionally recovering the antibody from the host cell (or host cell culture medium).

Briefly, recombinant production of an anti-CD36 antibody is carried out by isolating a nucleic acid encoding an antibody (e.g., as described herein) and inserting this nucleic acid into one or more vectors for further cloning and/or expression in a host cell. Such nucleic acids are readily isolated and sequenced using conventional procedures well-known in the art (e.g., by using oligonucleotide probes that are capable of binding specifically to genes encoding the heavy and light chains of the desired antibody). Suitable host cells and culturing methods for cloning or expressing the antibody-encoding vectors are well-known in the art and include prokaryotic or eukaryotic cells. Typically, after expression, the antibody may be isolated from cell paste in a soluble fraction and further purified. In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern (see e.g., Gerngross, Nat. Biotech. 22: 1409-1414 (2004), and Li et al., Nat. Biotech. 24: 210-215 (2006)).

Suitable host cells for the expression of glycosylated anti-CD36 antibodies of the present disclosure can also be derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts (see, e.g., U.S. Pat. Nos. 5,959,177, 6,040,498, 6,420,548, and 7,125,978.

Examples of mammalian host cell lines useful for the production of the anti-CD36 antibodies of the present disclosure include Chinese hamster ovary (CHO) cells, including DHFR-CHO cells (see e.g., Urlaub et al., Proc. Natl. Acad. Sci. USA 77: 4216 (1980)); myeloma cell lines such as Y0, NS0 and Sp2/0; monkey kidney CV1 line transformed by SV40 (COS-7); human embryonic kidney line (293 or 293 cells as described, e.g., in Graham et al., J. Gen. Virol. 36: 59 (1977)); baby hamster kidney cells (BHK); mouse Sertoli cells (TM4 cells as described, e.g., in Mather, Biol. Reprod. 23: 243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TR1 cells (see e.g., in Mather et al., Annals N. Y. Acad. Sci. 383: 44-68 (1982) and U.S. Pat. No. 6,235,498); Medical Research Council 5 (MRC 5) cells (such as e.g., those available from ATCC and also referred to as CCL-171); and Foreskin 4 (FS-4) cells (see e.g., in Vilcek et al. Ann. N. Y. Acad. Sci. 284: 703-710 (1977), Gardner & Vilcek. J. Gen. Virol. 44: 161-168 (1979), and Pang et al. Proc. Natl. Acad. Sci. U.S.A. 77: 5341-5345 (1980)). For a general review of useful mammalian host cell lines suitable for antibody production, see, e.g., Yazaki and Wu, Methods in Molecular Biology, Vol. 248 (B.K.C. Lo, ed., Humana Press, Totowa, NJ), pp. 255-268 (2003).

IV. Pharmaceutical Compositions and Formulations of Anti-CD36 Antibodies

The present disclosure also provides pharmaceutical compositions and pharmaceutical formulations comprising an anti-CD36 antibody. In some embodiments, the present disclosure provides a pharmaceutical formulation comprising an anti-CD36 antibody as described herein and a pharmaceutically acceptable carrier. In some embodiments, the anti-CD36 antibody is the sole active agent of the pharmaceutical composition. Such pharmaceutical formulations can be prepared by mixing an anti-CD36 antibody, having the desired degree of purity, with one or more pharmaceutically acceptable carriers. Typically, such antibody formulations can be prepared as an aqueous solution (see e.g., U.S. Pat. No. 6,171,586, and WO2006/044908) or as a lyophilized formulation (see e.g., U.S. Pat. No. 6,267,958).

Pharmaceutically acceptable carriers are generally non-toxic to recipients at the dosages and concentrations employed. A wide range of such pharmaceutically acceptable carriers are well-known in the art (see e.g., Remington's Pharmaceutical Sciences 16th edition, Osol, A. Ed. (1980)). Exemplary pharmaceutically acceptable carriers useful in the formulations of the present disclosure can include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG).

Pharmaceutically acceptable carriers useful in the formulations of the present disclosure can also include interstitial drug dispersion agents, such as soluble neutral-active hyaluronidase glycoproteins (sHASEGP) (see e.g., US Pat. Publ. Nos. 2005/0260186 and 2006/0104968), such as human soluble PH-20 hyaluronidase glycoproteins (e.g., rHuPH20 or HYLENEX®, Baxter International, Inc.).

It is also contemplated that the formulations disclosed herein may contain active ingredients in addition to the anti-CD36, as necessary for the particular indication being treated in the subject to whom the formulation is administered. Preferably, any additional active ingredient has activity complementary to that of the anti-CD36 antibody activity and the activities do not adversely affect each other.

In some embodiments, the pharmaceutical composition comprises the anti-CD36 antibody and an additional active agent for cancer treatment such as an immune checkpoint inhibitor. Checkpoint inhibitors useful in such embodiments include, but are not limited to, a second antibody comprising a specificity for an antigen that is an immune checkpoint molecule. In some embodiments, the second antibody comprises a specificity for an immune checkpoint molecule selected from PD1, PD-L1, LAG3, CTLA-4, A2AR, TIM-3, BTLA, CD276, CD328, VTCN1, IDO, KIR, NOX2, VISTA, OX40, CD27, CD28, CD40, CD122, CD137, GITR, ICOS. In at least one embodiment, the pharmaceutical composition comprising an anti-CD36 antibody and an additional active agent, wherein the additional active agent is an antibody comprising a specificity for the immune checkpoint molecule PD1. Exemplary antibodies comprising a specificity for PD1 that are useful in the pharmaceutical composition embodiments disclosed herein include, but are not limited to, dostarlimab, pembrolizumab, nivolumab, and pidilizumab.

It is also contemplated that in some embodiments the present disclosure provides pharmaceutical composition or formulation for use in therapy, wherein the composition further comprises a T-cell activating cytokine or an immunostimulatory cytokine. Such cytokines are well known in the art of immunotherapy, and include, but are not limited to, IL-2, IL-7, IL-10, IL-12, IL-15, IL-21, and IFN-α. In at least one embodiment, the immunostimulatory cytokine can be provided in the composition as a fusion of the anti-CD36 antibody.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

In some embodiments, the formulation can be a sustained-release preparation of the antibody and/or other active ingredients. Suitable examples of sustained-release preparations include semipermeable matrices of solid hydrophobic polymers containing the antibody, which matrices are in the form of shaped articles, e.g. films, or microcapsules.

Typically, the formulations of the present disclosure to be administered to a subject are sterile. Sterile formulations may be readily prepared using well-known techniques, e.g., by filtration through sterile filtration membranes.

V. Uses and Methods of Treatment

It is contemplated that any of the compositions or formulations comprising an anti-CD36 antibody of the present disclosure can be used for any methods or uses, such as in therapeutic methods that utilize their ability to specifically bind to CD36 and thereby inhibit, decrease, and/or fully block the function of CD36 as a cell surface protein involved in immune regulation or signaling, particularly the function of CD36 regulating uptake of lipoproteins, fatty acids, and other ligands involved in the survival and maintenance or survival (or death, as the case may be) of tumor cells, tumor-associated macrophages (TAMs), myeloid-derived suppressor cells (MDSCs), regulatory T cells and CD8 T cells. Regulatory T cells, for example, are a major cellular component of tumor microenvironment (TME), and contribute significantly to tumor growth and progression while CD8 T cells help to control tumor growth by killing tumor cells. Inhibition of CD36 binding can deplete regulatory T cells while at the same time increasing CD8 T cell survival and function, thereby inducing an increase in anti-tumor T-cell response.

There are a range of diseases, disorders, and conditions that can potentially be treated by inhibiting, decreasing, and/or fully blocking the immune regulatory and/or immune signaling activity of CD36, particularly, the effect of CD36 on TAMs. Diseases, disorders, and conditions include, but are not limited to, cancers, including but not limited to colon cancer, pancreatic cancer, ovarian cancer, HCC, renal cancer, breast cancer, lung cancer, gastric cancer, melanoma, head and neck cancer, or oral cancer. It is contemplated that any of the compositions or formulations comprising an anti-CD36 antibody of the present disclosure can be used for a method or use for the treatment of any of the above-listed cancers. In some embodiments, the cancer is selected from colon cancer, pancreatic cancer, ovarian cancer, HCC, renal cancer, breast cancer, lung cancer, gastric cancer, melanoma, head and neck cancer, or oral cancer. In some embodiments, the present disclosure provides a method of treating cancer in a subject, the method comprising administering to the subject in need thereof a therapeutically effective amount of an anti-CD36 antibody of the present disclosure or administering to a subject a therapeutically effective amount of a pharmaceutical composition comprising an anti-CD36 antibody of the present disclosure and a pharmaceutically acceptable carrier.

As disclosed herein, including in the Examples below, the anti-CD36 antibodies of the present disclosure have the ability to decrease, inhibit, and/or block binding of ligands to CD36, and thereby alter the immune signaling pathways mediated by CD36. Accordingly, in some embodiments, the present disclosure provides a method of treating a CD36-mediated disease or condition in a subject, the method comprising administering to the subject a therapeutically effective amount of an anti-CD36 antibody of the present disclosure or administering to a subject in need thereof a therapeutically effective amount of a pharmaceutical composition comprising an anti-CD36 antibody of the present disclosure and a pharmaceutically acceptable carrier. Similarly, in some embodiments, the present disclosure provides a method of treating a disease mediated by binding to CD36 expressed on cells in a subject, the method comprising administering to the subject, the method comprising administering to the subject a therapeutically effective amount of an anti-CD36 antibody of the present disclosure or administering to a subject in need thereof a therapeutically effective amount of a pharmaceutical composition comprising an anti-CD36 antibody of the present disclosure and a pharmaceutically acceptable carrier.

Administration of the anti-CD36 antibody, composition, or pharmaceutical formulation in accordance with the method of treatment provides an antibody-induced therapeutic effect that protects the subject from and/or treats the progression of a CD36-mediated disease in a subject. In some embodiments, the method of treatment can further comprise administration of one or more additional therapeutic agents or treatments known to those of skill in the art to prevent and/or treat the CD36-mediated disease or condition. Such methods comprising administration of one or more additional agents can encompass combined administration (where two or more therapeutic agents are included in the same or separate formulations), and separate administration, in which case, administration of the antibody composition or formulation can occur prior to, simultaneously, and/or following, administration of the additional therapeutic agent.

In some embodiments of the methods of treatment of the present disclosure, the anti-CD36 antibody or pharmaceutical formulation comprising an anti-CD36 antibody is administered to a subject by any mode of administration that delivers the agent systemically, or to a desired target tissue. Systemic administration generally refers to any mode of administration of the antibody into a subject at a site other than directly into the desired target site, tissue, or organ, such that the antibody or formulation thereof enters the subject's circulatory system and, thus, is subject to metabolism and other like processes.

Accordingly, modes of administration useful in the methods of treatment of the present disclosure can include, but are not limited to, injection, infusion, instillation, and inhalation. Administration by injection can include intravenous, intramuscular, intraarterial, intrathecal, intraventricular, intracapsular, intraorbital, intracardiac, intradermal, intraperitoneal, transtracheal, subcutaneous, subcuticular, intraarticular, subcapsular, subarachnoid, intraspinal, intracerebro spinal, and intrasternal injection and infusion.

In some embodiments, a pharmaceutical formulation of the anti-CD36 antibody is formulated such that the antibody is protected from inactivation in the gut. Accordingly, the method of treatments can comprise oral administration of the formulation.

In some embodiments, use of the compositions or formulations comprising an anti-CD36 antibody of the present disclosure as a medicament are also provided. Additionally, in some embodiments, the present disclosure also provides for the use of a composition or a formulation comprising an anti-CD36 antibody in the manufacture or preparation of a medicament, particularly a medicament for treating, preventing or inhibiting a CD36-mediated disease. In a further embodiment, the medicament is for use in a method for treating, preventing or inhibiting a CD36-mediated disease comprising administering to an individual having a CD36-mediated disease an effective amount of the medicament. In certain embodiments, the medicament further comprises an effective amount of at least one additional therapeutic agent, or treatment.

In at least one embodiment, it is contemplated that the additional therapeutic agents or treatments that can be used in such medicaments with anti-CD36 antibodies of the present disclosure can include but are not limited to therapeutic antibodies comprising a specificity for an immune checkpoint molecule such as PD1, PD-L1, LAG3, CTLA-4, A2AR, TIM-3, BTLA, CD276, CD328, VTCN1, IDO, KIR, NOX2, VISTA, OX40, CD27, CD28, CD40, CD122, CD137, GITR, ICOS. Exemplary antibodies comprising a specificity for an immune checkpoint molecule include, but are not limited to an anti-PD1 antibody selected from dostarlimab, pembrolizumab, nivolumab, and pidilizumab.

In a further embodiment, the medicament is for use in treating, inhibiting or preventing a CD36-mediated disease, such as a cancer, in a subject comprising administering to the subject an amount effective of the medicament to treat, inhibit or prevent the CD36-mediated disease.

The appropriate dosage of the anti-CD36 antibody contained in the compositions and formulations of the present disclosure (when used alone or in combination with one or more other additional therapeutic agents) will depend on the specific disease or condition being treated, the severity and course of the disease, whether the antibody is administered for preventive or therapeutic purposes, the previous therapy administered to the patient, the patient's clinical history and response to the antibody, and the discretion of the attending physician. The anti-CD36 antibody included in the compositions and formulations described herein, can be suitably administered to the patient at one time, or over a series of treatments. Various dosing schedules including but not limited to single or multiple administrations over various timepoints, bolus administration, and pulse infusion are contemplated herein.

Depending on the type and severity of the disease, about 1 μg/kg to 15 mg/kg of anti-CD36 antibody in a formulation of the present disclosure is an initial candidate dosage for administration to a human subject, whether, for example, by one or more separate administrations, or by continuous infusion. Generally, the administered dosage of the antibody would be in the range from about 0.05mg/kg to about 10 mg/kg. In some embodiments, one or more doses of about 0.5 mg/kg, 2.0 mg/kg, 4.0 mg/kg or 10 mg/kg (or any combination thereof) may be administered to a patient.

Dosage administration can be maintained over several days or longer, depending on the condition of the subject, for example, administration can continue until the CD36-mediated disease is sufficiently treated, as determined by methods known in the art. In some embodiments, an initial higher loading dose may be administered, followed by one or more lower doses. However, other dosage regimens may be useful. The progress of the therapeutic effect of dosage administration can be monitored by conventional techniques and assays.

Accordingly, in some embodiments of the methods of the present disclosure, the administration of the anti-CD36 antibody comprises a daily dosage from about 1 mg/kg to about 100 mg/kg. In some embodiments, the dosage of anti-CD36 antibody comprises a daily dosage of at least about 1 mg/kg, at least about 5 mg/kg, at least about 10 mg/kg, at least about 20 mg/kg, or at least about 30 mg/kg.

EXAMPLES

Various features and embodiments of the disclosure are illustrated in the following representative examples, which are intended to be illustrative, and not limiting. Those skilled in the art will readily appreciate that the specific examples are only illustrative of the invention as described more fully in the claims which follow thereafter. Every embodiment and feature described in the application should be understood to be interchangeable and combinable with every embodiment contained within.

Example 1: Anti-CD36 Antibody Generation and CD36 Binding Analysis

This example illustrates the use of phage-displayed antibody library technology to generate exemplary anti-CD36 antibodies of the present disclosure that specifically bind to human and mouse CD36.

A. Selection of Anti-CD36 scFv Binders from Phage-Displayed Antibody libraries The panning procedure is briefly described below. First, human CD36.ECD antigen (5 μg per well, Sino Biological) in PBS buffer (pH 7.4) was coated onto 96-well plate (NUNC Maxisorb immunoplate) wells overnight at 4° C. and then blocked with 5% skim milk in PBST [0.1% (v/v) Tween 20] for 1 h. After blocking, 100 μL concentrated phage library (1013 cfu/mL in PBS buffer) was mixed with 100 μL blocking buffer, and then added to each well for 1 h under gentle shaking. The plate was washed 12 times with PBST and 3 times with PBS. The bound phages were eluted with 100 μL of 0.1 M HCl/glycine (pH 2.2) per well and then immediately neutralized with 20 μL of 1 M Tris-base buffer (pH 9.0). The eluted phages were mixed with 1 mL of *E. coli* ER2738 (A600 nm=0.6) for 30 min at 37° C.; uninfected bacteria were eliminated by adding ampicillin. After ampicillin treatment for 30 minutes, the bacterial culture was infected with 100 μL M13KO7 helper phage (~1011 CFU total) at 37° C. for 1 h and then added to 50 mL of 2× YT medium containing kanamycin 50 μg/mL and ampicillin 100 μg/mL overnight at 37° C. with vigorous shaking. The rescued phage library was precipitated with 20% polyethylene glycol/NaCl and resuspended in PBS. The concentrated phage solution was used for the next round of panning.

After 3~4 rounds of selection-amplification cycle, single colonies were randomly selected into deep 96 well culture plate (plate A; secreted scFv); each well contained 950 μL 2YT (100 μg/mL ampicillin). After 3 h incubation at 37° C. with shaking, 50 μL of bacterial culture was transferred to the corresponding well of a fresh deep 96-well plate (plate B; phage form); each well contained 0.8 mL 2YT with 100 μg/mL ampicillin. In the meantime, 50 μL M13KO7 (~5×1010 CFU total) was added to each well of plate B. After 1 h incubation, 100 μL 2YT containing IPTG (10 mM) was added to each well of plate A; 100 μL 2YT containing kanamycin (500 μg/mL) was added to each well of plate B. After overnight incubation at 37° C. with vigorous shaking, the cultures were centrifuged at 3000 g for 10 min at 4° C. The plate B was stored for further sequencing determination. For secreted scFv culture plate (plate A), 100 μL culture medium and 100 μL 5% PBST milk was added to a corresponding well of three 96-well plates pre-coated with protein L (0.1 μg/well), human CD36 (0.5~1 μg/well) and bovine serum albumin (BSA) (2 μg/well), respectively and blocked with 5% PBST milk. After 1 h incubation at room temperature, the plates were washed three times with PBST. 100 μL Protein A-HRP (Thermo Scientific) was added to each well of Protein L-coated immunoplate; 100 μL anti-E-tag-HRP (ICL Inc.) was added to each well of human CD36 antigen-coated and BSA-coated plates. After 1 h incubation, the plates were washed three times with PBST buffer and twice with PBS, developed for 3 min with 3,3',5,5'-tetramethyl-benzidine peroxidase substrate (Kirkegaard & Perry Laboratories), quenched with 1.0 M HCl and read spectrophotometrically at 450 nm.

Positive clones were selected by the following criteria: ELISA OD450>0.2 for the human CD36 antigen-coated well (antigen binding positive); OD450<0.05 for BSA-coated well (non-specific binding negative); OD450>0.5 for the Protein L-coated well (soluble scFv binding to both Protein L and Protein A to ensure proper folding in solution), and then subjected to DNA sequencing. The polynucleotide sequence of scFv of the exemplary anti-CD36 antibody 12P109 (SEQ ID NO: 1) obtained from phage display panning is provided in Table 2 and the accompanying Sequence Listing. Further panning of a phage display library composed of "shuffled" LC sequences derived from different anti-CD36 antibodies and the HC sequence of 12P109 provided the scFv of the exemplary anti-CD36 antibody A8A (SEQ ID NO: 10), also listed in Table 2 and the accompanying Sequence Listing. Standard PCR-based mutagenesis was carried out on the CDRs of the A8A antibody VL domain (SEQ ID NO: 11) were further subjected to provide the exemplary anti-CD36 antibody VL domain of A8A-N52T (SEQ ID NO: 14), also listed in Table 2 and the accompanying Sequence Listing.

B. Generation of Anti-CD36 Antibodies in Full-Length IgG Format scFv reformatting and cloning: The CD36 binding determinants of the scFvs selected from phage display panning were reformatted into full-length IgG antibodies by cloning the $V_H$ and $V_L$ domains of the fragments into the human IgG1-N297A heavy chain vector and the human kappa light chain vector using the restriction sites MluI/NheI and BsiWI/DraIII, respectively. $V_H$ and $V_L$ domains were amplified using the following forward and reverse oligonucleotide primer pairs: (1) PhageLib_VL_Fw: 5'-AATCACgATgTgATATTCAAATgACCCAgAgCCCgAgC-3' (SEQ ID NO: 64), (2) PhageLib_VL_Rv: 5'-AATCgTACgTTTgATTTCCACTTTggTgCCTTg-3' (SEQ ID NO: 65), (3) PhageLib_VH_Fw: 5'-AATACgCgTgTCCTgTCCgAAgTgCAgCTggTggAATCg-3' (SEQ ID NO: 66), and (4) PhageLib_VH_Rv: 5'-AATgCTAgCCgAgCTCACggTAACAAg-3' (SEQ ID NO: 67).

Expression and purification of full-length antibodies: The vectors cloned with the reformatted anti-CD36 antibody genes were transiently expressed in ExpiCHO-S cells (Thermo Scientific). During exponential growth phase, ExpiCHO-S cells were diluted to a final density of $6\times10^6$ cells/mL with ExpiCHO Expression Medium. ExpiFectamine CHO/plasmid DNA complexes were prepared using cold reagents according to the manual, incubated at room temperature for 1-5 minutes, and then slowly added to cells. One day after transfection, the culture was supplemented with ExpiFectamine CHO Enhancer and incubated for another 7 days. Transfected cell supernatants were centrifuged and subsequently filtered through a 0.22 μm filter. Antibodies were purified from the transfected cell supernatants with Protein A beads (Cytiva, 17127903). Antibody loaded columns were washed with 50 column volumes of PBS, and then eluted with 10 beads volume of 0.1 M Glycine (pH 3) directly into 1⁄10 volume of 1M Tris buffer (pH 9.0). The eluent was buffer-exchanged and concentrated with PBS, pH 7.4 containing 0.1M Arginine. The quality of purified anti-CD36 antibodies was determined using SDS-PAGE in the presence and absence of a reducing agent.

Results: Examination of SDS-PAGE images showed that the expression and purification resulted in purified full-length anti-CD36 antibodies.

C. Optimization of Anti-CD36 Antibodies

To further improve the druggability of the anti-CD36 antibody A8A, two phage display libraries composed of mutations on N52, H91 and L94 were used for panning. The scFv clone 117 selected from phage display panning was reformatted into full-length IgG antibodies by cloning the $V_H$ and $V_L$ domains of the fragments into the human IgG1-N297A heavy chain vector and the human kappa light chain vector using the restriction sites MluI/NheI and BsiWI/DraIII, respectively. $V_H$ and $V_L$ domains were amplified using the following forward and reverse oligonucleotide primer pairs: (1) PhageLib_VL_Fw: 5'-AATCACgATgTgA-TATTCAAATgACCCAgAgCCCgAgC-3' (SEQ ID NO: 64), (2) PhageLib_VL_Rv: 5'-AATCgTACgTTTgATTTC-CACTTTggTgCCTTg-3' (SEQ ID NO: 65), (3) PhageLib_VH_Fw: 5'-AATACgCgTgTCCTgTCCgAAgTgCAgCTggTg-gAATCg-3' (SEQ ID NO: 66), and (4) PhageLib_VH_Rv: 5'-AATgCTAgCCgAgCTCACggTAACAAg-3' (SEQ ID NO: 67).

The 117 antibody shares the same CDR-H1, H2, H3, and CDR-L1 sequences as A8A, and has a N52T mutation in CDR-L2, and a L94A mutation in CDR-L3. The Fab fragment of 117 antibody was also constructed into human IgG4-S228P/F234A/L235A heavy chain vector using the restriction sites NheI and BamHI. CDRs of the VH and VL domains of the 117 antibody were subjected to further PCR-based mutagenesis to generate a series of variants as summarized in Table 3 below.

TABLE 3

| 117 Variant | $V_H$ | | | | | | | | $V_L$ |
|---|---|---|---|---|---|---|---|---|---|
| | CDR-H1 | | | | CDR-H2 | | | CDR-H3 | CDR-L3 |
| Name | T28 | S30 | S31 | F32 | Y54 | Y57 | T58 | F101 | S92 |
| | Single Mutation Variants | | | | | | | | |
| 117_28A | A | | | | | | | | |
| 117_28D | D | | | | | | | | |
| 117_30A | | A | | | | | | | |
| 117_30D | | D | | | | | | | |
| 117_31A | | | A | | | | | | |
| 117_31D | | | D | | | | | | |
| 117_32A | | | | A | | | | | |
| 117_32D | | | | D | | | | | |
| 117_54E | | | | | E | | | | |
| 117_57A | | | | | | A | | | |
| 117_57D | | | | | | D | | | |
| 117_57E | | | | | | E | | | |
| 117_57R | | | | | | R | | | |
| 117_57T | | | | | | T | | | |
| 117_58E | | | | | | | E | | |
| 117_101A | | | | | | | | A | |
| 117_101D | | | | | | | | D | |
| 117_101H | | | | | | | | H | |
| 117_101K | | | | | | | | K | |
| 117_101S | | | | | | | | S | |
| 117_101Y | | | | | | | | Y | |
| 117_92A | | | | | | | | | A |
| 117_92E | | | | | | | | | E |
| | Double Mutations | | | | | | | | |
| 117_30AA | | A | A | | | | | | |
| 117_30AT | | A | T | | | | | | |
| 117_30DA | | D | A | | | | | | |
| 117_30DT | | D | T | | | | | | |
| 117_30DE | | D | | | | E | | | |
| 117_30FA | | F | A | | | | | | |
| 117_30FT | | F | T | | | | | | |
| 117_31AD | | | A | D | | | | | |
| 117_31AT | | | A | T | | | | | |
| 117_57DE | | | | | | D | E | | |
| 117_57EE | | | | | | E | E | | |
| | Triple Mutations | | | | | | | | |
| 117_AA57D | | A | A | | | D | | | |
| 117_AA57E | | A | A | | | E | | | |

TABLE 3-continued

| 117 Variant Name | $V_H$ CDR-H1 T28 | S30 | S31 | F32 | CDR-H2 Y54 | Y57 | T58 | CDR-H3 F101 | $V_L$ CDR-L3 S92 |
|---|---|---|---|---|---|---|---|---|---|
| 117_DA57D | | D | A | | | D | | | |
| 117_DA57E | | D | A | | | E | | | |

The 117 antibody and variants were expressed and purified as full-length antibodies as described above. Examination of SDS-PAGE images showed that the expression and purification resulted in purified full-length anti-CD36 antibodies. Amino acid sequences of the CDRs, VH, VL, HC, LC regions of the 117 antibody and the exemplary variants 117_30AA, 117_30DA, 117_57D, 117_57E, and 117_DA57E, also listed in Table 2 and the accompanying Sequence Listing.

D. ELISA of CD36-Specific Binding by Anti-CD36 Antibodies

ELISA materials and methods: Recombinant His-tagged human CD36.ECD protein or His-tagged mouse CD36.ECD protein (both from Sino Biological) was immobilized on 96 well microtiter plate at a concentration of 1 μg/mL in Coating Solution (SeraCare) overnight at 4° C. The wells were washed with wash solution (0.05% Tween20 in PBS) and blocked with 1% BSA in PBS. Serial dilutions of anti-CD36 antibodies were added to wells. After incubation at 37° C. for 1 h, the wells were washed with wash solution. Peroxidase-conjugated Goat anti-human kappa Light chain antibody (Sigma) was applied to each well at 37° C. for 1 h incubation. After washing, the wells were developed with TMB substrate for 5-10 min at room temperature and then stopped with 1 N HCl. Thereafter absorbance was measured at 450 nm and 650 nm. EC50 values were calculated through GraphPad Prism7.

Figure 1B:
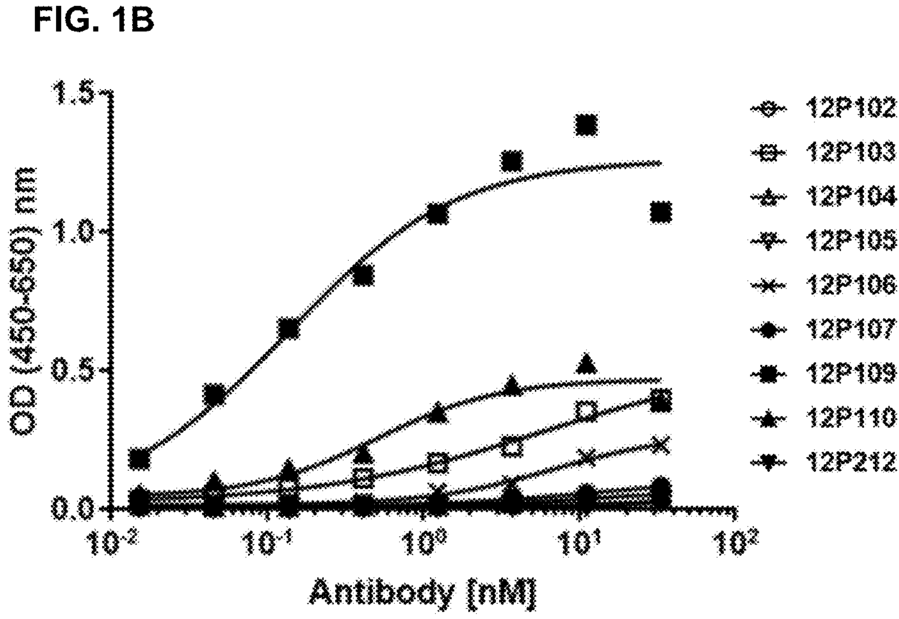

Results: ELISA data plots showing binding to either human CD36.ECD or mouse CD36.ECD are depicted in FIG. 1A and FIG. 1B, respectively, for the full-length IgG anti-CD36 antibody 12P109, and additional positive clones, 12P102, 12P103, 12P104, 12P105, 12P106, 12P107, 12P110 and 12P212. Binding curves for the antibodies labeled 12P109, 12P103, and 12P212 showed the highest affinity for human CD36 (hCD36, see FIG. 1A). 12P109 also showed high binding affinity for mouse CD36 (mCD36, see FIG. 1B). The EC50 values calculated from the ELISA data are shown in Table 4 below.

TABLE 4

| mAb | $EC_{50}$ (nM) hCD36 | mCD36 |
|---|---|---|
| 12P102 | >1000 | NA |
| 12P103 | 0.222 | 5.987 |
| 12P104 | 0.688 | 9.182 |
| 12P105 | 3.907 | >400 |
| 12P106 | 3.87 | 6.81 |
| 12P107 | 2.246 | 11.87 |
| 12P109 | 0.213 | 0.137 |
| 12P110 | 74.62 | 0.508 |
| 12P212 | 4.217 | >500 |

ELISA data plots showing binding of anti-CD36 antibodies to recombinant human CD36.ECD or mouse CD36.ECD coated on ELISA plates are depicted in FIG. 1C and 1D, respectively. This employed full-length human IgG1-format anti-CD36 antibodies 12P109 and A8A, and the commercial mouse IgA antibody, D2712 (clone CRF D-2712, BD Biosciences, US) that specifically binds CD36. EC50 values derived from the curves of FIG. 1C and FIG. 1D are shown in Table 5 below.

TABLE 5

| mAb | $EC_{50}$ (nM) hCD36 | mCD36 |
|---|---|---|
| 12P109 | 43.24 | 9.45 |
| A8A | 5.17 | 0.94 |
| D2712 | >500 | 0.93 |

ELISA data plots showing binding to human CD36.ECD are depicted in FIG. 2A, FIG. 2B, FIG. 2C, FIG. 2D, FIG. 2E, and FIG. 2F, for the full-length IgG anti-CD36 antibodies, 12P109, 117, and the various 117 variants listed in Table 3. The competitor anti-CD36 antibody ONA, which is derived from clone "ONA-0-v1" as disclosed in WO2021176424A1 in hIgG4-S228P-FALA format. The EC50 values calculated from the ELISA data of FIGS. 2A-2F are shown in Table 7 below.

TABLE 7

Figures 2C, 2D:
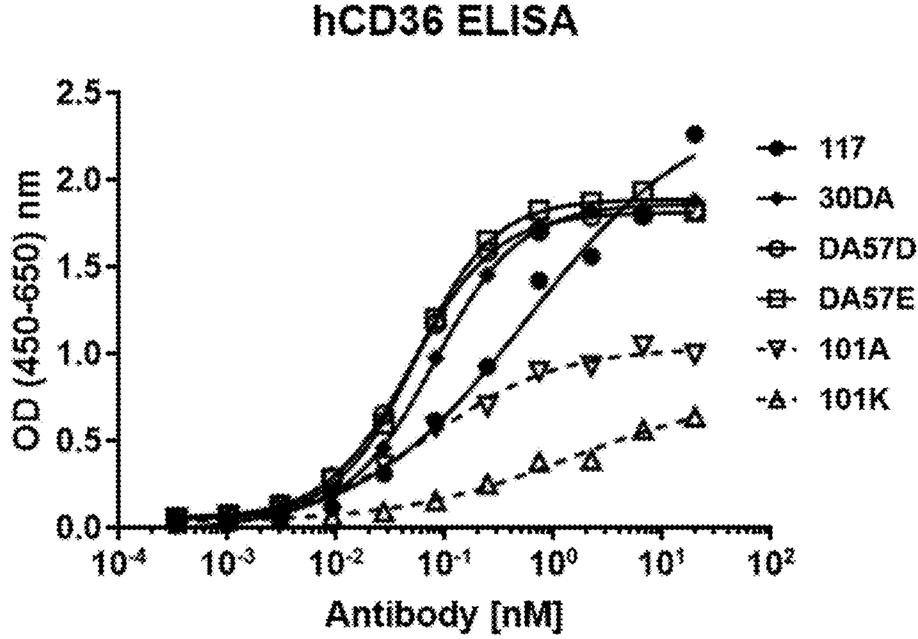
Figure 2E:
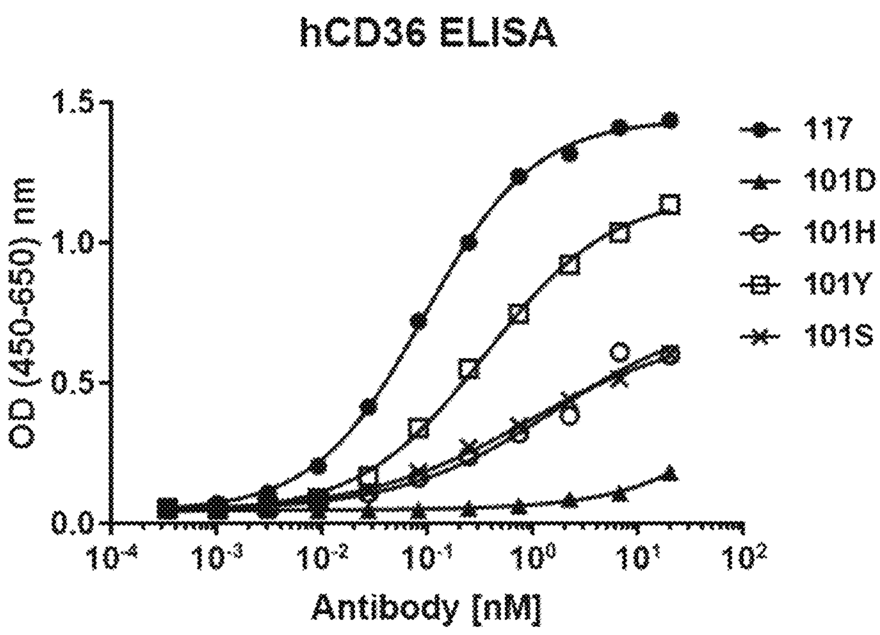
Figure 2F:
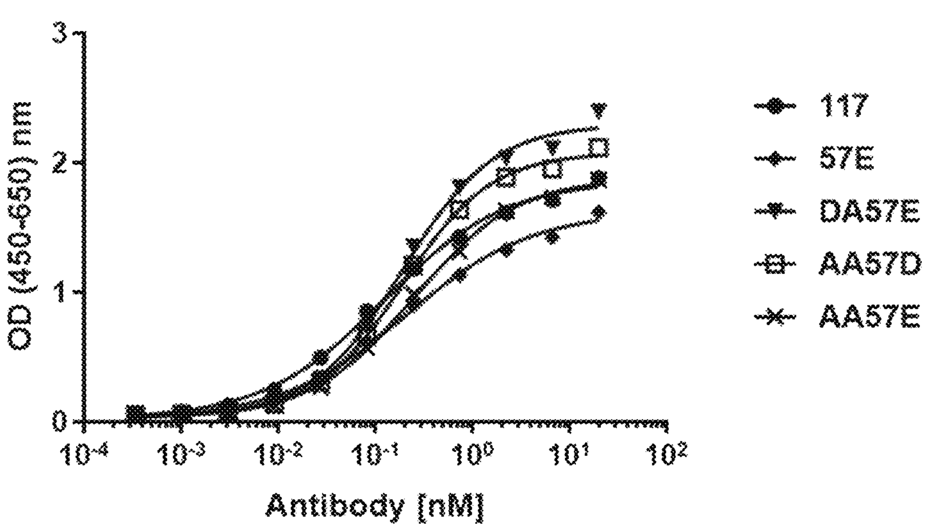

| mAb | hCD36 $EC_{50}$ (nM) | mAb | hCD36 $EC_{50}$ (nM) |
|---|---|---|---|
| FIG. 2A | | FIG. 2D | |
| 12P109 | 1.53 | 117 | 0.571 |
| 117 | 0.0475 | 117_30DA | 0.0803 |
| 117_57D | 0.0529 | 117_DA57D | 0.0490 |
| 117_57E | 0.0492 | 117_DA57E | 0.0539 |
| 117_57R | 0.0695 | 117_101A | 0.0751 |
| 117_57A | 1.52 | 117_101K | 1.46 |
| 117_57T | NA | ONA | 0.167 |
| 117_58E | 0.422 | | |
| FIG. 2B | | FIG. 2E | |
| 117 | 0.102 | 117 | 0.0932 |
| 117_28A | 0.129 | 117_101D | NA |
| 117_28D | 0.0735 | 117_101H | 1.60 |
| 117_30A | 0.0964 | 117_101Y | 0.355 |
| 117_30D | 0.141 | 117_101S | 0.929 |
| 117_31A | 0.0991 | | |
| 117_31D | 0.0375 | | |
| 117_32D | 0.0276 | | |
| FIG. 2C | | FIG. 2F | |
| 117 | 0.571 | 117 | 0.124 |
| 117_30AA | 0.145 | 117_57E | 0.206 |
| 117_30AT | 0.247 | 117_DA57E | 0.190 |

TABLE 7-continued

| mAb | hCD36 $EC_{50}$ (nM) | mAb | hCD36 $EC_{50}$ (nM) |
|---|---|---|---|
| 117_30DA | 0.137 | 117_AA57D | 0.192 |
| 117_30DT | 0.103 | 117_AA57E | 0.251 |
| 117_30FA | 0.202 | | |
| 117_30FT | 0.254 | | |

F. SEC-UPLC Analysis

Extended retention time (RT) of an antibody as determined by SEC-UPLC analysis may be associated with non-specific hydrophobic interactions that create a risk for development of the antibody for therapeutic uses. Accordingly, the anti-CD36 antibodies, 12P109, A8A, 117, and the 117 variants, as well as an IgG standard ("STD", BEH200 SEC Protein Standard Mix) and control monoclonal antibody ("ctl Ab") were analyzed by SEC-UPLC for increased RT indicating formation of protein aggregates.

Materials and methods: After protein A purification, the anti-CD36 antibodies, 12P109, A8A, 117, and the 117 variants were analyzed for protein aggregates and retention time by standard Size Exclusion UPLC (SEC-UPLC). 3 μg of antibody was applied to an UPLC (Waters ARC UPLC) and separation was accomplished on a gel filtration column (Waters, XBridge BEH450 SEC 4.6×150) using a mobile phase of PBS. The antibody peak was monitoring UV absorbance at 280 and the peak area was determined using Empower software.

Results: Plots of SEC-UPLC results are shown in FIG. 3A, FIG. 3B, FIG. 3C, and FIG. 3D along with determined RT values. The control antibody exhibited a RT value of 7.243 min, whereas the anti-CD36 antibodies, 12P109 and 117 both exhibited relatively increased RT values. The increased RT values of 117, however, was decreased significantly by the mutations present in the variants, 117_30DA, 117_31AD, 117_57D, 117_57E, 117_57EE, 117_101D, and 117_DA57E. The RT values of anti-CD36 antibodies as determined in SEC-UPLC experiments are provided in Table 8 below. In addition, some aggregates were found in 117_DA57E by UPLC analysis. Aggregates may be related to the fact that 117_DA57E is less stable to acidic elution conditions. R409K mutation in IgG4 has been shown to increase CH3 domain interaction strength and reduce tendency to aggregate at low pH. The SEC-UPLC analysis showed that R409K addition to 117_DA57E reduced aggregation caused by acidic condition.

TABLE 8

Figure 3A:
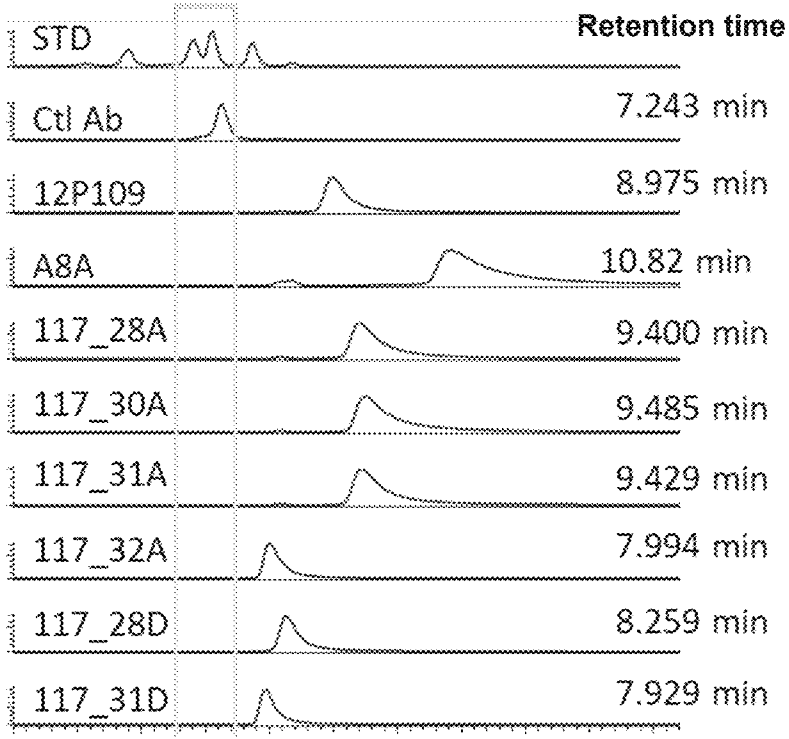
FIG. 3A, FIG. 3B, FIG. 3C, and FIG. 3D depict plots showing results from SEC-UPLC analysis of anti-CD36 antibodies (12P109, A8A, and 117 variants) as described in Example 1.
Figure 3B:
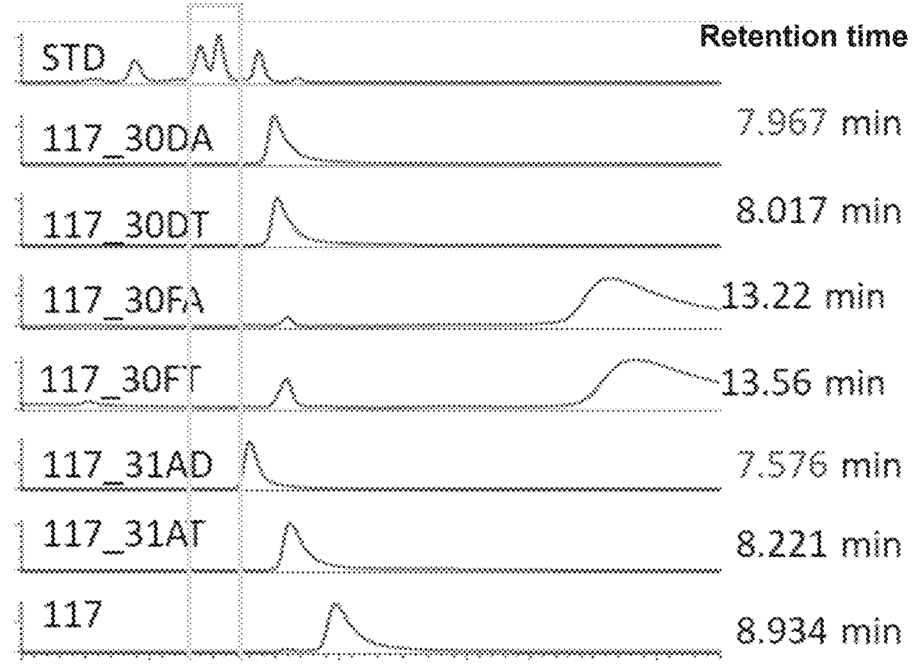
Figure 3C:
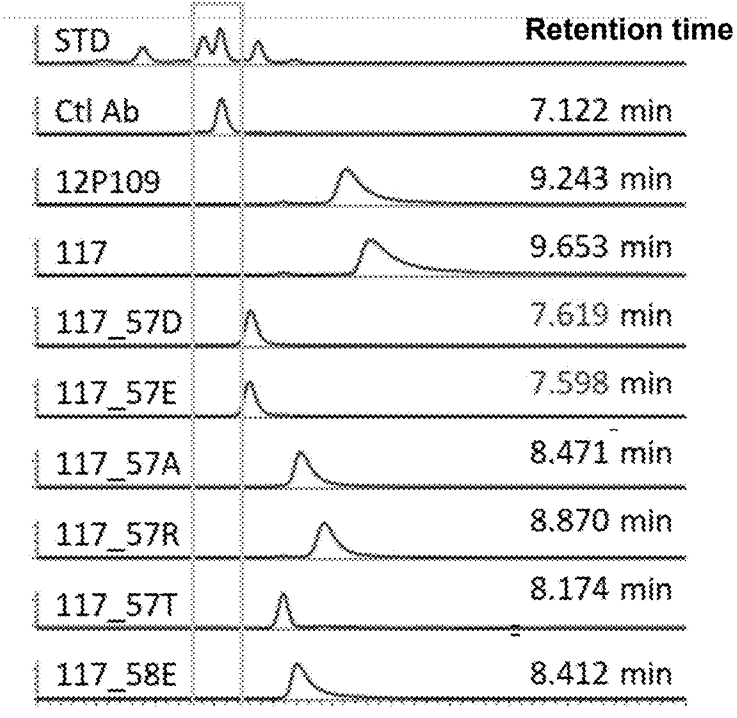

| mAb | Retention time | mAb | Retention time |
|---|---|---|---|
| FIG. 3A | | FIG. 3C | |
| STD IgG | 6.81 min | STD IgG | 6.81 min |
| Ctl Ab | 7.24 min | Ctl Ab | 7.12 min |
| 12P109 | 8.98 min | 12P109 | 9.24 min |
| A8A | 10.82 min | 117 | 9.65 min |
| 117_28A | 9.40 min | 117_57D | 7.62 min |
| 117_30A | 9.49 min | 117_57E | 7.60 min |
| 117_31A | 9.43 min | 117_57A | 8.47 min |
| 117_32A | 7.99 min | 117_57R | 8.87 min |

TABLE 8-continued

Figure 3D:
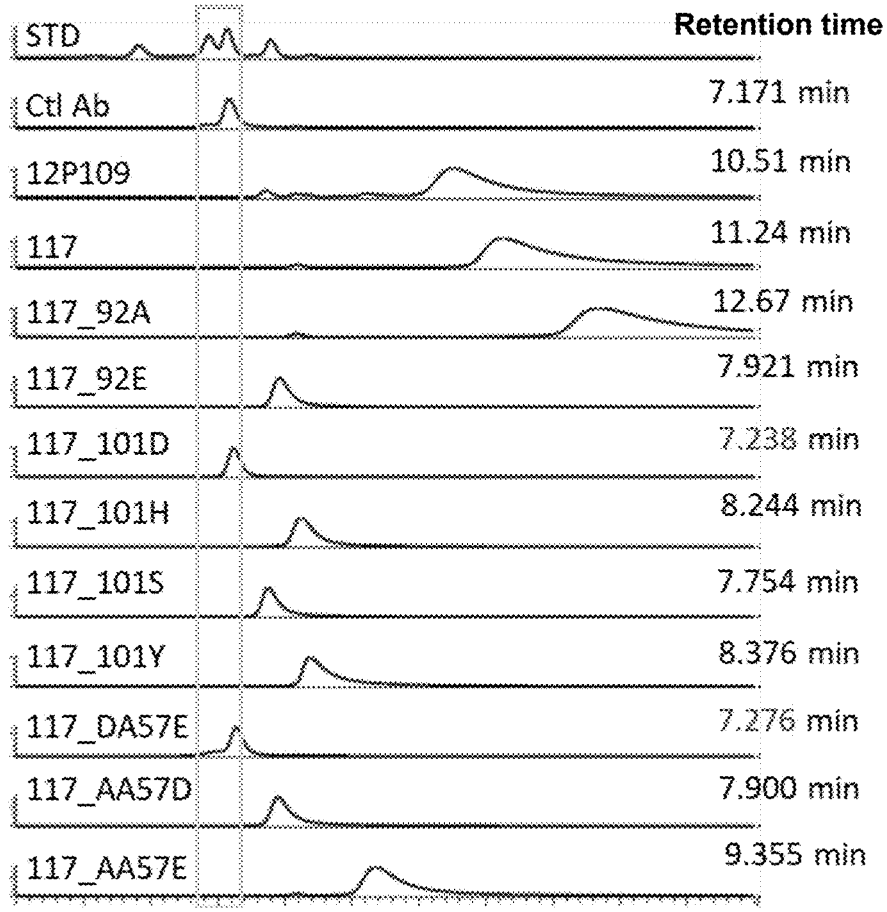
Figure 4A:
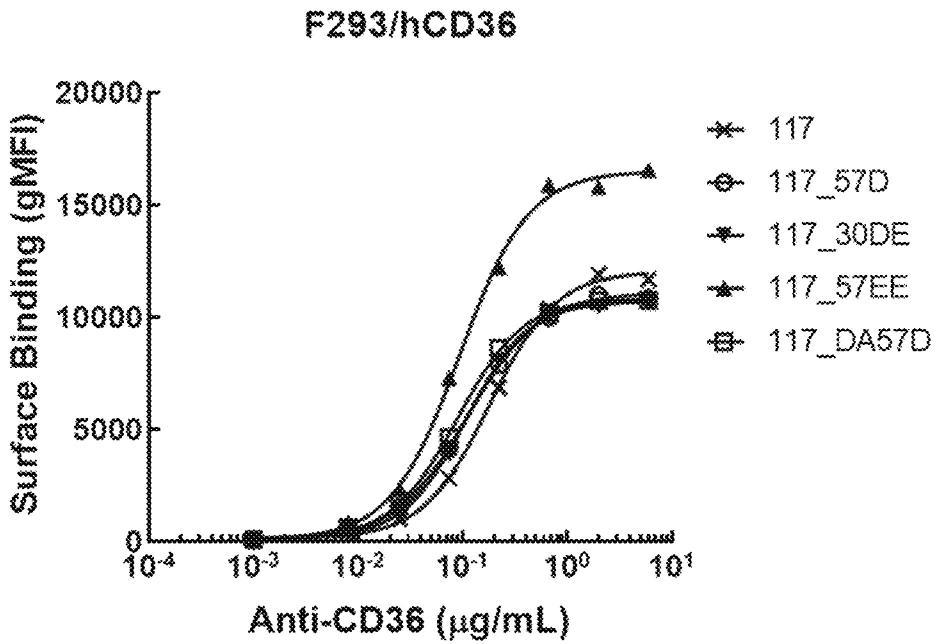
Figure 4B:
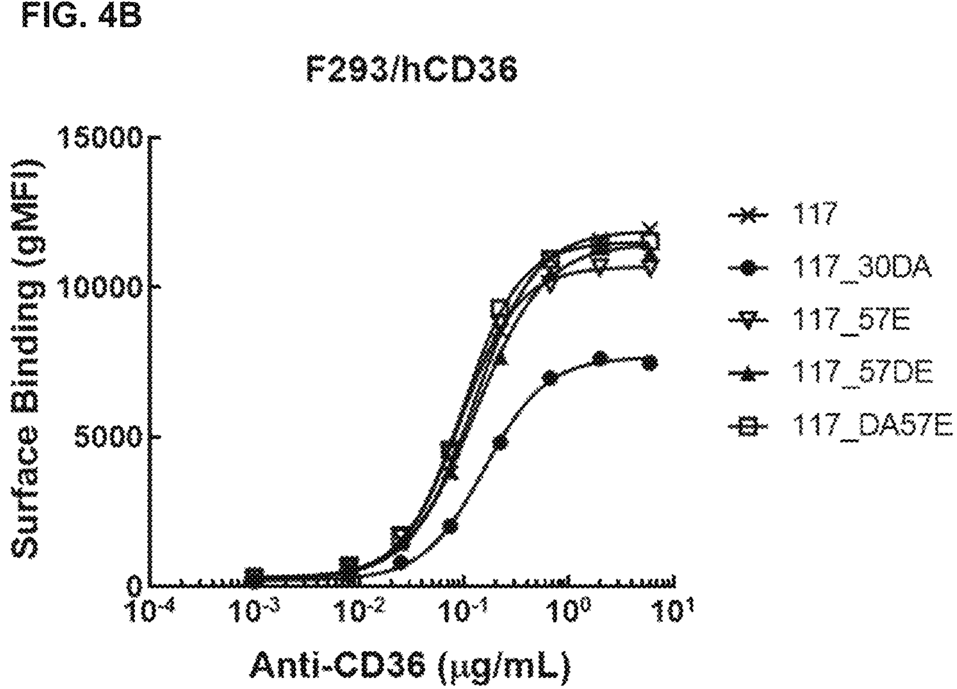
Figures 4E, 4F:
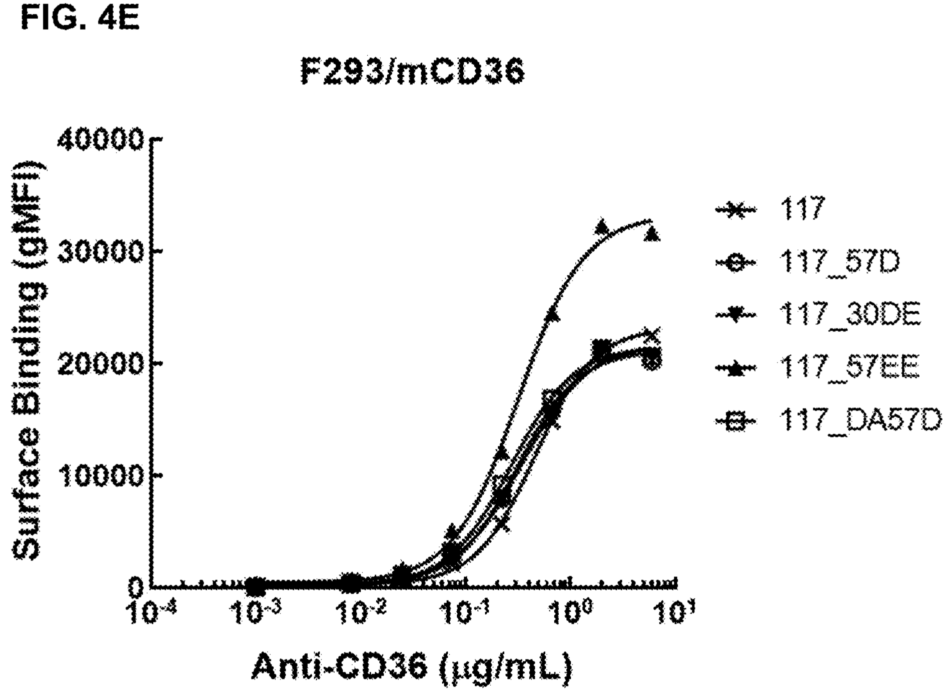

| mAb | Retention time | mAb | Retention time |
|---|---|---|---|
| 117_28D | 8.26 min | 117_57T | 8.17 min |
| 117_31D | 7.93 min | 117_58E | 8.41 min |
| FIG. 3B | | FIG. 3D | |
| STD IgG | 6.81 min | STD IgG | 6.87 min |
| 117 | 8.93 min | Ctl Ab | 7.19 min |
| 117_30DA | 7.97 min | 12P109 | 10.64 min |
| 117_30DT | 8.02 min | 117 | 11.46 min |
| 117_30FA | 13.22 min | 117_DA57E | 7.42 min |
| 117_30FT | 13.56 min | 117_30DE | 7.41 min |
| 117_31AD | 7.58 min | 117_AA57E | 9.53 min |
| 117_31AT | 8.22 min | | |
| FIG. 3E | | | |
| ONA | | 7.21 min | |
| 117_57EE | | 7.41 min | |
| 117_DA57E | | 7.22 min | |
| 117_DA57E (R409K) | | 7.21 min | |

G. BLI Analysis of CD36 Binding Kinetics

BLI assay materials and method: Kinetic rate constants, ka and kd, for binding of the anti-CD36 antibodies to human CD36 were measured by Bio-Layer Interferometry (BLI) (ForteBio Octet RED96). The BLI assay was performed using AHC (Anti-hIgG Fc Capture) biosensors (ForteBio) to capture each anti-CD36 antibody (5 μg/mL) to acquire a 0.5 nm shift and then the biosensors were dipped into varying concentrations (i.e., 0, 1.5625, 3.125, 6.25, 4.94, 12.5, 25, 50 and 100 nM) of recombinant His-tagged human CD36.ECD protein (Sino Biological) in running buffer containing 0.1% BSA, 0.1% Tween-20, 250 mM NaCl in PBS. Rate constants were calculated by curve fitting analyses (1:1 Langmuir model) of binding response with a 2.5-minute association and 5-minute dissociation interaction time.

Results: The determined dissociation constant, KD, and kinetic rate constants, ka, and kd, for binding to human CD36 of the anti-CD36 antibodies, 12P109, A8A, 117, and various 117 variants (in either IgG1 and IgG4 format) as determined in separate BLI analysis experiment are provided in Table 10 below.

TABLE 10

| | hCD36 | | | |
|---|---|---|---|---|
| | KD (M) | Ka (1/Ms) | Kd (1/s) | R2 |
| A8A (IgG1) | 3.42E−09 | 1.35E+06 | 4.62E−03 | 0.972 |
| 117 (IgG1) | 4.79E−09 | 4.45E+05 | 2.13E−03 | 0.9916 |
| 117_31A (IgG1) | 4.05E−09 | 4.49E+05 | 1.82E−03 | 0.9931 |
| 117_31A (IgG4) | 4.32E−09 | 4.75E+05 | 2.05E−03 | 0.9928 |
| 117_30AA (IgG4) | 5.74E−09 | 4.91E+05 | 2.82E−03 | 0.9964 |
| 12P109 (IgG1) | 1.85E−08 | 5.22E+05 | 9.63E−03 | 0.9538 |
| 117 (IgG1) | 6.72E−09 | 3.50E+05 | 2.35E−03 | 0.9739 |
| 117_30DA (IgG4) | 3.91E−09 | 3.39E+05 | 1.33E−03 | 0.9859 |
| 117_54E (IgG1) | 4.16E−09 | 9.78E+05 | 4.07E−03 | 0.8375 |
| 117_57D (IgG1) | 4.69E−09 | 3.73E+05 | 1.75E−03 | 0.9795 |
| 117_57E (IgG1) | 4.93E−09 | 3.70E+05 | 1.82E−03 | 0.9785 |
| 117 (IgG4) | 6.49E−09 | 3.86E+05 | 2.50E−03 | 0.9829 |
| 117_57D (IgG4) | 4.96E−09 | 3.36E+05 | 1.67E−03 | 0.9864 |
| 117_57E (IgG4) | 5.28E−09 | 3.25E+05 | 1.71E−03 | 0.986 |
| 117_DA57D (IgG4) | 2.64E−09 | 3.17E+05 | 8.38E−04 | 0.9938 |
| 117_DA57E (IgG4) | 2.52E−09 | 3.19E+05 | 8.03E−04 | 0.994 |
| 117_57EE (IgG1) | 4.27E−09 | 3.64E+05 | 1.55E−03 | 0.9891 |
| 117_30DE (IgG4) | 3.09E−09 | 3.17E+05 | 9.81E−04 | 0.9919 |

Example 2: Binding of Cell Surface Expressed CD36 by Anti-CD36 Antibodies

This example illustrates the preparation of stable F293 cell lines that overexpress hCD36 or mCD36 on the cell surface, and studies to determine binding affinity of exemplary anti-CD36 antibodies of the present disclosure to cell surface expressed human, rhesus, or mouse CD36.

A. Generation of CD36-Overexpressing Stable F293 Cell Lines

Materials and methods: The gene segment encoding full-length human CD36-Flag (Sino Biological), rhesus CD36-His (Sino Biological), and mouse CD36-His (Sino Biological) were sub-clone into pcDNA3.4 topo vector using XbaI/HindIII. Freestyle 293-F cells (Thermo Scientific) were transfected with the plasmid encoding CD36 by polyethylenimine (PEI) method and selected with Geneticin (Thermo Scientific) to establish CD36 stable cell pool. The expression of human CD36 was verified by surface staining of anti-CD36 (clone 5-271, Biolegend) or by intracellular staining of anti-FLAG. The expression of rhesus CD36 was verified by surface staining of anti-CD36 clone 117) or by intracellular staining of anti-His. The expression of mouse CD36 was verified by surface staining of anti-CD36 antibody D2712 (clone CRF D-2712; BD Biosciences, US) or by intracellular staining of anti-His. To enrich CD36-expressing stable cell lines, hCD36, rhesus CD36, or mCD36-overexpressing F293 cell pool were stained with anti-CD36 (clone 5-271, Biolegend), anti-CD36 clone 117, or anti-CD36 D2712 (clone CRF D-2712, BD Biosciences), respectively. The CD36-high cell populations were sorted by FACSAria IIIu (BD).

Results: Analysis of the FACS data confirmed that the stable F293 cells F293/hCD36,F293/rhesusCD36, and F293/mCD36 overexpress surface CD36 that is capable of binding by an anti-CD36 antibody.

B. Cell Surface CD36 Binding Activity of Anti-CD36 Antibodies

Materials and methods: CD36-high expressing F293 cells generated as described in part A above were incubated with a series dilution of anti-CD36 antibodies, 117, and several variants of 117 (see listed in Table 3) at 4° C. for 30 min. After washing with FACS buffer (2% FBS in PBS), the cells were stained with anti-human IgG-Alexa Fluor 647 and analyzed by Attune NxT Flow Cytometer (Thermo Scientific).

Results: Analysis of the flow cytometry data expressed as geometric mean (MFI) confirmed that the anti-CD36 antibodies specifically bind to cells that surface expressed hCD36 and mCD36.

Data plots showing the surface binding to F293 cells expressing human, rhesus, or mouse CD36 are depicted in FIG. 4A, FIG. 4B, FIG. 4C, FIG. 4D, and FIG. 4E, for the full-length IgG anti-CD36 antibody, 117, and the several 117 variants. $EC_{50}$ values derived from the curves of FIGS. 4A-4E. are shown in Table 11 below.

TABLE 11

| | $EC_{50}$ (μg/mL) | | |
|---|---|---|---|
| mAb | hCD36 | rhesus CD36 | mCD36 |
| 117 | 0.180 | 0.886 | 0.460 |
| 117_57D | 0.111 | 0.397 | 0.309 |
| 117_57E | 0.110 | 0.419 | 0.331 |
| 117_30DE | 0.107 | 0.403 | 0.342 |
| 117_57EE | 0.093 | 0.407 | 0.319 |
| 117_DA57D | 0.089 | 0.416 | 0.271 |
| 117_DA57E | 0.109 | 0.563 | 0.425 |
| 117 | 0.123 | 0.582 | 0.361 |
| 117_30DA | 0.157 | 1.041 | 0.488 |
| 117_57E | 0.091 | 0.362 | 0.279 |
| 117_57DE | 0.129 | 0.529 | 0.447 |
| 117_DA57E | 0.0968 | 0.671 | 0.375 |

Example 3: Oxidized LDL Uptake Blocking Activity of Anti-CD36 Antibodies

This example illustrates studies to determine ability of the exemplary anti-CD36 antibodies of the present disclosure to block oxidized LDL uptake by CD36 expressing cells.

A. Inhibition of Oxidized LDL Binding and Uptake in U937 Cells by Anti-CD36 Antibodies CD36-high expressing U937 cells were pre-incubated with control IgG or anti-CD36 antibodies at 4° C. for 30 min. To measure the binding or uptake of oxLDL, Dil-oxLDL (5-10 μg/mL) (Cat. No. 770232-9; Kalen Biomedical), a purified human LDL that has been oxidized with copper (II) sulfate and labeled with "Dil" (1,1'-dioctadecyl-3,3,3',3'-tetramethylindocarbocyanine perchlorate), was added in serum-free medium and incubated at 4° C. for 2 h or at 37° C. for 5 min, respectively. After washing with PBS, the cells were analyzed by Attune NxT Flow Cytometer (Thermo Scientific).

Figures 5A, 5B:
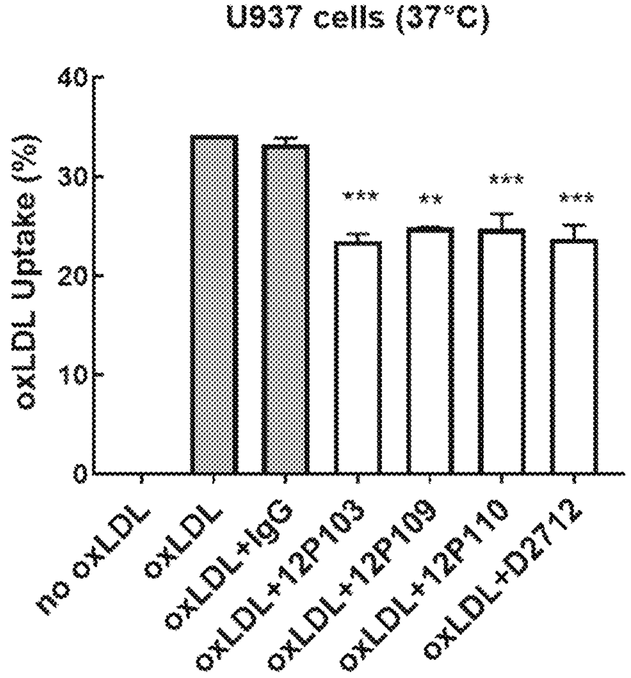
FIG. 5A and FIG. 5B depict plots of extracted flow cytometry data showing the activity of anti-CD36 antibodies of the present disclosure in blocking oxLDL binding (FIG. 5A) and oxLDL uptake (FIG. 5B) by U937 cells as described in Example 3.

The binding of the anti-CD36 antibodies of the present disclosure to U937 cells was observed to result in a characteristic shift demonstrating endogenous expression by U937 of surface CD36. Analysis of the extracted U937 flow cytometry data confirmed a reduction of oxLDL binding FIG. 5A) and oxLDL uptake (FIG. 5B) by the U937 cells relative to the IgG isotype control when incubated with an anti-CD36 antibodies of the present disclosure, 12P103, 12P110, or 12P109.

B. Inhibition of Oxidized LDL Uptake in F293/CD36 Cells by Anti-CD36 Antibodies

F293/hCD36 cells were pre-incubated with control IgG or anti-CD36 antibodies at 4° C. for 30 min. To measure the binding or uptake of oxLDL, Dil-oxLDL (5 μg/mL) (Kalen Biomedical) was added in serum-free medium and incubated at 4° C. for 2 h to measure "oxLDL binding," or at 37° C. for 5 min to measure "oxLDL uptake", respectively. After washing with PBS, the cell preparations were analyzed by Attune NxT Flow Cytometer (Thermo Scientific).

Figure 6A:
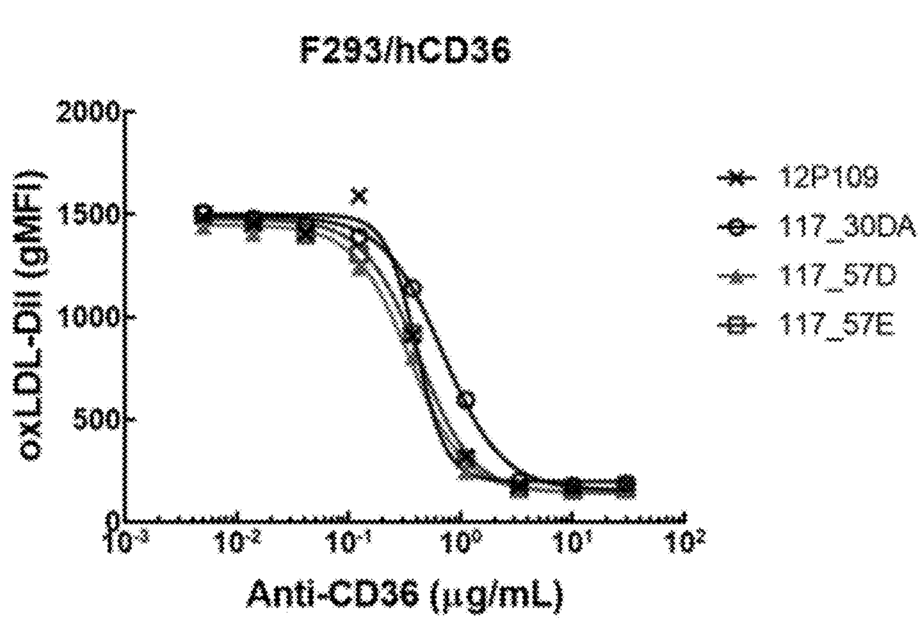
FIG. 6A, FIG. 6B, and FIG. 6C depict plots extracted from flow cytometry data illustrating the oxLDL uptake blocking activity exhibited by the anti-CD36 antibodies (12P109, and 117 variants) in F293/hCD36 or F293/mCD36 cells, as described in Example 3.
Figure 6B:
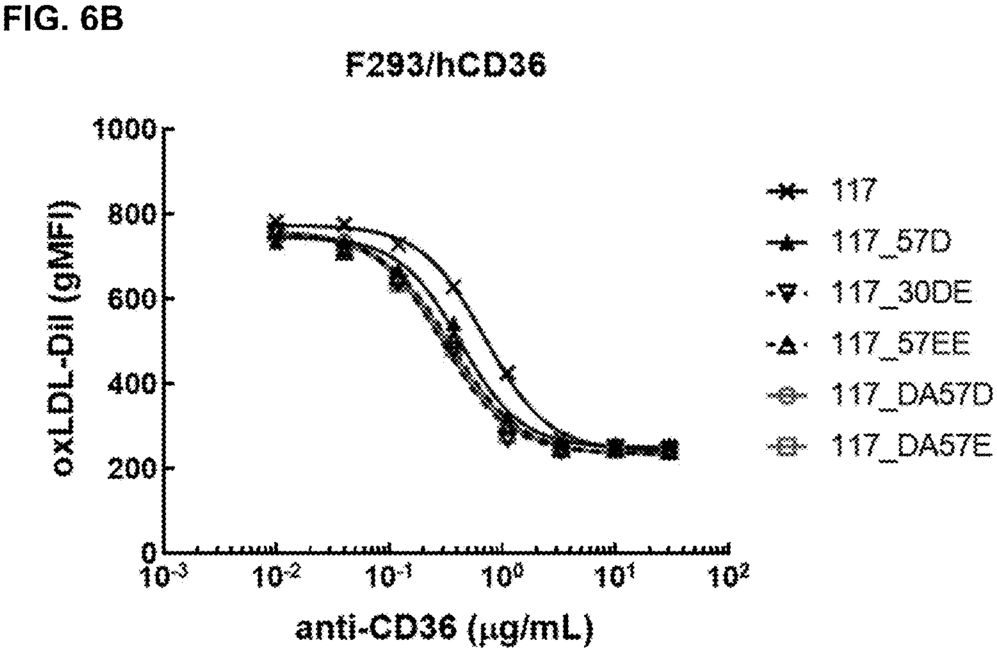
Figure 6C:
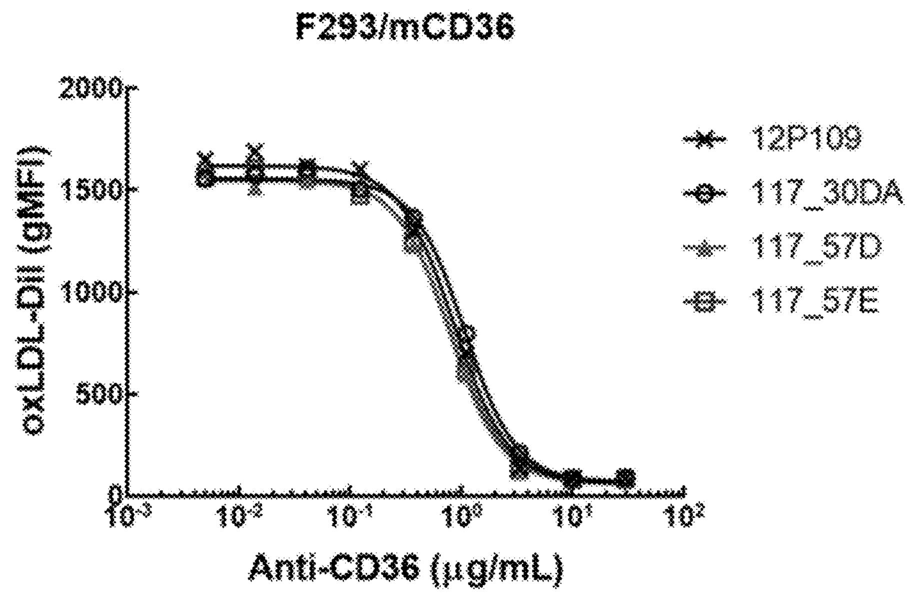

Results: As shown by the plots of flow cytometry data depicted in FIG. 6A, FIG. 6B and FIG. 6C, the presence of an anti-CD36 antibodies 12P109, 117, 117_30DA, 117_57D, 117_57E, 117_30DE, 117_57EE, 117_DA57D, or 117_DA57E, effectively blocked oxidized LDL uptake by the F293 cells that overexpress human CD36 on their surface. Additionally, as shown by the plots in FIG. 6C, the presence of an anti-CD36 antibodies 12P109, 117_30DA, 117_57D, or 117_57E, effectively blocked ox LDL uptake by the F293 cells that overexpress mouse CD36 on their surface. $IC_{50}$ values for inhibition of oxLDL uptake by the F293/hCD36 or F293/mCD36 cells determined for these anti-CD36 antibodies are shown in Table 13 below.

TABLE 13

| mAb | oxLDL uptake IC50 (nM) | |
|---|---|---|
| | F293/hCD36 | F293/mCD36 |
| 12P109 | 0.401 | 0.860 |
| 117_30DA | 0.691 | 1.07 |
| 117_57D | 0.349 | 0.783 |
| 117_57E | 0.419 | 0.796 |
| 117 | 0.702 | n.d. |
| 117_30DE | 0.299 | n.d. |
| 117_57EE | 0.348 | n.d. |
| 117_DA57D | 0.332 | n.d. |
| 117_DA57E | 0.306 | n.d. |

Example 4: Activity of Anti-CD36 Antibodies in Blocking oxLDL Uptake by TILs

This example illustrates studies anti-CD36 antibodies in blocking oxidized LDL uptake in mouse tumor-infiltrating lymphocyte cells (TILs).

Materials and methods: The murine colon carcinoma cell line CT-26 ($2\times10^5$ cells, ATCC number: CRL-2638) or murine liver cancer cell line BNL 1MEA.7R.1 ($5\times10^6$ cells, ATCC number: TIB-75) were subcutaneously injected into the right flank of BALB/c mice. The murine colon carcinoma cell line MC38 ($1\times10^6$ cells, Kerafast #ENH204-FP), murine melanoma cell line B16-F10 ($1\times10^6$ cells, BCRC #60031), or murine lung cancer cell line LL/2 ($2\times10^5$ cells, BCRC #60050) were subcutaneously injected into the right flank of C57BL/6 mice. The CT-26 tumors were harvested after 4 weeks. The B16-F10, BNL 1MEA.7R.1, MC38, and LL/2 tumors were harvested after 2 weeks. Tumor cell suspensions were prepared from solid tumors using mouse Tumor Dissociation Kit (Miltenyi Biotec) according to manufacturers' instructions. CD45+ TILs were isolated from the tumor cell suspensions using CD45 microbeads (Miltenyi Biotec).

Isolated CD45+ TILs were pre-incubated with control IgG or anti-CD36 antibodies (5-10 μg/mL) at 4° C. for 30 min. Dil-oxLDL (5-10 μg/mL) was added in RPMI medium containing 1% fatty acid-free BSA and incubated at 37° C. for 15 min. After washing with PBS, the cells were analyzed by Attune NxT Flow Cytometer (Thermo Scientific). The binding and uptake of oxLDL were analyzed by flow cytometry and expressed as percentage (%) positive cells based on a histogram gate placed on negative control cells.

Data represent mean±SD. *$p<0.05$, **$p<0.005$, one-way ANOVA.

Figure 7A:
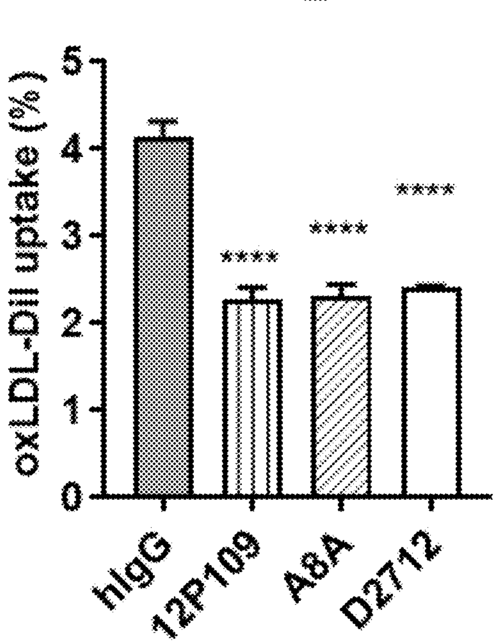
FIG. 7A, FIG. 7B, FIG. 7C, FIG. 7D, and FIG. 7E depict plots of data showing the ability of the anti-CD36 antibodies of the present disclosure (12P109, A8A, and 117 variants) to inhibit oxLDL uptake in TILs from colon cancer (CT26, MC38), liver cancer (BNL 1MEA.7R.1), lung cancer (LL2), and melanoma (B16F10) syngeneic mouse models as described in Example 4.
Figure 7B:
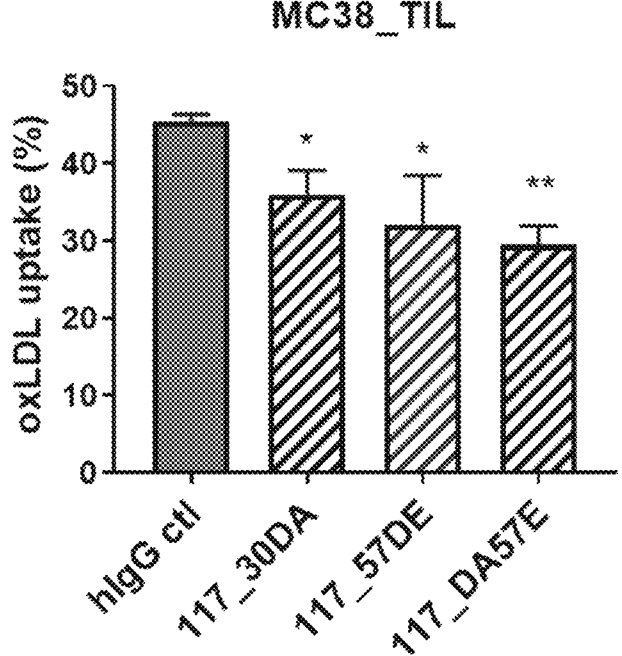
Figure 7C:
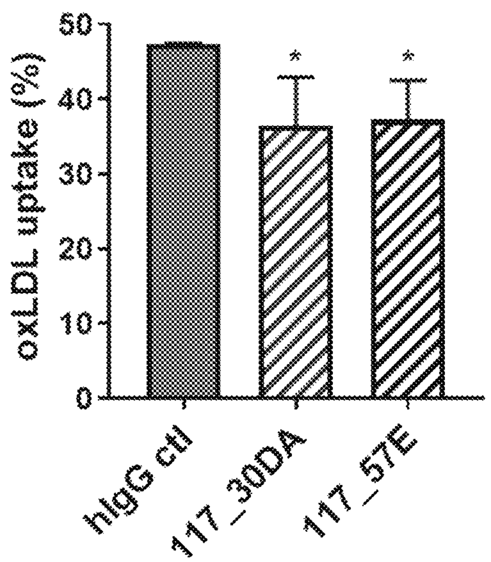
Figure 7D:
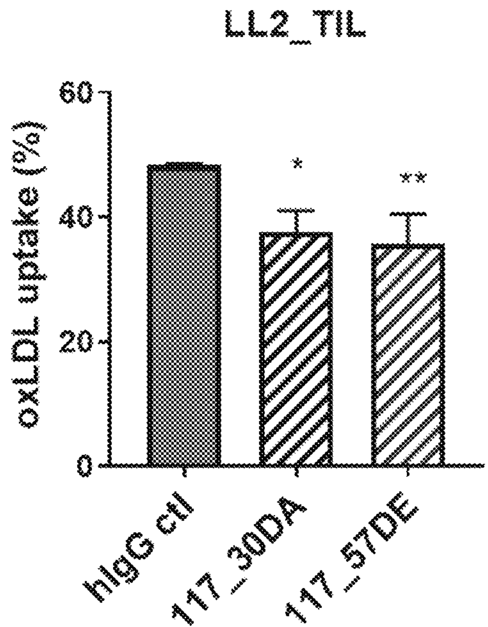
Figure 7E:
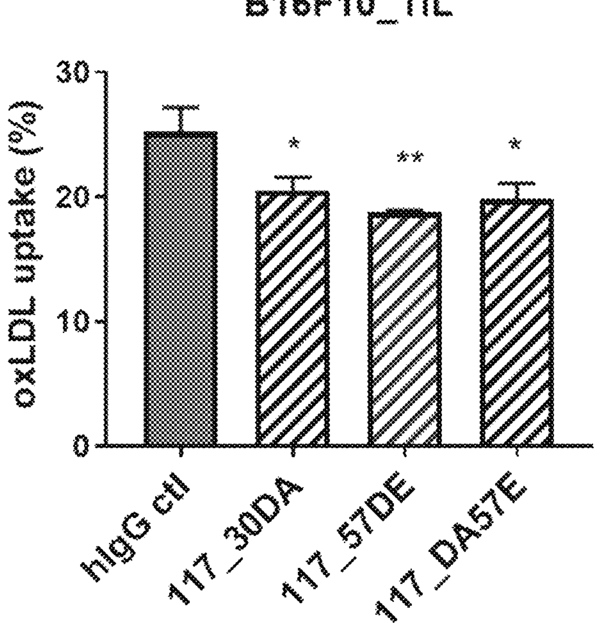

Results: As shown by the plot of results depicted in FIG. 7A, the anti-CD36 antibodies of the present disclosure that bind specifically to hCD36 and mCD36, 12P109 and A8A, provided approximately 35% inhibition of oxLDL uptake in CD45+ TILs isolated from CT26 tumors injected into BALB/c mice. The level of inhibition was equivalent to that observed for the commercial antibody, D2712, that specifically binds mouse CD36.

As shown by the plot of results depicted in FIG. 7B, FIG. 7C, FIG. 7D and FIG. 7E, the anti-CD36 antibodies 117_57E, 117_30DA, 117_57DE, and 117_DA57E, showed inhibitory activity to oxLDL uptake in CD45+ TIL from B16-F10, BNL 1MEA.7R.1, MC38, and LL/2 tumors.

Example 5: M2 Macrophage Polarization and Activation Blocking Activity

This study was carried out to determine the ability of the anti-CD36 antibodies of the present disclosure inhibit M2 macrophage polarization and activation.

Materials and methods: To generate monocyte derived macrophages, human CD14+ monocytes were isolated from PBMC and cultured at $2\times10^6$ cells/ml in RPMI1640 supplemented with 10% FBS and 20 ng/ml CSF1 for 6 days. Then adherent macrophages were collected by EDTA detachment and seeded in a 24-well plate for further polarization. For M0 macrophages, cells were culture in culture medium for 2 days. To polarize M2 macrophages, macrophages were culture in medium containing 50 ng/ml IL-4 and 50 ng/ml IL-13 for another 2 days. 10 μg/mL control IgG or anti-CD36 antibodies were added during M2 macrophage polarization. For oxLDL activation, macrophages were pre-incubated with control IgG or anti-CD36 antibodies for 10 min and then cultured in M2 medium containing 10 μg/mL oxLDL (Kalen Biomedical) for another 2 days. To examine M2 macrophage activation, macrophages were harvested and stained with antibodies against CD206, CD301 and PDL2. The level of surface markers was analyzed by Attune NxT Flow Cytometer (Thermo Scientific).

Figure 8A:
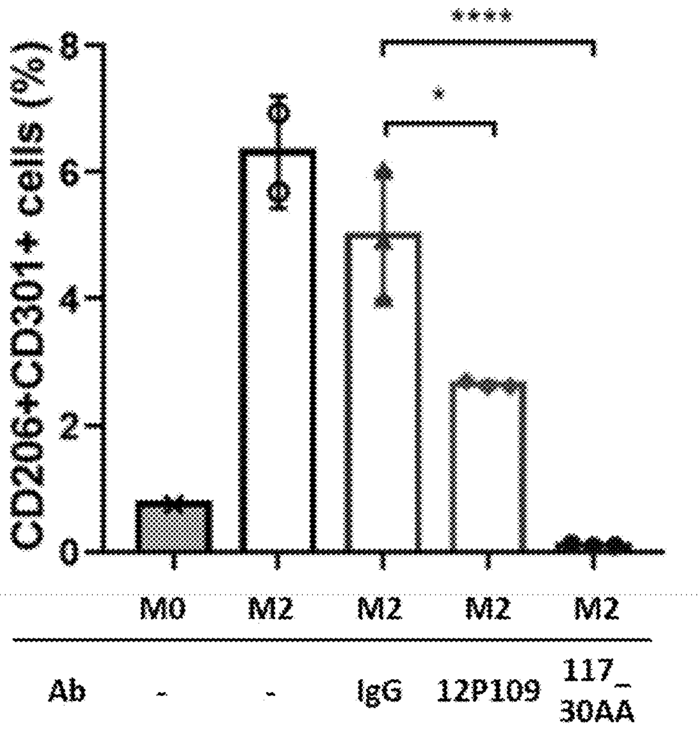
FIG. 8A, FIG. 8B, FIG. 8C, FIG. 8D, FIG. 8E, and FIG. 8F depict plots of data illustrating the ability of the anti-CD36 antibodies of the present disclosure (12P109, and 117 variants) to inhibit M2 macrophage polarization (FIG. 8A and FIG. 8B) and oxLDL-induced M2 macrophage activation (FIG. 8C, FIG. 8D, FIG. 8E and FIG. 8F), as described in Example 5.
Figure 8B:
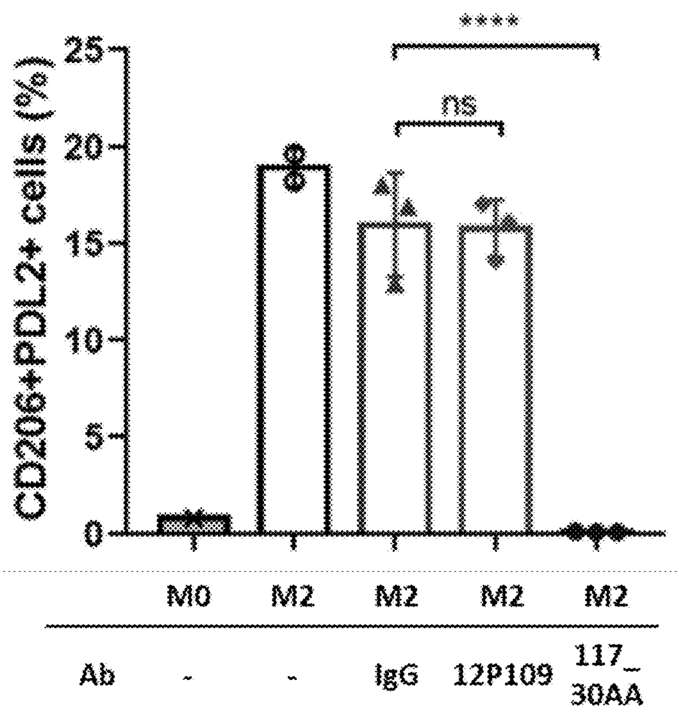
Figure 8C:
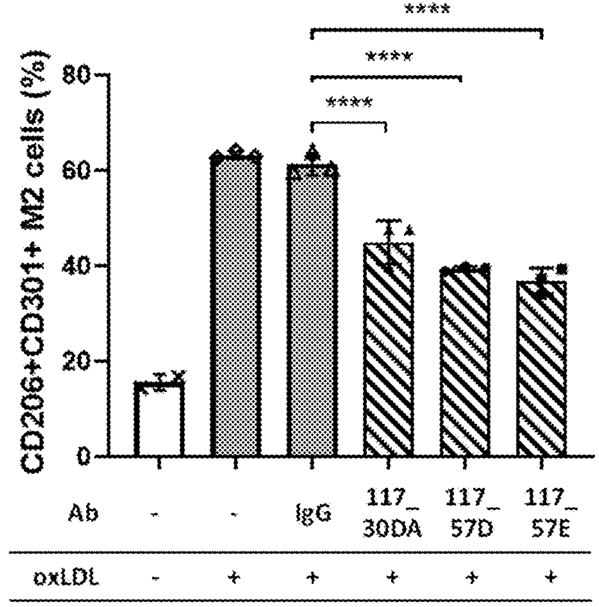
Figure 8D:
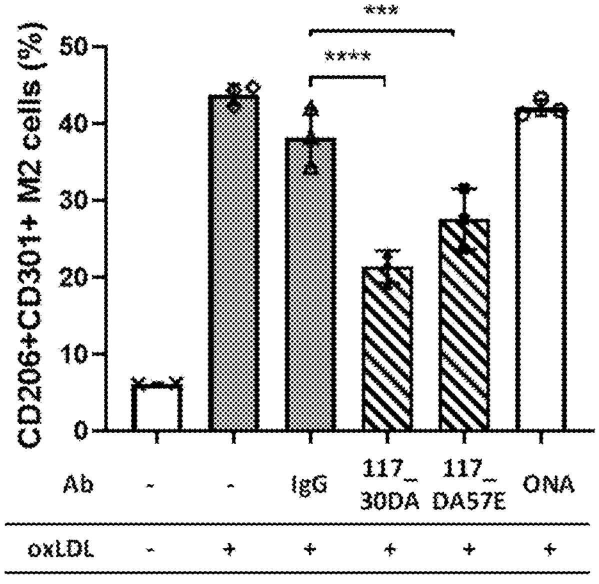
Figure 8E:
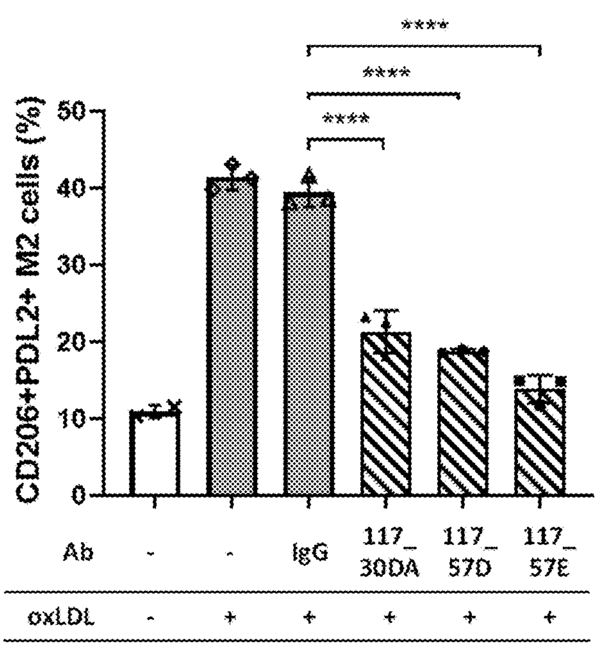
Figure 8F:
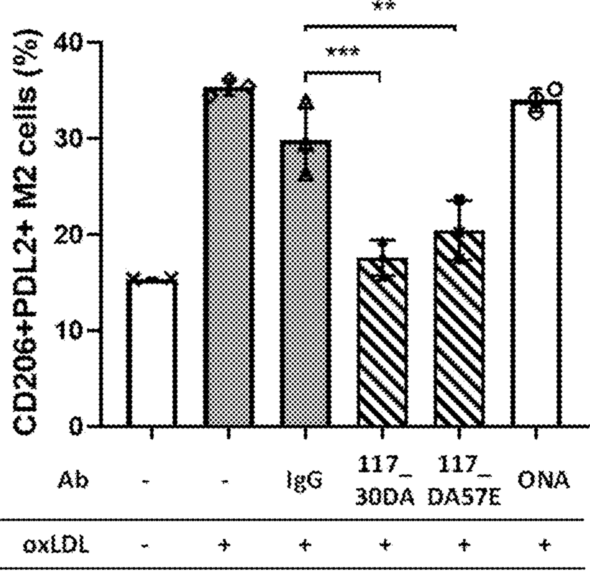

Results: As shown by the plots of data depicted in FIG. 8A and FIG. 8B, the anti-CD36 antibody, 117_30AA exhibited very strong inhibition of M2 macrophage polarization in both CD206+/CD301+ (FIG. 8A) and the CD206+/PDL2+ (FIG. 8B) double-positive cell populations. As shown by the plots of data depicted in FIG. 8C, FIG. 8D, FIG. 8E and FIG. 8F, the anti-CD36 antibodies, 117_30DA, 117_57D, 117_57E, and 117_DA57E exhibited very strong inhibition of oxLDL-induced M2 macrophage activation in both the CD206+/CD301+ (FIG. 8C, FIG. 8D) and the CD206+/PDL2+ (FIG. 8E, FIG. 8F) double-positive cell populations. As shown by the plots of data depicted in FIG. 8D and FIG. 8F, the anti-CD36 antibodies, 117_30DA, and 117_DA57E exhibited very strong inhibition of oxLDL-induced M2 macrophage activation compared to the IgG control and the competitor anti-CD36 antibody "ONA", which is Fab clone "ONA-0-v1" as disclosed in WO2021176424A1 with hIgG4-S228P-FALA Fc region.

Example 6: Activity of Anti-CD36 Antibodies in a Mouse Hepatocellular Carcinoma Model This example illustrates a study of anti-CD36 antibody activity in suppressing tumor growth in two genetically induced mouse models of hepatocellular carcinoma (HCC): (1) HCC induced by the Sleeping Beauty transposon (SB100x) system-mediated transgenes of MYC-luc-ova overexpression and p53 knockout; and (2) HCC induced by the Sleeping Beauty transposon (SB100x) system-mediated transgenes of MYC-luc-ova and β-catenin$^{N90}$.

Materials and methods 6-week old mice are restrained, and hydrodynamic delivery of endotoxin-free plasmid DNA is conducted through the lateral tail vein injection in a volume equivalent to 10% of the body weight within 5-7 seconds. For the MYC$^{OE}$/p53$^{KO}$ HCC model, pT3-Myc-luc-ova plasmid (Addgene #129776), p53 gRNA plasmid (Addgene #59910), and SB100x (transposase-containing plasmid; Addgene #34879) were injected into the mice. For the β-catenin/Myc (β-catenin$^{OE}$/MYC$^{OE}$) HCC model, pT3-bcatenin (Addgene #31785), pT3-Myc-luc-ova plasmid, and SB100x were injected into each mouse. β-catenin-driven liver tumor represents a more aggressive HCC with cold tumor phenotype.

To monitor tumor growth, mice were injected with luciferin (150 mg/Kg), and the bioluminescence activity was analyzed in the IVIS imaging system. Mice with continued tumor growth were randomly grouped and administered the anti-CD36 antibody (10 mg/kg) or PBS (control) through intraperitoneal injection as described below.

After 2 weeks, MYC$^{OE}$/p53$^{KO}$ HCC model mice were intraperitoneally injected with 4 doses of anti-CD36 antibody (10 mg/kg; clone: 117_30DA) or control antibody every 3 days, and the bioluminescence imaging of mice was measured in IVIS system every 6 days (n=5 per group).

After 3 weeks, β-catenin$^{OE}$/MYC$^{OE}$ HCC model mice were intraperitoneally injected with anti-CD36 antibody (10 mg/mL, clone: 117_DA57E) or control antibody (n=6 per group), and the bioluminescence imaging of mice was measured in IVIS system every 5 days.

In the β-catenin$^{OE}$/MYC$^{OE}$ HCC model, tumors exhibit aggressive progress and tumor-bearing mice usually die 38 days after hydrodynamic injection. Accordingly, tumors were harvested and weighed 35-38 days after hydrodynamic tail vein injection.

Results

Figure 9:
FIG. 9 depicts tumor growth curve results measured by bioluminescence in the $MYC^{OE}/p53^{KO}$ HCC model mice following treatment with the anti-CD36 antibody 117_30DA as described in Example 6.
Figure 9:
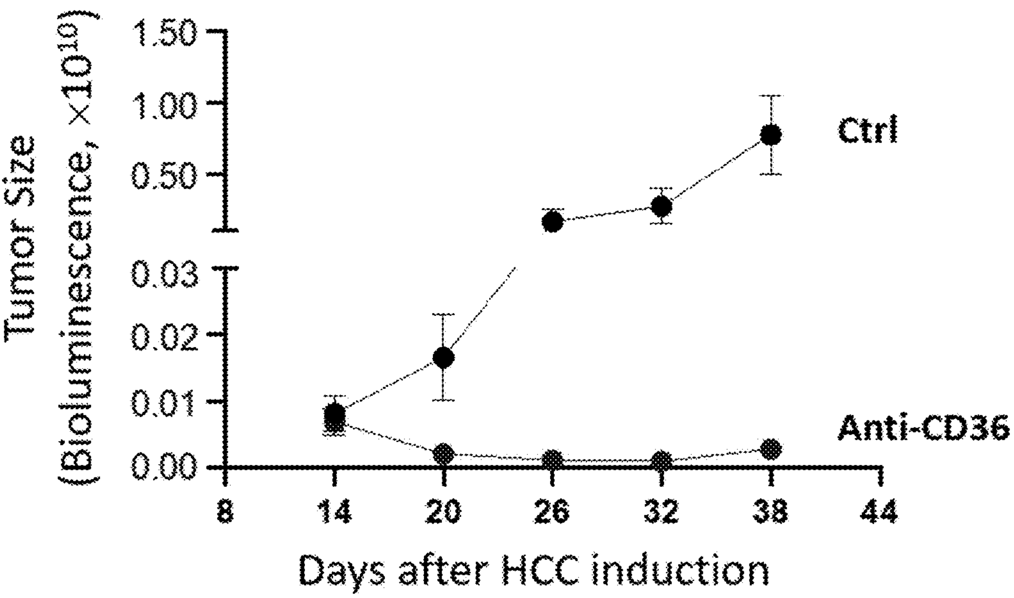

FIG. 9 shows the tumor growth curves measured by bioluminescence in the MYC$^{OE}$/p53$^{KO}$ HCC model mice following treatment with the anti-CD36 antibody 117_30DA. Starting at 14 days after HCC induction and continuing out to 38 days, tumor growth was observed to be significantly suppressed in the treated mice versus controls. P-value=0.0114, t-test, two-tail.

FIG. 10A shows the tumor growth curves measured by bioluminescence in the β-catenin$^{OE}$/MYC$^{OE}$ HCC model mice following treatment with the anti-CD36 antibody 117_DA57E. Starting 21 days after HCC induction and continuing out to 36 days, tumor growth was observed to be significantly suppressed in the treated mice versus controls. P-value=0.0104, t-test, two-tail. FIG. 10B shows that the endpoint liver weights were significantly reduced in the anti-CD36 treated mice. Additionally, as shown in FIG. 10C plasma ALT (alanine transaminase) activity analysis indicated that the anti-CD36 treatment also alleviated liver damage caused by cancer development.

While the foregoing disclosure of the present invention has been described in some detail by way of example and illustration for purposes of clarity and understanding, this disclosure including the examples, descriptions, and embodiments described herein are for illustrative purposes, are intended to be exemplary, and should not be construed as limiting the present disclosure. It will be clear to one skilled in the art that various modifications or changes to the examples, descriptions, and embodiments described herein can be made and are to be included within the spirit and purview of this disclosure and the appended claims. Further, one of skill in the art will recognize a number of equivalent methods and procedure to those described herein. All such equivalents are to be understood to be within the scope of the present disclosure and are covered by the appended claims.

Additional embodiments of the invention are set forth in the following claims.

The disclosures of all publications, patent applications, patents, or other documents mentioned herein are expressly incorporated by reference in their entirety for all purposes to the same extent as if each such individual publication, patent, patent application or other document were individually specifically indicated to be incorporated by reference herein in its entirety for all purposes and were set forth in its entirety herein. In case of conflict, the present specification, including specified terms, will control.

REFERENCES

Al-Khami, A. A. et al. (2017). Exogenous lipid uptake induces metabolic and functional reprogramming of tumor-associated myeloid-derived suppressor cells. Oncoimmunology 6: e1344804, doi: 10.1080/2162402X.2017.1344804.

Almeida, P. E. et al. (2014). Differential TLR2 downstream signaling regulates lipid metabolism and cytokine production triggered by Mycobacterium bovis BCG infection. Biochim. Biophys. Acta. 1841:97-107, doi: 10.1016/j.bbalip.2013.10.008.

Aloia, A. et al. (2019). A fatty acid oxidation-dependent metabolic shift regulates the adaptation of BRAF-mutated melanoma to MAPK inhibitors. Clin. Cancer Res. 25:6852, doi: 10.1158/1078-0432.CCR-19-0253.

Barrett, L. et al. (2007). Circulating CD14-CD36+ peripheral blood mononuclear cells constitutively produce interleukin-10. J. Leukoc. Biol. 82:152-60, doi: 10.1189/jlb.0806521.

Chung, E. Y. et al. (2007). Interleukin-10 expression in macrophages during phagocytosis of apoptotic cells is mediated by homeodomain proteins Pbx1 and Prep-1. Immunity 27:952-964, doi: 10.1016/j.immuni.2007.11.014.

Enciu, A.-M. et al. (2018). Targeting CD36 as biomarker for metastasis prognostic: how far from translation into clinical practice? Biomed. Res. Int. 2018:7801202, doi: 10.1155/2018/7801202.

Feng, W. W. et al. (2019). CD36-mediated metabolic rewiring of breast cancer cells promotes resistance to HER2-targeted therapies. Cell Reports 29: 3405-20, doi: 10.1016/j.celrep.2019.11.008.

Goedegebuure, P. et al. (2011). Myeloid-derived suppressor cells: general characteristics and relevance to clinical management of pancreatic cancer. Curr. Cancer Drug Targets 11: 734-51, doi: 10.2174/156800911796191024.

Hale, J. S. et al. (2014). Cancer stem cell-specific scavenger receptor CD36 drives glioblastoma progression. Stem Cells 32: 1746-58, doi: 10.1002/stem.1716.

Huang, S. C. et al. (2014). Cell-intrinsic lysosomal lipolysis is essential for alternative activation of macrophages. Nature Immunol. 15: 846-55, doi: 10.1038/ni.2956.

Joyce, J. A. & Pollard, J. W. (2009). Microenvironmental regulation of metastasis. Nature Reviews Cancer 9: 239-52, doi: 10.1038/nrc2618.

Kuda, O. et al. (2011). CD36 protein is involved in store-operated calcium flux, phospholipase A2 activation, and production of prostaglandin E2. J. Biol. Chem. 286: 17785-95, doi: 10.1074/jbc.M111.232975.

Lewis, C. E. & Pollard, J. W. (2006). Distinct role of macrophages in different tumor microenvironments. Cancer Res. 66: 605-12, doi: 10.1158/0008-5472.CAN-05-4005.

Liang, Y. et al. (2018). CD36 plays a critical role in proliferation, migration and tamoxifen-inhibited growth of ER-positive breast cancer cells. Oncogenesis 7: 98, doi: 10.1038/s41389-018-0107-x.

Ma, X. et al. (2021). CD36-mediated ferroptosis dampens intratumoral CD8+ T cell effector function and impairs their antitumor ability, Cell Metabolism 33: 1-12, doi: 10.1016/j.cmet.2021.02.015.

Mizuno, R. et al. (2019). Prostaglandin E2/EP signaling in the tumor microenvironment of colorectal cancer. Int. J. Mol. Sci. 20: 6254, doi: 10.3390/ijms20246254.

Nath, A. et al. (2015). Elevated free fatty acid uptake via CD36 promotes epithelial-mesenchymal transition in hepatocellular carcinoma. Sci. Rep. 5: 14752, doi: 10.1038/srep14752.

Oh, J. et al. (2012). Endoplasmic reticulum stress controls M2 macrophage differentiation and foam cell formation. J. Biol. Chem. 287: 11629-41, doi: 10.1074/jbc.M111.338673.

Oh, K. et al. (2013). A mutual activation loop between breast cancer cells and myeloid-derived suppressor cells facilitates spontaneous metastasis through IL-6 trans-signaling in a murine model. Breast Cancer Research 15: R79, doi: 10.1186/ber3473.

Pascual, G. et al. (2017). Targeting metastasis-initiating cells through the fatty acid receptor CD36. Nature 541: 41-45, doi: 10.1038/nature20791.

Pepino, Y. M. et al. (2014). Structure-function of CD36 and importance of fatty acid signal transduction in fat metabolism. Annu. Rev. Nutr. 34: 281-303, doi: 10.1146/annurev-nutr-071812-161220.

Pepper, M. S. et al. (2003). Lymphangiogenesis and tumor metastasis. Cell Tissue Res 314: 167-77, doi: 10.1007/s00441-003-0748-7.

Pollard, J. W. (2008). Macrophages define the invasive microenvironment in breast cancer. J. Leukoc. Biol. 84: 623-30, doi: 10.1189/jlb.1107762.

Psaila, B. & Lyden, D. (2009). The metastatic niche: adapting the foreign soil. Nature Reviews Cancer 9: 285-93, doi: 10.1038/nrc2621.

Rada, P. et al. (2020). Understanding lipotoxicity in NAFLD pathogenesis: is CD36 a key driver? Cell Death and Disease 11: 802, doi: 10.1038/s41419-020-03003-w.

Su, P. et al. (2020). Enhanced lipid accumulation and metabolism are required for the differentiation and activation of tumor-associated macrophages. Cancer Res. 80: 1438-50, doi: 10.1158/0008-5472.CAN-19-2994.

Sugimoto, Y. et al. (1993). Molecular cloning and characterization of the complementary DNA for the $M_r$ 85,000 protein overexpressed in adriamycin-resistant human tumor cells. Cancer Res. 53:2538-43.

Wang, D. & Dubois, R. N. (2006). Prostaglandins and cancer. Gut 55:115-22, doi: 10.1136/gut.2004.047100.

Wang, J. & Li, Y. (2019). CD36 tango in cancer: signaling pathways and functions. Theranostics 9: 4893-908, doi: 10.7150/thno.36037.

Wang, H. et al. (2020). CD36-mediated metabolic adaptation supports regulatory T cell survival and function in tumors. Nat. Immunol. 21: 298-308, doi: 10.1038/s41590-019-0589-5.

Watt, M. J. et al. (2019). Suppressing fatty acid uptake has therapeutic effects in preclinical models of prostate cancer. Sci. Transl. Med. 11: eaau5758, doi: 10.1126/scitranslmed.aau5758.

Whiteside, T. L. & Jackson, E. K. (2013). Adenosine and prostaglandin e2 production by human inducible regulatory T cells in health and disease. Frontiers Immunol. 4: 212, doi: 10.3389/fimmu.2013.00212.

Wu, K. et al. (2020). Redefining tumor-associated macrophage subpopulations and functions in the tumor microenvironment. Front. Immunol. 11: 1731, doi: 10.3389/fimmu.2020.01731.

Xu, S. et al. (2020). Oxidized lipids and CD36-mediated lipid peroxidation in CD8 T cells suppress anti-tumor immune responses. BioRxiv preprint doi: 10.1101/2020.09.03.281691.

Xu, S. et al. (2021). Uptake of oxidized lipids by the scavenger receptor CD36 promotes lipid peroxidation and dysfunction in $CD8^+$ T cells in tumors. Immunity 54(7): 1561-1577.e7, doi: 10.1016/j.immuni.2021.05.003.

Ye, H. et al. (2016). Leukemic stem cells evade chemotherapy by metabolic adaptation to an adipose tissue niche. Cell Stem Cell 19: 23-37, doi: 10.1016/j.stem.2016.06.001.

Zeisberger, S. M. et al. (2006). Clodronate-liposome-mediated depletion of tumour-associated macrophages: a new and highly effective antiangiogenic therapy approach. British J. Cancer 95: 272-81, doi: 10.1038/sj.bjc.6603240.

Zhao, L. et al. (2018). CD36 and lipid metabolism in the evolution of atherosclerosis. British Medical Bulletin 126: 101-112, 10.1093/bmb/ldy006.

What is claimed is:

1. An anti-CD36 antibody comprising (i) a first heavy chain complementary determining region (CDR-H1), a second heavy chain complementary determining region (CDR-H2), and a third heavy chain complementary determining region (CDR-H3), and (ii) a first light chain complementary determining region (CDR-L1), a second light chain complementary determining region (CDR-L2), and a third light chain complementary determining region (CDR-L3), wherein:

(a) CDR-H1 comprises the amino acid sequence of SEQ ID NO: 24, 3, 21, or 27;

(b) CDR-H2 comprises the amino acid sequence of SEQ ID NO: 43, 4, 28, 31, 34, 37, or 40;

(c) CDR-H3 comprises the amino acid sequence of SEQ ID NO: 5;

(d) CDR-L1 comprises an amino acid sequence selected from SEQ ID NO: 7;

(e) CDR-L2 comprises an amino acid sequence selected from SEQ ID NO: 15, 8, or 12; and (f) CDR-L3 comprises an amino acid sequence selected from SEQ ID NO: 18, 9, or 13.

2. The antibody of claim 1, wherein:

(a) CDR-H1 comprises the amino acid sequence of SEQ ID NO: 24, CDR-H2 comprises the amino acid sequence of SEQ ID NO: 43, CDR-H3 comprises the amino acid sequence of SEQ ID NO: 5, CDR-L1 comprises the amino acid sequence of SEQ ID NO: 7, CDR-L2 comprises the amino acid sequence of SEQ ID NO: 15, and CDR-L3 comprises the amino acid sequence of SEQ ID NO: 18;

(b) CDR-H1 comprises the amino acid sequence of SEQ ID NO: 3, CDR-H2 comprises the amino acid sequence of SEQ ID NO: 4, CDR-H3 comprises the amino acid sequence of SEQ ID NO: 5, CDR-L1 comprises the amino acid sequence of SEQ ID NO: 7, CDR-L2 comprises the amino acid sequence of SEQ ID NO: 8, and CDR-L3 comprises the amino acid sequence of SEQ ID NO: 9;

(c) CDR-H1 comprises the amino acid sequence of SEQ ID NO: 3, CDR-H2 comprises the amino acid sequence of SEQ ID NO: 4, CDR-H3 comprises the amino acid sequence of SEQ ID NO: 5, CDR-L1 comprises the amino acid sequence of SEQ ID NO: 7, CDR-L2 comprises the amino acid sequence of SEQ ID NO: 12, and CDR-L3 comprises the amino acid sequence of SEQ ID NO: 13;

(d) CDR-H1 comprises the amino acid sequence of SEQ ID NO: 3, CDR-H2 comprises the amino acid sequence of SEQ ID NO: 4. CDR-H3 comprises the amino acid sequence of SEQ ID NO: 5, CDR-L1 comprises the amino acid sequence of SEQ ID NO: 7, CDR-L2 comprises the amino acid sequence of SEQ ID NO: 15, and CDR-L3 comprises the amino acid sequence of SEQ ID NO: 13;

(e) CDR-H1 comprises the amino acid sequence of SEQ ID NO: 3, CDR-H2 comprises the amino acid sequence of SEQ ID NO: 4, CDR-H3 comprises the amino acid sequence of SEQ ID NO: 5, CDR-L1 comprises the amino acid sequence of SEQ ID NO: 7. CDR-L2 comprises the amino acid sequence of SEQ ID NO: 15, and CDR-L3 comprises the amino acid sequence of SEQ ID NO: 18;

(f) CDR-H1 comprises the amino acid sequence of SEQ ID NO: 21, CDR-H2 comprises the amino acid sequence of SEQ ID NO: 4, CDR-H3 comprises the amino acid sequence of SEQ ID NO: 5, CDR-L1 comprises the amino acid sequence of SEQ ID NO: 7, CDR-L2 comprises the amino acid sequence of SEQ ID NO: 15, and CDR-L3 comprises the amino acid sequence of SEQ ID NO: 18;

(g) CDR-H1 comprises the amino acid sequence of SEQ ID NO: 24, CDR-H2 comprises the amino acid sequence of SEQ ID NO: 4, CDR-H3 comprises the amino acid sequence of SEQ ID NO: 5, CDR-L1 comprises the amino acid sequence of SEQ ID NO: 7, CDR-L2 comprises the amino acid sequence of SEQ ID NO: 15, and CDR-L3 comprises the amino acid sequence of SEQ ID NO: 18;

(h) CDR-H1 comprises the amino acid sequence of SEQ ID NO: 27, CDR-H2 comprises the amino acid sequence of SEQ ID NO: 28, CDR-H3 comprises the amino acid sequence of SEQ ID NO: 5, CDR-L1 comprises the amino acid sequence of SEQ ID NO: 7, CDR-L2 comprises the amino acid sequence of SEQ ID NO: 15, and CDR-L3 comprises the amino acid sequence of SEQ ID NO: 18;

(i) CDR-H1 comprises the amino acid sequence of SEQ ID NO: 3, CDR-H2 comprises the amino acid sequence of SEQ ID NO: 31, CDR-H3 comprises the amino acid sequence of SEQ ID NO: 5, CDR-L1 comprises the amino acid sequence of SEQ ID NO: 7, CDR-L2 comprises the amino acid sequence of SEQ ID NO: 15, and CDR-L3 comprises the amino acid sequence of SEQ ID NO: 18;

(j) CDR-H1 comprises the amino acid sequence of SEQ ID NO: 3, CDR-H2 comprises the amino acid sequence of SEQ ID NO: 34, CDR-H3 comprises the amino acid sequence of SEQ ID NO: 5, CDR-L1 comprises the amino acid sequence of SEQ ID NO: 7. CDR-L2 comprises the amino acid sequence of SEQ ID NO: 15, and CDR-L3 comprises the amino acid sequence of SEQ ID NO: 18;

(k) CDR-H1 comprises the amino acid sequence of SEQ ID NO: 3, CDR-H2 comprises the amino acid sequence of SEQ ID NO: 37, CDR-H3 comprises the amino acid sequence of SEQ ID NO: 5, CDR-L1 comprises the amino acid sequence of SEQ ID NO: 7, CDR-L2 comprises the amino acid sequence of SEQ ID NO: 15, and CDR-L3 comprises the amino acid sequence of SEQ ID NO: 18; or (l) CDR-H1 comprises the amino acid sequence of SEQ ID NO: 3, CDR-H2 comprises the amino acid sequence of SEQ ID NO: 40, CDR-H3 comprises the amino acid sequence of SEQ ID NO: 5, CDR-L1 comprises the amino acid sequence of SEQ ID NO: 7, CDR-L2 comprises the amino acid sequence of SEQ ID NO: 15, and CDR-L3 comprises the amino acid sequence of SEQ ID NO: 18.

3. The antibody of claim 1, wherein the antibody comprises a heavy chain variable domain ($V_H$) amino acid sequence having at least 90% identity to a sequence selected from SEQ ID NO: 42, 2, 20, 23, 26, 30, 33, 36, or 39; and a light chain variable domain ($V_L$) amino acid sequence having at least 90% identity to a sequence selected from SEQ ID NO: 17, 6, 11, or 14.

4. The antibody of claim 1, wherein:

(a) the antibody comprises a $V_H$ amino acid sequence having at least 90% identity to SEQ ID NO: 42 and a $V_L$ amino acid sequence having at least 90% identity to SEQ ID NO: 17;

(b) the antibody comprises a $V_H$ amino acid sequence having at least 90% identity to SEQ ID NO: 2 and a $V_L$ amino acid sequence having at least 90% identity to SEQ ID NO: 6;

(c) the antibody comprises a $V_H$ amino acid sequence having at least 90% identity to SEQ ID NO: 2 and a $V_L$ amino acid sequence having at least 90% identity to SEQ ID NO: 11;

(d) the antibody comprises a $V_H$ amino acid sequence having at least 90% identity to SEQ ID NO: 2 and a $V_L$ amino acid sequence having at least 90% identity to SEQ ID NO: 14;

(e) the antibody comprises a $V_H$ amino acid sequence having at least 90% identity to SEQ ID NO: 2 and a $V_L$ amino acid sequence having at least 90% identity to SEQ ID NO: 17;

(f) the antibody comprises a $V_H$ amino acid sequence having at least 90% identity to SEQ ID NO: 20 and a $V_L$ amino acid sequence having at least 90% identity to SEQ ID NO: 17;

(g) the antibody comprises a $V_H$ amino acid sequence having at least 90% identity to SEQ ID NO: 23 and a $V_L$ amino acid sequence having at least 90% identity to SEQ ID NO: 17;

(h) the antibody comprises a VH amino acid sequence having at least 90% identity to SEQ ID NO: 26 and a VL amino acid sequence having at least 90% identity to SEQ ID NO: 17;

(i) the antibody comprises a $V_H$ amino acid sequence having at least 90% identity to SEQ ID NO: 30 and a $V_L$ amino acid sequence having at least 90% identity to SEQ ID NO: 17;

(j) the antibody comprises a $V_H$ amino acid sequence having at least 90% identity to SEQ ID NO: 33 and a $V_L$ amino acid sequence having at least 90% identity to SEQ ID NO: 17;

(k) the antibody comprises a VH amino acid sequence having at least 90% identity to SEQ ID NO: 36 and a VL amino acid sequence having at least 90% identity to SEQ ID NO: 17; or (l) the antibody comprises a VH amino acid sequence having at least 90% identity to SEQ ID NO: 39 and a VL amino acid sequence having at least 90% identity to SEQ ID NO: 17.

5. The antibody of claim 1, wherein the antibody comprises a heavy chain (HC) amino acid sequence having at least 90% identity to a sequence selected from SEQ ID NO: 57, 44, 48, 50, 51, 52, 53, 54, 55, or 56, and/or a light chain (LC) amino acid sequence having at least 90% identity to a sequence selected from SEQ ID NO: 49, 45, 46, or 47.

6. The antibody of claim 1, wherein the antibody comprises:

(a) an HC amino acid sequence having at least 90% identity to SEQ ID NO: 57 and an LC amino acid sequence having at least 90% identity to SEQ ID NO: 49;

(b) an HC amino acid sequence having at least 90% identity to SEQ ID NO: 44 and an LC amino acid sequence having at least 90% identity to SEQ ID NO: 45;

(c) an HC amino acid sequence having at least 90% identity to SEQ ID NO: 44 and an LC amino acid sequence having at least 90% identity to SEQ ID NO: 46;

(d) an HC amino acid sequence having at least 90% identity to SEQ ID NO: 44 and an LC amino acid sequence having at least 90% identity to SEQ ID NO: 47;

(c) an HC amino acid sequence having at least 90% identity to SEQ ID NO: 44, and an LC amino acid sequence having at least 90% identity to SEQ ID NO: 49;

(f) an HC amino acid sequence having at least 90% identity to SEQ ID NO: 48, and an LC amino acid sequence having at least 90% identity to SEQ ID NO: 49;

(g) an HC amino acid sequence having at least 90% identity to SEQ ID NO: 50 and an LC amino acid sequence having at least 90% identity to SEQ ID NO: 49;

(h) an HC amino acid sequence having at least 90% identity to SEQ ID NO: 51 and an LC amino acid sequence having at least 90% identity to SEQ ID NO: 49;

(i) an HC amino acid sequence having at least 90% identity to SEQ ID NO: 52 and an LC amino acid sequence having at least 90% identity to SEQ ID NO: 49;

(j) an HC amino acid sequence having at least 90% identity to SEQ ID NO: 53 and an LC amino acid sequence having at least 90% identity to SEQ ID NO: 49;

(k) an HC amino acid sequence having at least 90% identity to SEQ ID NO: 54 and an LC amino acid sequence having at least 90% identity to SEQ ID NO: 49;

(l) an HC amino acid sequence having at least 90% identity to SEQ ID NO: 55 and an LC amino acid sequence having at least 90% identity to SEQ ID NO: 49; or (m) an HC amino acid sequence having at least 90% identity to SEQ ID NO: 56 and an LC amino acid sequence having at least 90% identity to SEQ ID NO: 49.

7. The antibody of claim 1, wherein the antibody:

(a) is an antibody fragment, optionally selected from the group consisting of F(ab')$_2$, Fab', Fab, Fv, single domain antibody (VHH), and scFv;

(b) comprises a fusion to a protein: optionally, wherein the protein is an immunostimulatory cytokine selected from IL-2, IL-7, IL-10, IL-12, IL-15, IL-21, or IFN-α;

(c) is a human, humanized, or chimeric antibody;

(d) is a full length antibody of class IgG, optionally, wherein the class IgG antibody has an isotype selected from IgG1, IgG2, IgG3, and IgG4;

(e) comprises an Fc region variant, optionally an Fc region variant that alters effector function and/or a variant that alters antibody half-life;

(f) comprises an immunoconjugate, optionally, wherein the immunoconjugate comprises a therapeutic agent for treatment of a CD36-mediated disease or condition; and/or (g) is a multi-specific antibody: optionally a bispecific antibody.

8. An anti-CD36 antibody comprising:

(i) a first heavy chain complementary determining region (CDR-H1), a second heavy chain complementary determining region (CDR-H2), and a third heavy chain complementary determining region (CDR-H3), wherein the CDR-H1, CDR-H2, and CDR-H3 sequences are from a VH region having an amino acid sequence selected from SEQ ID NO: 42, 2, 20, 23, 26, 30, 33, 36, and 39;

(ii) a first light chain complementary determining region (CDR-L1), a second light chain complementary determining region (CDR-L2), and a third light chain complementary determining region (CDR-L3), wherein the CDR-L1, CDR-L2, and CDR-L3 sequences are from a VL region having an amino acid sequence selected from SEQ ID NO: 17, 6, 11, and 14, and wherein the CDR-L1, CDR-L2, CDR-L3, CDR-HI, CDR-H2 and CDR-H3 are according to Kabat numbering.

9. The antibody of claim 8, wherein:

(a) the VH amino acid sequence is SEQ ID NO: 42 and the VL amino acid sequence is SEQ ID NO: 17;

(b) the VH amino acid sequence is SEQ ID NO: 2 and the VL amino acid sequence is SEQ ID NO: 6;

(c) the VH amino acid sequence is SEQ ID NO: 2 and the VL amino acid sequence is SEQ ID NO: 11:

(d) the VH amino acid sequence is SEQ ID NO: 2 and the VL amino acid sequence is SEQ ID NO: 14;

(e) the VH amino acid sequence is SEQ ID NO: 2 and the VL amino acid sequence is SEQ ID NO: 17;

(f) the VH amino acid sequence is SEQ ID NO: 20 and the VL amino acid sequence is SEQ ID NO: 17;

(g) the VH amino acid sequence is SEQ ID NO: 23 and the VL amino acid sequence is SEQ ID NO: 17;

(h) the VH amino acid sequence is SEQ ID NO: 26 and the VL amino acid sequence is SEQ ID NO: 17;

(i) the VH amino acid sequence is SEQ ID NO: 30 and the VL amino acid sequence is SEQ ID NO: 17;

(j) the VH amino acid sequence is SEQ ID NO: 33 and the VL amino acid sequence is SEQ ID NO: 17;

(k) the VH amino acid sequence is SEQ ID NO: 36 and the VL amino acid sequence is SEQ ID NO: 17; or (l) the VH amino acid sequence is SEQ ID NO: 39 and the VL amino acid sequence is SEQ ID NO: 17.

10. A pharmaceutical composition comprising an antibody of claim 1 and a pharmaceutically acceptable carrier.

11. The composition of claim 10, wherein the composition further comprises a chemotherapeutic agent.

12. The composition of claim 10, wherein the composition further comprises an antibody comprising a specificity for an immune checkpoint molecule.

13. The composition of claim 12, wherein the immune checkpoint molecule is selected from PD1, PD-L1, LAG3, CTLA-4, A2AR, TIM-3, BTLA, CD276, CD328, VTCNI, IDO, KIR, NOX2,VISTA, OX40, CD27, CD28, CD40, CD122, CD137, GITR, and ICOS.

14. The composition of claim 10, wherein the composition further comprises an immunostimulatory cytokine.

15. The composition of claim 14, wherein the immunostimulatory cytokine is selected from IL-2, IL-7, IL-10, IL-12, IL-15, IL-21, and IFN-α.

16. A pharmaceutical composition comprising an antibody of claim 8 and a pharmaceutically acceptable carrier.

17. The composition of claim 16, wherein the composition further comprises a chemotherapeutic agent.

18. The composition of claim 16, wherein the composition further comprises an antibody comprising a specificity for an immune checkpoint molecule.

19. The composition of claim 18, wherein the immune checkpoint molecule is selected from PD1, PD-L1, LAG3, CTLA-4, A2AR, TIM-3, BTLA, CD276, CD328, VTCNI, IDO, KIR, NOX2,VISTA, OX40, CD27, CD28, CD40, CD122, CD137, GITR, and ICOS.

20. The composition of claim 16, wherein the composition further comprises an immunostimulatory cytokine.

21. The composition of claim 20, wherein the immunostimulatory cytokine is selected from IL-2,IL-7, IL-10, IL-12, IL-15, IL-21, and IFN-α.

* * * * *

SEQUENCE LISTING

```
Sequence total quantity: 67
SEQ ID NO: 1            moltype = DNA  length = 750
FEATURE                 Location/Qualifiers
source                  1..750
                        mol_type = other DNA
                        organism = Synthetic construct
SEQUENCE: 1
atggccgata ttcaaatgac ccagagcccg agcagcctga gcgcgagcgt gggagatcgc  60
gtgaccatta cctgccgtgc gagccaggat gttagcaact gggtcgcatg gtatcagcag  120
aaaccaggca aagcgccgaa acttctgata tctacctcca ctagcctgta tagcggcgtg  180
ccgtcgcgtt tttcgggcag tggcagcggc acggacttta ccctgacgat atcttcctta  240
caaccggagg attttgcgac ctactactgt caacagtact acaccttgcc gttcaccttc  300
ggtcaaggca ccaaagtgga aatcaaacgc ggtggttcct ctagatcttc cacctctggt  360
ggcggtggct cgggcggtgg tggggaagtg cagctggtgg aatcgggagg cggtctggtg  420
caacctggcg gcagccttcg tctgagctgt gcggcgagcg ggttcaccat tagcagcttt  480
gggattcatt gggtgcgtca agctcccggc aaggggctgg agtgggtcgc gtggattgct  540
ccctacggtg gttacacata ctatgccgac agcgtgaaag gtcgctttac gattagtgcg  600
gacaccagca aaaataccgc gtacctgcag atgaatagcc tgcgtgcgga agacacagcg  660
```

```
gtgtattatt gcgcgcgttc gtttttcggg tacttcgatt attgggggca gggcaccctt  720
gttaccgtga gctcggcgtc agcggccgca                                   750

SEQ ID NO: 2           moltype = AA  length = 117
FEATURE                Location/Qualifiers
source                 1..117
                       mol_type = protein
                       organism = Synthetic construct
SEQUENCE: 2
EVQLVESGGG LVQPGGSLRL SCAASGFTIS SFGIHWVRQA PGKGLEWVAW IAPYGGYTYY  60
ADSVKGRFTI SADTSKNTAY LQMNSLRAED TAVYYCARSF FGYFDYWGQG TLVTVSS     117

SEQ ID NO: 3           moltype = AA  length = 13
FEATURE                Location/Qualifiers
source                 1..13
                       mol_type = protein
                       organism = Synthetic construct
SEQUENCE: 3
AASGFTISSF GIH                                                     13

SEQ ID NO: 4           moltype = AA  length = 10
FEATURE                Location/Qualifiers
source                 1..10
                       mol_type = protein
                       organism = Synthetic construct
SEQUENCE: 4
WIAPYGGYTY                                                         10

SEQ ID NO: 5           moltype = AA  length = 10
FEATURE                Location/Qualifiers
source                 1..10
                       mol_type = protein
                       organism = Synthetic construct
SEQUENCE: 5
ARSFFGYFDY                                                         10

SEQ ID NO: 6           moltype = AA  length = 108
FEATURE                Location/Qualifiers
source                 1..108
                       mol_type = protein
                       organism = Synthetic construct
SEQUENCE: 6
DIQMTQSPSS LSASVGDRVT ITCRASQDVS NWVAWYQQKP GKAPKLLIST STSLYSGVPS  60
RFSGSGSGTD FTLTISSLQP EDFATYYCQQ YYTLPFTFGQ GTKVEIKR              108

SEQ ID NO: 7           moltype = AA  length = 11
FEATURE                Location/Qualifiers
source                 1..11
                       mol_type = protein
                       organism = Synthetic construct
SEQUENCE: 7
RASQDVSNWV A                                                       11

SEQ ID NO: 8           moltype = AA  length = 8
FEATURE                Location/Qualifiers
source                 1..8
                       mol_type = protein
                       organism = Synthetic construct
SEQUENCE: 8
STSTSLYS                                                           8

SEQ ID NO: 9           moltype = AA  length = 8
FEATURE                Location/Qualifiers
source                 1..8
                       mol_type = protein
                       organism = synthetic construct
SEQUENCE: 9
YYTLPFTF                                                           8

SEQ ID NO: 10          moltype = DNA  length = 750
FEATURE                Location/Qualifiers
source                 1..750
                       mol_type = other DNA
                       organism = synthetic construct
SEQUENCE: 10
atggccgata ttcaaatgac ccagagcccg agcagcctga gcgcgagcgt gggagatcgc  60
gtgaccatta cctgccgtgc gagccaggat gttagtaatt gggtcgcatg gtatcagcag  120
aaaccaggca aagcgccgaa acttctgata tcctatgcca acagcctgta tagcggcgtg  180
ccgtcgcgtt tttcgggcag tggcagcggc acggacttta ccctgacgat atcttcctta  240
```

```
caaccggagg attttgcgac ctactactgt caacagcact ctaaccttcc gctgaccttc  300
ggtcaaggca ccaaagtgga aatcaaacgt ggtggttcct ctagatcttc ctcctctggt  360
ggcggtggct cgggcggtgg tggggaagtg cagctggtgg aatcgggagg cggtctggtg  420
caacctggcg gcagccttcg tctgagctgt gcggcgagcg ggttcaccat tagcagcttt  480
gggattcatt gggtgcgtca agctcccggc aaggggctgg agtgggtcgc gtggattgct  540
ccctacggtg gttacacata ctatgccgac agcgtgaaag gtcgctttac gattagtgcg  600
gacaccagca aaaataccgc gtacctgcag atgaatagcc tgcgtgcgga agacacagcg  660
gtgtattatt gcgcgcgttc gtttttcggg tacttcgatt attgggggca gggcaccctt  720
gttaccgtga gctcggcgtc agcggccgca                                    750

SEQ ID NO: 11          moltype = AA  length = 108
FEATURE                Location/Qualifiers
source                 1..108
                       mol_type = protein
                       organism = Synthetic construct
SEQUENCE: 11
DIQMTQSPSS LSASVGDRVT ITCRASQDVS NWVAWYQQKP GKAPKLLISY ANSLYSGVPS  60
RFSGSGSGTD FTLTISSLQP EDFATYYCQQ HSNLPLTFGQ GTKVEIKR               108

SEQ ID NO: 12          moltype = AA  length = 8
FEATURE                Location/Qualifiers
source                 1..8
                       mol_type = protein
                       organism = Synthetic construct
SEQUENCE: 12
SYANSLYS                                                            8

SEQ ID NO: 13          moltype = AA  length = 8
FEATURE                Location/Qualifiers
source                 1..8
                       mol_type = protein
                       organism = synthetic construct
SEQUENCE: 13
HSNLPLTF                                                            8

SEQ ID NO: 14          moltype = AA  length = 108
FEATURE                Location/Qualifiers
source                 1..108
                       mol_type = protein
                       organism = synthetic construct
SEQUENCE: 14
DIQMTQSPSS LSASVGDRVT ITCRASQDVS NWVAWYQQKP GKAPKLLISY ATSLYSGVPS  60
RFSGSGSGTD FTLTISSLQP EDFATYYCQQ HSNLPLTFGQ GTKVEIKR               108

SEQ ID NO: 15          moltype = AA  length = 8
FEATURE                Location/Qualifiers
source                 1..8
                       mol_type = protein
                       organism = synthetic construct
SEQUENCE: 15
SYATSLYS                                                            8

SEQ ID NO: 16          moltype = DNA  length = 750
FEATURE                Location/Qualifiers
source                 1..750
                       mol_type = other DNA
                       organism = synthetic construct
SEQUENCE: 16
atggccgata ttcaaatgac ccagagcccg agcagcctga gcgcgagcgt gggagatcgc  60
gtgaccatta cctgccgtgc gagccaggat gttagtaatt gggtcgcatg gtatcagcag  120
aaaccaggca aagcgccgaa acttctgata tcctatgcta ctagcctgta tagcggcgtg  180
ccgtcgcgtt tttcgggcag tggcagcggc acggacttta ccctgacgat atcttcctta  240
caaccggagg attttgcgac ctactactgt caacagcact ctaacgcgcc gctgaccttc  300
ggtcaaggca ccaaagtgga aatcaaacgc ggtggttcct ctagatcttc ctcctctggt  360
ggcggtggct cgggcggtgg tggggaagtg cagctggtgg aatcgggagg cggtctggtg  420
caacctggcg gcagccttcg tctgagctgt gcggcgagcg ggttcaccat tagcagcttt  480
gggattcatt gggtgcgtca agctcccggc aaggggctgg agtgggtcgc gtggattgct  540
ccctacggtg gttacacata ctatgccgac agcgtgaaag gtcgctttac gattagtgcg  600
gacaccagca aaaataccgc gtacctgcag atgaatagcc tgcgtgcgga agacacagcg  660
gtgtattatt gcgcgcgttc gtttttcggg tacttcgatt attgggggca gggcaccctt  720
gttaccgtga gctcggcgtc agcggccgca                                    750

SEQ ID NO: 17          moltype = AA  length = 108
FEATURE                Location/Qualifiers
source                 1..108
                       mol_type = protein
                       organism = synthetic construct
SEQUENCE: 17
DIQMTQSPSS LSASVGDRVT ITCRASQDVS NWVAWYQQKP GKAPKLLISY ATSLYSGVPS  60
```

```
RFSGSGSGTD FTLTISSLQP EDFATYYCQQ HSNAPLTFGQ GTKVEIKR          108

SEQ ID NO: 18           moltype = AA  length = 8
FEATURE                 Location/Qualifiers
source                  1..8
                        mol_type = protein
                        organism = synthetic construct
SEQUENCE: 18
HSNAPLTF                                                      8

SEQ ID NO: 19           moltype = DNA  length = 750
FEATURE                 Location/Qualifiers
source                  1..750
                        mol_type = other DNA
                        organism = synthetic construct
SEQUENCE: 19
atggccgata ttcaaatgac ccagagcccg agcagcctga gcgcgagcgt gggagatcgc  60
gtgaccatta cctgccgtgc gagccaggat gttagtaatt gggtcgcatg gtatcagcag  120
aaaccaggca aagcgccgaa acttctgata tcctatgcta ctagcctgta tagcggcgtg  180
ccgtcgcgtt tttcgggcag tggcagcggc acggacttta ccctgacgat atcttcctta  240
caaccggagg attttgcgac ctactactgt caacagcact ctaacgcgcc gctgaccttc  300
ggtcaaggca ccaaagtgga aatcaaacgc ggtggttcct ctagatcttc ctcctctggt  360
ggcggtggct cgggcggtgg tggggaagtg cagctggtgg aatcgggagg cggtctggtg  420
caacctggcg gcagccttcg tctgagctgt gcggcgagcg ggttcaccat tgccgccttt  480
gggattcatt gggtgcgtca agctcccggc aaggggctgg agtgggtcgc gtggattgct  540
ccctacggtg gttacacata ctatgccgac agcgtgaaag gtcgctttac gattagtgcg  600
gacaccagca aaaataccgc gtacctgcag atgaatagcc tgcgtgcgga agacacagcg  660
gtgtattatt gcgcgcgttc gtttttcggg tacttcgatt attgggggca gggcaccctt  720
gttaccgtga gctcggcgtc agcggccgca                                   750

SEQ ID NO: 20           moltype = AA  length = 117
FEATURE                 Location/Qualifiers
source                  1..117
                        mol_type = protein
                        organism = synthetic construct
SEQUENCE: 20
EVQLVESGGG LVQPGGSLRL SCAASGFTIA AFGIHWVRQA PGKGLEWVAW IAPYGGYTYY  60
ADSVKGRFTI SADTSKNTAY LQMNSLRAED TAVYYCARSF FGYFDYWGQG TLVTVSS     117

SEQ ID NO: 21           moltype = AA  length = 13
FEATURE                 Location/Qualifiers
source                  1..13
                        mol_type = protein
                        organism = synthetic construct
SEQUENCE: 21
AASGFTIAAF GIH                                                13

SEQ ID NO: 22           moltype = DNA  length = 750
FEATURE                 Location/Qualifiers
source                  1..750
                        mol_type = other DNA
                        organism = synthetic construct
SEQUENCE: 22
atggccgata ttcaaatgac ccagagcccg agcagcctga gcgcgagcgt gggagatcgc  60
gtgaccatta cctgccgtgc gagccaggat gttagtaatt gggtcgcatg gtatcagcag  120
aaaccaggca aagcgccgaa acttctgata tcctatgcta ctagcctgta tagcggcgtg  180
ccgtcgcgtt tttcgggcag tggcagcggc acggacttta ccctgacgat atcttcctta  240
caaccggagg attttgcgac ctactactgt caacagcact ctaacgcgcc gctgaccttc  300
ggtcaaggca ccaaagtgga aatcaaacgc ggtggttcct ctagatcttc ctcctctggt  360
ggcggtggct cgggcggtgg tggggaagtg cagctggtgg aatcgggagg cggtctggtg  420
caacctggcg gcagccttcg tctgagctgt gcggcgagcg ggttcaccat tgacgccttt  480
gggattcatt gggtgcgtca agctcccggc aaggggctgg agtgggtcgc gtggattgct  540
ccctacggtg gttacacata ctatgccgac agcgtgaaag gtcgctttac gattagtgcg  600
gacaccagca aaaataccgc gtacctgcag atgaatagcc tgcgtgcgga agacacagcg  660
gtgtattatt gcgcgcgttc gtttttcggg tacttcgatt attgggggca gggcaccctt  720
gttaccgtga gctcggcgtc agcggccgca                                   750

SEQ ID NO: 23           moltype = AA  length = 117
FEATURE                 Location/Qualifiers
source                  1..117
                        mol_type = protein
                        organism = synthetic construct
SEQUENCE: 23
EVQLVESGGG LVQPGGSLRL SCAASGFTID AFGIHWVRQA PGKGLEWVAW IAPYGGYTYY  60
ADSVKGRFTI SADTSKNTAY LQMNSLRAED TAVYYCARSF FGYFDYWGQG TLVTVSS     117

SEQ ID NO: 24           moltype = AA  length = 13
FEATURE                 Location/Qualifiers
source                  1..13
```

```
                        mol_type = protein
                        organism = synthetic construct
SEQUENCE: 24
AASGFTIDAF GIH                                                      13

SEQ ID NO: 25           moltype = DNA  length = 351
FEATURE                 Location/Qualifiers
source                  1..351
                        mol_type = other DNA
                        organism = synthetic construct
SEQUENCE: 25
gaagtgcagc tggtggaatc gggaggcggt ctggtgcaac ctggcggcag ccttcgtctg  60
agctgtgcgg cgagcgggtt caccattgac agctttggga ttcattgggt gcgtcaagct  120
cccggcaagg ggctggagtg ggtcgcgtgg attgctccct acggtggtga aacatactat  180
gccgacagcg tgaaaggtcg ctttacgatt agtgcggaca ccagcaaaaa taccgcgtac  240
ctgcagatga atagcctgcg tgcggaagac acagcggtgt attattgcgc gcgttcgttt  300
ttcgggtact tcgattattg gggcagggc acccttgtta ccgtgagctc g           351

SEQ ID NO: 26           moltype = AA  length = 117
FEATURE                 Location/Qualifiers
source                  1..117
                        mol_type = protein
                        organism = synthetic construct
SEQUENCE: 26
EVQLVESGGG LVQPGGSLRL SCAASGFTID SFGIHWVRQA PGKGLEWVAW IAPYGGETYY  60
ADSVKGRFTI SADTSKNTAY LQMNSLRAED TAVYYCARSF FGYFDYWGQG TLVTVSS     117

SEQ ID NO: 27           moltype = AA  length = 13
FEATURE                 Location/Qualifiers
source                  1..13
                        mol_type = protein
                        organism = synthetic construct
SEQUENCE: 27
AASGFTIDSF GIH                                                      13

SEQ ID NO: 28           moltype = AA  length = 10
FEATURE                 Location/Qualifiers
source                  1..10
                        mol_type = protein
                        organism = synthetic construct
SEQUENCE: 28
WIAPYGGETY                                                          10

SEQ ID NO: 29           moltype = DNA  length = 750
FEATURE                 Location/Qualifiers
source                  1..750
                        mol_type = other DNA
                        organism = synthetic construct
SEQUENCE: 29
atggccgata ttcaaatgac ccagagcccg agcagcctga gcgcgagcgt gggagatcgc  60
gtgaccatta cctgccgtgc gagccaggat gttagtaatt gggtcgcatg gtatcagcag  120
aaaccaggca aagcgccgaa acttctgata tcctatgcta ctagcctgta tagcggcgtg  180
ccgtcgcgtt tttcgggcag tggcagcggc acggacttta ccctgacgat atcttcctta  240
caaccggagg attttgcgac ctactactgt caacagcact ctaacgcgcc gctgaccttc  300
ggtcaaggca ccaaagtgga aatcaaacgc ggtggttcct ctagatcttc ctcctctggt  360
ggcggtggct cgggcggtgg tggggaagtg cagctggtgg aatcgggagg cggtctggtg  420
caacctggcg gcagccttcg tctgagctgt gcggcgagcg ggttcaccat tagcagcttt  480
gggattcatt gggtgcgtca agctcccggc aaggggctgg agtgggtcgc gtggattgct  540
ccctacggtg gtgacacata ctatgccgac agcgtgaaag gtcgctttac gattagtgcg  600
gacaccagca aaaataccgc gtacctgcag atgaatagcc tgcgtgcgga agacacagcg  660
gtgtattatt gcgcgcgttc gtttttcggg tacttcgatt attgggggca gggcaccctt  720
gttaccgtga gctcggcgtc agcggccgca                                    750

SEQ ID NO: 30           moltype = AA  length = 117
FEATURE                 Location/Qualifiers
source                  1..117
                        mol_type = protein
                        organism = synthetic construct
SEQUENCE: 30
EVQLVESGGG LVQPGGSLRL SCAASGFTIS SFGIHWVRQA PGKGLEWVAW IAPYGGDTYY  60
ADSVKGRFTI SADTSKNTAY LQMNSLRAED TAVYYCARSF FGYFDYWGQG TLVTVSS     117

SEQ ID NO: 31           moltype = AA  length = 10
FEATURE                 Location/Qualifiers
source                  1..10
                        mol_type = protein
                        organism = synthetic construct
SEQUENCE: 31
WIAPYGGDTY                                                          10
```

```
SEQ ID NO: 32           moltype = DNA  length = 750
FEATURE                 Location/Qualifiers
source                  1..750
                        mol_type = other DNA
                        organism = synthetic construct
SEQUENCE: 32
atggccgata ttcaaatgac ccagagcccg agcagcctga gcgcgagcgt gggagatcgc  60
gtgaccatta cctgccgtgc gagccaggat gttagtaatt gggtcgcatg gtatcagcag  120
aaaccaggca aagcgccgaa acttctgata tcctatgcta ctagcctgta tagcggcgtg  180
ccgtcgcgtt tttcgggcag tggcagcggc acggacttta ccctgacgat atcttcctta  240
caaccggagg attttgcgac ctactactgt caacagcact ctaacgcgcc gctgaccttc  300
ggtcaaggca ccaaagtgga aatcaaacgc ggtggttcct ctagatcttc ctcctctggt  360
ggcggtggct cgggcggtgg tggggaagtg cagctggtgg aatcgggagg cggtctggtg  420
caacctggcg gcagccttcg tctgagctgt gcggcgagcg ggttcaccat tagcagcttt  480
gggattcatt gggtgcgtca agctcccggc aaggggctgg agtgggtcgc gtggattgct  540
ccctacggtg gtgaaacata ctatgccgac agcgtgaaag gtcgctttac gattagtgcg  600
gacaccagca aaaataccgc gtacctgcag atgaatagcc tgcgtgcgga agacacagcg  660
gtgtattatt gcgcgcgttc gtttttcggg tacttcgatt attgggggca gggcaccctt  720
gttaccgtga gctcggcgtc agcggccgca                                  750

SEQ ID NO: 33           moltype = AA  length = 117
FEATURE                 Location/Qualifiers
source                  1..117
                        mol_type = protein
                        organism = synthetic construct
SEQUENCE: 33
EVQLVESGGG LVQPGGSLRL SCAASGFTIS SFGIHWVRQA PGKGLEWVAW IAPYGGETYY  60
ADSVKGRFTI SADTSKNTAY LQMNSLRAED TAVYYCARSF FGYFDYWGQG TLVTVSS     117

SEQ ID NO: 34           moltype = AA  length = 10
FEATURE                 Location/Qualifiers
source                  1..10
                        mol_type = protein
                        organism = synthetic construct
SEQUENCE: 34
WIAPYGGETY                                                        10

SEQ ID NO: 35           moltype = DNA  length = 351
FEATURE                 Location/Qualifiers
source                  1..351
                        mol_type = other DNA
                        organism = synthetic construct
SEQUENCE: 35
gaagtgcagc tggtggaatc gggaggcggt ctggtgcaac ctggcggcag ccttcgtctg  60
agctgtgcgg cgagcgggtt caccattagc agctttggga ttcattgggt gcgtcaagct  120
cccggcaagg ggctggagtg ggtcgcgtgg attgctccct acggtggtga cgaatactat  180
gccgacagcg tgaaaggtcg ctttacgatt agtgcggaca ccagcaaaaa taccgcgtac  240
ctgcagatga atagcctgcg tgcggaagac acagcggtgt attattgcgc gcgttcgttt  300
ttcgggtact tcgattattg ggggcagggc acccttgtta ccgtgagctc g          351

SEQ ID NO: 36           moltype = AA  length = 117
FEATURE                 Location/Qualifiers
source                  1..117
                        mol_type = protein
                        organism = synthetic construct
SEQUENCE: 36
EVQLVESGGG LVQPGGSLRL SCAASGFTIS SFGIHWVRQA PGKGLEWVAW IAPYGGDEYY  60
ADSVKGRFTI SADTSKNTAY LQMNSLRAED TAVYYCARSF FGYFDYWGQG TLVTVSS     117

SEQ ID NO: 37           moltype = AA  length = 10
FEATURE                 Location/Qualifiers
source                  1..10
                        mol_type = protein
                        organism = synthetic construct
SEQUENCE: 37
WIAPYGGDEY                                                        10

SEQ ID NO: 38           moltype = DNA  length = 351
FEATURE                 Location/Qualifiers
source                  1..351
                        mol_type = other DNA
                        organism = synthetic construct
SEQUENCE: 38
gaagtgcagc tggtggaatc gggaggcggt ctggtgcaac ctggcggcag ccttcgtctg  60
agctgtgcgg cgagcgggtt caccattagc agctttggga ttcattgggt gcgtcaagct  120
cccggcaagg ggctggagtg ggtcgcgtgg attgctccct acggtggtga agaatactat  180
gccgacagcg tgaaaggtcg ctttacgatt agtgcggaca ccagcaaaaa taccgcgtac  240
ctgcagatga atagcctgcg tgcggaagac acagcggtgt attattgcgc gcgttcgttt  300
```

```
ttcgggtact tcgattattg ggggcagggc acccttgtta ccgtgagctc g          351

SEQ ID NO: 39          moltype = AA  length = 117
FEATURE                Location/Qualifiers
source                 1..117
                       mol_type = protein
                       organism = synthetic construct
SEQUENCE: 39
EVQLVESGGG LVQPGGSLRL SCAASGFTIS SFGIHWVRQA PGKGLEWVAW IAPYGGEEYY  60
ADSVKGRFTI SADTSKNTAY LQMNSLRAED TAVYYCARSF FGYFDYWGQG TLVTVSS     117

SEQ ID NO: 40          moltype = AA  length = 10
FEATURE                Location/Qualifiers
source                 1..10
                       mol_type = protein
                       organism = synthetic construct
SEQUENCE: 40
WIAPYGGEEY                                                        10

SEQ ID NO: 41          moltype = DNA  length = 750
FEATURE                Location/Qualifiers
source                 1..750
                       mol_type = other DNA
                       organism = synthetic construct
SEQUENCE: 41
atggccgata ttcaaatgac ccagagcccg agcagcctga gcgcgagcgt gggagatcgc  60
gtgaccatta cctgccgtgc gagccaggat gttagtaatt gggtcgcatg gtatcagcag  120
aaaccaggca aagcgccgaa acttctgata tcctatgcta ctagcctgta tagcggcgtg  180
ccgtcgcgtt tttcgggcag tggcagcggc acggacttta ccctgacgat atcttcctta  240
caaccggagg attttgcgac ctactactgt caacagcact ctaacgcgcc gctgaccttc  300
ggtcaaggca ccaaagtgga aatcaaacgc ggtggttcct ctagatcttc ctcctctggt  360
ggcggtggct cgggcggtgg tggggaagtg cagctggtgg aatcgggagg cggtctggtg  420
caacctggcg gcagccttcg tctgagctgt gcggcgagcg ggttcaccat tagcagcttt  480
gggattcatt gggtgcgtca agctcccggc aaggggctgg agtgggtcgc gtggattgct  540
ccctacggtg gtgaaacata ctatgccgac agcgtgaaag gtcgctttac gattagtgcg  600
gacaccagca aaaataccgc gtacctgcag atgaatagcc tgcgtgcgga agacacagcg  660
gtgtattatt gcgcgcgttc gtttttcggg tacttcgatt attgggggca gggcaccctt  720
gttaccgtga gctcggcgtc agcggccgca                                   750

SEQ ID NO: 42          moltype = AA  length = 117
FEATURE                Location/Qualifiers
source                 1..117
                       mol_type = protein
                       organism = synthetic construct
SEQUENCE: 42
EVQLVESGGG LVQPGGSLRL SCAASGFTID AFGIHWVRQA PGKGLEWVAW IAPYGGETYY  60
ADSVKGRFTI SADTSKNTAY LQMNSLRAED TAVYYCARSF FGYFDYWGQG TLVTVSS     117

SEQ ID NO: 43          moltype = AA  length = 10
FEATURE                Location/Qualifiers
source                 1..10
                       mol_type = protein
                       organism = synthetic construct
SEQUENCE: 43
WIAPYGGETY                                                        10

SEQ ID NO: 44          moltype = AA  length = 446
FEATURE                Location/Qualifiers
source                 1..446
                       mol_type = protein
                       organism = synthetic construct
SEQUENCE: 44
EVQLVESGGG LVQPGGSLRL SCAASGFTIS SFGIHWVRQA PGKGLEWVAW IAPYGGYTYY  60
ADSVKGRFTI SADTSKNTAY LQMNSLRAED TAVYYCARSF FGYFDYWGQG TLVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APELLGGPSV  240
FLFPPKPKDT LMISRTPEVT CVVVDVSHED PEVKFNWYVD GVEVHNAKTK PREEQYASTY  300
RVVSVLTVLH QDWLNGKEYK CKVSNKALPA PIEKTISKAK GQPREPQVYT LPPSREEMTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPG                                      446

SEQ ID NO: 45          moltype = AA  length = 214
FEATURE                Location/Qualifiers
source                 1..214
                       mol_type = protein
                       organism = synthetic construct
SEQUENCE: 45
DIQMTQSPSS LSASVGDRVT ITCRASQDVS NWVAWYQQKP GKAPKLLIST STSLYSGVPS  60
RFSGSGSGTD FTLTISSLQP EDFATYYCQQ YYTLPFTFGQ GTKVEIKRTV AAPSVFIFPP  120
```

```
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 46          moltype = AA  length = 214
FEATURE                Location/Qualifiers
source                 1..214
                       mol_type = protein
                       organism = synthetic construct
SEQUENCE: 46
DIQMTQSPSS LSASVGDRVT ITCRASQDVS NWVAWYQQKP GKAPKLLISY ANSLYSGVPS  60
RFSGSGSGTD FTLTISSLQP EDFATYYCQQ HSNLPLTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 47          moltype = AA  length = 214
FEATURE                Location/Qualifiers
source                 1..214
                       mol_type = protein
                       organism = synthetic construct
SEQUENCE: 47
DIQMTQSPSS LSASVGDRVT ITCRASQDVS NWVAWYQQKP GKAPKLLISY ATSLYSGVPS  60
RFSGSGSGTD FTLTISSLQP EDFATYYCQQ HSNLPLTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 48          moltype = AA  length = 443
FEATURE                Location/Qualifiers
source                 1..443
                       mol_type = protein
                       organism = synthetic construct
SEQUENCE: 48
EVQLVESGGG LVQPGGSLRL SCAASGFTIS SFGIHWVRQA PGKGLEWVAW IAPYGGYTYY  60
ADSVKGRFTI SADTSKNTAY LQMNSLRAED TAVYYCARSF FGYFDYWGQG TLVTVSSAST  120
KGPSVFPLAP CSRSTSESTA ALGCLVKDYF PEPVTVSWNS GALTSGVHTF PAVLQSSGLY  180
SLSSVVTVPS SSLGTKTYTC NVDHKPSNTK VDKRVESKYG PPCPPCPAPE AAGGPSVFLF  240
PPKPKDTLMI SRTPEVTCVV VDVSQEDPEV QFNWYVDGVE VHNAKTKPRE EQFNSTYRVV  300
SVLTVLHQDW LNGKEYKCKV SNKGLPSSIE KTISKAKGQP REPQVYTLPP SQEEMTKNQV  360
SLTCLVKGFY PSDIAVEWES NGQPENNYKT TPPVLDSDGS FFLYSRLTVD KSRWQEGNVF  420
SCSVMHEALH NHYTQKSLSL SLG                                          443

SEQ ID NO: 49          moltype = AA  length = 214
FEATURE                Location/Qualifiers
source                 1..214
                       mol_type = protein
                       organism = synthetic construct
SEQUENCE: 49
DIQMTQSPSS LSASVGDRVT ITCRASQDVS NWVAWYQQKP GKAPKLLISY ATSLYSGVPS  60
RFSGSGSGTD FTLTISSLQP EDFATYYCQQ HSNAPLTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 50          moltype = AA  length = 443
FEATURE                Location/Qualifiers
source                 1..443
                       mol_type = protein
                       organism = synthetic construct
SEQUENCE: 50
EVQLVESGGG LVQPGGSLRL SCAASGFTIA AFGIHWVRQA PGKGLEWVAW IAPYGGYTYY  60
ADSVKGRFTI SADTSKNTAY LQMNSLRAED TAVYYCARSF FGYFDYWGQG TLVTVSSAST  120
KGPSVFPLAP CSRSTSESTA ALGCLVKDYF PEPVTVSWNS GALTSGVHTF PAVLQSSGLY  180
SLSSVVTVPS SSLGTKTYTC NVDHKPSNTK VDKRVESKYG PPCPPCPAPE AAGGPSVFLF  240
PPKPKDTLMI SRTPEVTCVV VDVSQEDPEV QFNWYVDGVE VHNAKTKPRE EQFNSTYRVV  300
SVLTVLHQDW LNGKEYKCKV SNKGLPSSIE KTISKAKGQP REPQVYTLPP SQEEMTKNQV  360
SLTCLVKGFY PSDIAVEWES NGQPENNYKT TPPVLDSDGS FFLYSRLTVD KSRWQEGNVF  420
SCSVMHEALH NHYTQKSLSL SLG                                          443

SEQ ID NO: 51          moltype = AA  length = 443
FEATURE                Location/Qualifiers
source                 1..443
                       mol_type = protein
                       organism = synthetic construct
SEQUENCE: 51
EVQLVESGGG LVQPGGSLRL SCAASGFTID AFGIHWVRQA PGKGLEWVAW IAPYGGYTYY  60
ADSVKGRFTI SADTSKNTAY LQMNSLRAED TAVYYCARSF FGYFDYWGQG TLVTVSSAST  120
KGPSVFPLAP CSRSTSESTA ALGCLVKDYF PEPVTVSWNS GALTSGVHTF PAVLQSSGLY  180
SLSSVVTVPS SSLGTKTYTC NVDHKPSNTK VDKRVESKYG PPCPPCPAPE AAGGPSVFLF  240
PPKPKDTLMI SRTPEVTCVV VDVSQEDPEV QFNWYVDGVE VHNAKTKPRE EQFNSTYRVV  300
SVLTVLHQDW LNGKEYKCKV SNKGLPSSIE KTISKAKGQP REPQVYTLPP SQEEMTKNQV  360
SLTCLVKGFY PSDIAVEWES NGQPENNYKT TPPVLDSDGS FFLYSRLTVD KSRWQEGNVF  420
```

```
SCSVMHEALH NHYTQKSLSL SLG                                      443

SEQ ID NO: 52          moltype = AA  length = 443
FEATURE                Location/Qualifiers
source                 1..443
                       mol_type = protein
                       organism = synthetic construct
SEQUENCE: 52
EVQLVESGGG LVQPGGSLRL SCAASGFTID SFGIHWVRQA PGKGLEWVAW IAPYGGETYY  60
ADSVKGRFTI SADTSKNTAY LQMNSLRAED TAVYYCARSF FGYFDYWGQG TLVTVSSAST  120
KGPSVFPLAP CSRSTSESTA ALGCLVKDYF PEPVTVSWNS GALTSGVHTF PAVLQSSGLY  180
SLSSVVTVPS SSLGTKTYTC NVDHKPSNTK VDKRVESKYG PPCPPCPAPE AAGGPSVFLF  240
PPKPKDTLMI SRTPEVTCVV VDVSQEDPEV QFNWYVDGVE VHNAKTKPRE EQFNSTYRVV  300
SVLTVLHQDW LNGKEYKCKV SNKGLPSSIE KTISKAKGQP REPQVYTLPP SQEEMTKNQV  360
SLTCLVKGFY PSDIAVEWES NGQPENNYKT TPPVLDSDGS FFLYSRLTVD KSRWQEGNVF  420
SCSVMHEALH NHYTQKSLSL SLG                                      443

SEQ ID NO: 53          moltype = AA  length = 443
FEATURE                Location/Qualifiers
source                 1..443
                       mol_type = protein
                       organism = synthetic construct
SEQUENCE: 53
EVQLVESGGG LVQPGGSLRL SCAASGFTIS SFGIHWVRQA PGKGLEWVAW IAPYGGDTYY  60
ADSVKGRFTI SADTSKNTAY LQMNSLRAED TAVYYCARSF FGYFDYWGQG TLVTVSSAST  120
KGPSVFPLAP CSRSTSESTA ALGCLVKDYF PEPVTVSWNS GALTSGVHTF PAVLQSSGLY  180
SLSSVVTVPS SSLGTKTYTC NVDHKPSNTK VDKRVESKYG PPCPPCPAPE AAGGPSVFLF  240
PPKPKDTLMI SRTPEVTCVV VDVSQEDPEV QFNWYVDGVE VHNAKTKPRE EQFNSTYRVV  300
SVLTVLHQDW LNGKEYKCKV SNKGLPSSIE KTISKAKGQP REPQVYTLPP SQEEMTKNQV  360
SLTCLVKGFY PSDIAVEWES NGQPENNYKT TPPVLDSDGS FFLYSRLTVD KSRWQEGNVF  420
SCSVMHEALH NHYTQKSLSL SLG                                      443

SEQ ID NO: 54          moltype = AA  length = 443
FEATURE                Location/Qualifiers
source                 1..443
                       mol_type = protein
                       organism = synthetic construct
SEQUENCE: 54
EVQLVESGGG LVQPGGSLRL SCAASGFTIS SFGIHWVRQA PGKGLEWVAW IAPYGGETYY  60
ADSVKGRFTI SADTSKNTAY LQMNSLRAED TAVYYCARSF FGYFDYWGQG TLVTVSSAST  120
KGPSVFPLAP CSRSTSESTA ALGCLVKDYF PEPVTVSWNS GALTSGVHTF PAVLQSSGLY  180
SLSSVVTVPS SSLGTKTYTC NVDHKPSNTK VDKRVESKYG PPCPPCPAPE AAGGPSVFLF  240
PPKPKDTLMI SRTPEVTCVV VDVSQEDPEV QFNWYVDGVE VHNAKTKPRE EQFNSTYRVV  300
SVLTVLHQDW LNGKEYKCKV SNKGLPSSIE KTISKAKGQP REPQVYTLPP SQEEMTKNQV  360
SLTCLVKGFY PSDIAVEWES NGQPENNYKT TPPVLDSDGS FFLYSRLTVD KSRWQEGNVF  420
SCSVMHEALH NHYTQKSLSL SLG                                      443

SEQ ID NO: 55          moltype = AA  length = 443
FEATURE                Location/Qualifiers
source                 1..443
                       mol_type = protein
                       organism = synthetic construct
SEQUENCE: 55
EVQLVESGGG LVQPGGSLRL SCAASGFTIS SFGIHWVRQA PGKGLEWVAW IAPYGGDEYY  60
ADSVKGRFTI SADTSKNTAY LQMNSLRAED TAVYYCARSF FGYFDYWGQG TLVTVSSAST  120
KGPSVFPLAP CSRSTSESTA ALGCLVKDYF PEPVTVSWNS GALTSGVHTF PAVLQSSGLY  180
SLSSVVTVPS SSLGTKTYTC NVDHKPSNTK VDKRVESKYG PPCPPCPAPE AAGGPSVFLF  240
PPKPKDTLMI SRTPEVTCVV VDVSQEDPEV QFNWYVDGVE VHNAKTKPRE EQFNSTYRVV  300
SVLTVLHQDW LNGKEYKCKV SNKGLPSSIE KTISKAKGQP REPQVYTLPP SQEEMTKNQV  360
SLTCLVKGFY PSDIAVEWES NGQPENNYKT TPPVLDSDGS FFLYSRLTVD KSRWQEGNVF  420
SCSVMHEALH NHYTQKSLSL SLG                                      443

SEQ ID NO: 56          moltype = AA  length = 443
FEATURE                Location/Qualifiers
source                 1..443
                       mol_type = protein
                       organism = synthetic construct
SEQUENCE: 56
EVQLVESGGG LVQPGGSLRL SCAASGFTIS SFGIHWVRQA PGKGLEWVAW IAPYGGEEYY  60
ADSVKGRFTI SADTSKNTAY LQMNSLRAED TAVYYCARSF FGYFDYWGQG TLVTVSSAST  120
KGPSVFPLAP CSRSTSESTA ALGCLVKDYF PEPVTVSWNS GALTSGVHTF PAVLQSSGLY  180
SLSSVVTVPS SSLGTKTYTC NVDHKPSNTK VDKRVESKYG PPCPPCPAPE AAGGPSVFLF  240
PPKPKDTLMI SRTPEVTCVV VDVSQEDPEV QFNWYVDGVE VHNAKTKPRE EQFNSTYRVV  300
SVLTVLHQDW LNGKEYKCKV SNKGLPSSIE KTISKAKGQP REPQVYTLPP SQEEMTKNQV  360
SLTCLVKGFY PSDIAVEWES NGQPENNYKT TPPVLDSDGS FFLYSRLTVD KSRWQEGNVF  420
SCSVMHEALH NHYTQKSLSL SLG                                      443

SEQ ID NO: 57          moltype = AA  length = 443
FEATURE                Location/Qualifiers
```

```
source                  1..443
                        mol_type = protein
                        organism = synthetic construct
SEQUENCE: 57
EVQLVESGGG LVQPGGSLRL SCAASGFTID AFGIHWVRQA PGKGLEWVAW IAPYGGETYY  60
ADSVKGRFTI SADTSKNTAY LQMNSLRAED TAVYYCARSF FGYFDYWGQG TLVTVSSAST  120
KGPSVFPLAP CSRSTSESTA ALGCLVKDYF PEPVTVSWNS GALTSGVHTF PAVLQSSGLY  180
SLSSVVTVPS SSLGTKTYTC NVDHKPSNTK VDKRVESKYG PPCPPCPAPE AAGGPSVFLF  240
PPKPKDTLMI SRTPEVTCVV VDVSQEDPEV QFNWYVDGVE VHNAKTKPRE EQFNSTYRVV  300
SVLTVLHQDW LNGKEYKCKV SNKGLPSSIE KTISKAKGQP REPQVYTLPP SQEEMTKNQV  360
SLTCLVKGFY PSDIAVEWES NGQPENNYKT TPPVLDSDGS FFLYSRLTVD KSRWQEGNVF  420
SCSVMHEALH NHYTQKSLSL SLG                                          443

SEQ ID NO: 58           moltype = AA  length = 472
FEATURE                 Location/Qualifiers
source                  1..472
                        mol_type = protein
                        organism = Homo sapiens
SEQUENCE: 58
MGCDRNCGLI AGAVIGAVLA VFGGILMPVG DLLIQKTIKK QVVLEEGTIA FKNWVKTGTE  60
VYRQFWIFDV QNPQEVMMNS SNIQVKQRGP YTYRVRFLAK ENVTQDAEDN TVSFLQPNGA  120
IFEPSLSVGT EADNFTVLNL AVAAASHIYQ NQFVQMILNS LINKSKSSMF QVRTLRELLW  180
GYRDPFLSLV PYPVTTTVGL FYPYNNTADG VYKVFNGKDN ISKVAIIDTY KGKRNLSYWE  240
SHCDMINGTD AASFPPFVEK SQVLQFFSSD ICRSIYAVFE SDVNLKGIPV YRFVLPSKAF  300
ASPVENPDNY CFCTEKIISK NCTSYGVLDI SKCKEGRPVY ISLPHFLYAS PDVSEPIDGL  360
NPNEEEHRTY LDIEPITGFT LQFAKRLQVN LLVKPSEKIQ VLKNLKRNYI VPILWLNETG  420
TIGDEKANMF RSQVTGKINL LGLIEMILLS VGVVMFVAFM ISYCACRSKT IK          472

SEQ ID NO: 59           moltype = AA  length = 410
FEATURE                 Location/Qualifiers
source                  1..410
                        mol_type = protein
                        organism = synthetic construct
SEQUENCE: 59
GDLLIQKTIK KQVVLEEGTI AFKNWVKTGT EVYRQFWIFD VQNPQEVMMN SSNIQVKQRG  60
PYTYRVRFLA KENVTQDAED NTVSFLQPNG AIFEPSLSVG TEADNFTVLN LAVAAASHIY  120
QNQFVQMILN SLINKSKSSM FQVRTLRELL WGYRDPFLSL VPYPVTTTVG LFYPYNNTAD  180
GVYKVFNGKD NISKVAIIDT YKGKRNLSYW ESHCDMINGT DAASFPPFVE KSQVLQFFSS  240
DICRSIYAVF ESDVNLKGIP VYRFVLPSKA FASPVENPDN YCFCTEKIIS KNCTSYGVLD  300
ISKCKEGRPV YISLPHFLYA SPDVSEPIDG LNPNEEEHRT YLDIEPITGF TLQFAKRLQV  360
NLLVKPSEKI QVLKNLKRNY IVPILWLNET GTIGDEKANM FRSQVTGKIN             410

SEQ ID NO: 60           moltype = AA  length = 472
FEATURE                 Location/Qualifiers
source                  1..472
                        mol_type = protein
                        organism = Mus musculus
SEQUENCE: 60
MGCDRNCGLI AGAVIGAVLA VFGGILMPVG DMLIEKTIKR EVVLEEGTTA FKNWVKTGTT  60
VYRQFWIFDV QNPDDVAKNS SKIKVKQRGP YTYRVRYLAK ENITQDPEDH TVSFVQPNGA  120
IFEPSLSVGT EDDNFTVLNL AVAAAPHIYQ NSFVQVVLNS LIKKSKSSMF QTRSLKELLW  180
GYKDPFLSLV PYPISTTVGV FYPYNDTVDG VYKVFNGKDN ISKVAIIESY KGKRNLSYWP  240
SYCDMINGTD AASFPPFVEK SRTLRFFSSD ICRSIYAVFG SEIDLKGIPV YRFVLPANAF  300
ASPLQNPDNH CFCTEKVISN NCTSYGVLDI GKCKEGKPVY ISLPHFLHAS PDVSEPIEGL  360
HPNEDEHRTY LDVEPITGFT LQFAKRLQVN ILVKPARKIE ALKNLKRPYI VPILWLNETG  420
TIGDEKAEMF KTQVTGKIKL LGMVEMALLG IGVVMFVAFM ISYCACKSKN GK          472

SEQ ID NO: 61           moltype = AA  length = 410
FEATURE                 Location/Qualifiers
source                  1..410
                        mol_type = protein
                        organism = Macaca mulatta
SEQUENCE: 61
GDMLIEKTIK REVVLEEGTT AFKNWVKTGT TVYRQFWIFD VQNPDDVAKN SSKIKVKQRG  60
PYTYRVRYLA KENITQDPED HTVSFVQPNG AIFEPSLSVG TEDDNFTVLN LAVAAAPHIY  120
QNSFVQVVLN SLIKKSKSSM FQTRSLKELL WGYKDPFLSL VPYPISTTVG VFYPYNDTVD  180
GVYKVFNGKD NISKVAIIES YKGKRNLSYW PSYCDMINGT DAASFPPFVE KSRTLRFFSS  240
DICRSIYAVF GSEIDLKGIP VYRFVLPANA FASPLQNPDN HCFCTEKVIS NNCTSYGVLD  300
IGKCKEGKPV YISLPHFLHA SPDVSEPIEG LHPNEDEHRT YLDVEPITGF TLQFAKRLQV  360
NILVKPARKI EALKNLKRPY IVPILWLNET GTIGDEKAEM FKTQVTGKIK             410

SEQ ID NO: 62           moltype = AA  length = 472
FEATURE                 Location/Qualifiers
source                  1..472
                        mol_type = protein
                        organism = synthetic construct
SEQUENCE: 62
MGCDRNCGLI TGAVIGAVLA VFGGILMPVG DMLIQKTIKK EVVLEEGTIA FKNWVKTGTE  60
IYRQFWIFDV QNPQEVMMNS SNIQVKQRGP YTYRVRFLAK ENITQDPKDN TVSFLQPNGA  120
```

-continued

```
IFEPSLSVGT EADNFTVLNL AVAAASHIYP NPFVQVVLNS LINKSKSSMF QVRTLRELLW  180
GYTDPFLSLV PYPVSTRVGM FYPYNNTADG VYKVFNGKDS ISKVAIIDTY KGKRNLSYWE  240
SYCDMINGTD AASFPPFVEK SQVLQFFSSD ICRSIYAVFE SDVNLKGIPV YRFVLPSKAF  300
ASPVQNPDNH CFCTEKIISK NCTSYGVLDI SKCKEGKPVY ISLPHFLYAS PDVSETIDGL  360
NPNEEEHRTY LDIEPITGFT LQFAKRLQVN LLVKPSNKIQ VLKRLKRNYI VPILWLNETG  420
TIGDEKAKMF RSQVTGKINL LGLIEMILLS VGVVMFVAFM ISYCACRSKT IK          472

SEQ ID NO: 63          moltype = AA  length = 410
FEATURE                Location/Qualifiers
source                 1..410
                       mol_type = protein
                       organism = synthetic construct
SEQUENCE: 63
GDMLIQKTIK KEVVLEEGTI AFKNWVKTGT EIYRQFWIFD VQNPQEVMMN SSNIQVKQRG  60
PYTYRVRFLA KENITQDPKD NTVSFLQPNG AIFEPSLSVG TEADNFTVLN LAVAAASHIY  120
PNPFVQVVLN SLINKSKSSM FQVRTLRELL WGYTDPFLSL VPYPVSTRVG MFYPYNNTAD  180
GVYKVFNGKD SISKVAIIDT YKGKRNLSYW ESYCDMINGT DAASFPPFVE KSQVLQFFSS  240
DICRSIYAVF ESDVNLKGIP VYRFVLPSKA FASPVQNPDN HCFCTEKIIS KNCTSYGVLD  300
ISKCKEGKPV YISLPHFLYA SPDVSETIDG LNPNEEEHRT YLDIEPITGF TLQFAKRLQV  360
NLLVKPSNKI QVLKRLKRNY IVPILWLNET GTIGDEKAKM FRSQVTGKIN             410

SEQ ID NO: 64          moltype = DNA  length = 38
FEATURE                Location/Qualifiers
source                 1..38
                       mol_type = other DNA
                       organism = synthetic construct
SEQUENCE: 64
aatcacgatg tgatattcaa atgacccaga gcccgagc                          38

SEQ ID NO: 65          moltype = DNA  length = 33
FEATURE                Location/Qualifiers
source                 1..33
                       mol_type = other DNA
                       organism = synthetic construct
SEQUENCE: 65
aatcgtacgt ttgatttcca ctttggtgcc ttg                               33

SEQ ID NO: 66          moltype = DNA  length = 39
FEATURE                Location/Qualifiers
source                 1..39
                       mol_type = other DNA
                       organism = Synthetic construct
SEQUENCE: 66
aatacgcgtg tcctgtccga agtgcagctg gtggaatcg                         39

SEQ ID NO: 67          moltype = DNA  length = 27
FEATURE                Location/Qualifiers
source                 1..27
                       mol_type = other DNA
                       organism = Synthetic construct
SEQUENCE: 67
aatgctagcc gagctcacgg taacaag                                      27
```